(12) United States Patent
Narimatsu et al.

(10) Patent No.: US 8,623,608 B2
(45) Date of Patent: Jan. 7, 2014

(54) METHOD FOR MEASURING GLYCOPROTEIN, METHOD FOR EXAMINING LIVER DISEASE, REAGENT FOR QUANTITATIVE DETERMINATION OF GLYCOPROTEIN, AND GLYCAN-MARKER GLYCOPROTEIN AS AN INDEX FOR CLINICAL CONDITIONS OF LIVER DISEASE

(75) Inventors: Hisashi Narimatsu, Ibaraki (JP); Yuzuru Ikehara, Ibaraki (JP); Atsushi Kuno, Ibaraki (JP); Maki Sogabe, Ibaraki (JP); Yasuhito Tanaka, Aichi (JP); Masashi Mizokami, Chiba (JP); Kiyoaki Ito, Chiba (JP); Shunsuke Matsubara, Hyogo (JP); Chikayuki Tsuruno, Hyogo (JP); Youichi Takahama, Hyogo (JP); Takashi Kagawa, Hyogo (JP); Shinya Nagai, Hyogo (JP)

(73) Assignees: Sysmex Corporation, Hyogo (JP); National Institute of Advanced Industrial Science and Technology, Tokyo (JP); Nagoya University, Aichi (JP); National Center for Global Health and Medicine, Tokyo (JP)

( * ) Notice: Subject to any disclaimer, the term of this patent is extended or adjusted under 35 U.S.C. 154(b) by 0 days.

(21) Appl. No.: 13/374,807

(22) Filed: Jan. 13, 2012

(65) Prior Publication Data
US 2012/0172247 A1 Jul. 5, 2012

(30) Foreign Application Priority Data

Jul. 14, 2009 (JP) ................................ 2009-165795
Dec. 18, 2009 (JP) ................................ 2009-287243

(51) Int. Cl.
*G01N 33/53* (2006.01)
*G01N 33/543* (2006.01)

(52) U.S. Cl.
USPC .............. 435/7.1; 436/94; 436/518; 436/827; 435/7.8

(58) Field of Classification Search
None
See application file for complete search history.

(56) References Cited

U.S. PATENT DOCUMENTS

2007/0037221 A1* 2/2007 Block et al. .................... 435/7.2
2009/0117591 A1* 5/2009 Corrales Izquierdo et al. .............. 435/7.4

FOREIGN PATENT DOCUMENTS

| EP | 1918715 A1 | 5/2008 |
|---|---|---|
| JP | 08-184594 A | 7/1996 |
| JP | 10-026622 A | 1/1998 |
| JP | 2007-161633 A | 6/2007 |
| JP | 2009-500597 A | 1/2009 |

OTHER PUBLICATIONS

Inohara, Hidenori, Shiro Akahani, Kirston Koths, and Avraham Raz, "Interactions between Galectin-3 and Mac-2-Binding Protein Mediate Cell-Cell Adhesion," Oct. 1, 1996, Cancer Research, 56, pp. 4530-4534.*

Piller, Veronique, Friedrich Piller, and Jean-Pierre Caartron, "Comparison of the carbohydrate-binding specificities of seven N-acetyl-D-galactosamine-recognizing lectins," Jul. 1990, European Journal of Biochemistry, vol. 191, Issue 2 pp. 461-466.*

Piller, Veronique et al., "Comparison of the carbohydrate-binding specificities of seven N-acetyl-D-galactosamine-recognizing lectins," 1990, European Journal of Biochemistry, 191, pp. 461-466.*

Ulmer, Tricia A. et al. "Tumor-Associated Antigen 90K/Mac-2-Binding Protein: Possible Role in Colon Cancer," 2006, Journal of Cellular Biochemistry, 98, pp. 1351-1366.*

Yamashita, Katsuko et al., "Carbohydrate Binding Properties of Complex-type Oligosaccharides on Immobilized *Datura stramonium* Lectin," 1987, The Journal of Biological Chemistry, vol. 262, No. 4, pp. 1602-1607.*

Basili, Stefania et al., "Lipoprotein (a) serum levels in patients with hepatocarcinoma," *Clinica Chimica Acta*, vol. 262, pp. 53-60.

Block, Timothy M. et al., "Use of targeted glycoproteomics to identify serum glycoproteins that correlate with liver cancer in woodchucks and humans," *PNAS*, Jan. 2005, vol. 102, No. 3, pp. 779-784.

Hachem, Houda et al., "Serum Apolipoproteins A-I, A-II and B in Hepatic Metastases Comparison with other Liver Diseases: Hepatomas and Cirrhosis," *J. Clin Chem. Clin. Biochem.*, vol. 24, 1986, pp. 161-166.

Harazono, Akira et al., "Site-specific glycosylation analysis of human apolipoprotein B100 using LC/ESI MS/MS," *Glycobiology*, 2005, vol. 15, No. 5, pp. 447-462.

Ikehara, Yuzuru et al., "Search for Glycan Biomarker for Hepatocellular Carcinoma," *Biotechnology Symposium Proceedings*, 2008, vol. 26, pp. 21-26 (17 pages with English translation).

(Continued)

*Primary Examiner* — Christopher M Gross
*Assistant Examiner* — Christopher Reyes
(74) *Attorney, Agent, or Firm* — Brinks Gilson & Lione

(57) ABSTRACT

An object of the present invention is to provide a method for measuring a glycan-marker glycoprotein, by which liver disease can be detected with higher accuracy than is possible with conventional methods. Also, an object of the present invention is to provide a method for examining liver disease, by which liver disease can be detected with higher accuracy than is possible with conventional methods. Disclosed is a method for measuring at least one glycoprotein selected from alpha-1-acid glycoprotein (AGP) and Mac-2-binding protein (M2BP) contained in a sample collected from a subject, comprising: measuring AGP binding to a first lectin selected from AOL and MAL, when the glycoprotein is AGP; and measuring M2BP binding to a second lectin selected from WFA, BPL, AAL, RCA120, and TJAII, when the glycoprotein is M2BP.

13 Claims, 37 Drawing Sheets
(6 of 37 Drawing Sheet(s) Filed in Color)

(56) References Cited

OTHER PUBLICATIONS

Ito, Hiromi et al., "Strategy for Glycoproteomics: Identification of Glyco-Alteration Using Multiple Glycan Profiling Tools," *Journal of Proteome Research*, 2009, vol. 8, pp. 1358-1367.

Kaji, Hiroyuki et al., "Glycoproteomics in Strategy for Searching Disease Biomarker," *Biotechnology Symposium Proceedings*, 2008, vol. 26, pp. 125-126 (7 pages with English translation).

Morelle, Willy et al., "Mass spectrometric approach for screening modifications of total serum N-glycome in human diseases: application to cirrhosis," *Glycobiology*, 2006, vol. 16, No. 4, pp. 281-293.

Tarantino, G. et al., "Serum APO B Levels in Hepatocellular Failure," 1983, *Clinica, Medica, University of Medicine and Surgery*, Naples, Italy, pp. 7S-18S.

International Search Report for International Application No. PCT/JP2010/061791, dated Sep. 28, 2010, 4 pages.

International Preliminary Report on Patentability for International Application No. PCT/JP2010/061791, dated Mar. 13, 2012, 6 pages.

Lee, Eun Young et al., "Development of a rapid, immunochromatographic strip test for serum asialo α1-acid glycoprotein in patients with hepatic disease," Journal of Immunological Methods, 308, 2006, pp. 116-123.

Liljeblad, Mathias et al., "A Lectin Immunosensor Technique for Determination of α1-Acid Glycoprotein Fucosylation," Analytical Biochemistry, 288, 2001, pp. 216-224.

Matsumura, Kengo et al., "Carbohydrate Binding Specificity of a Fucose-specific Lectin from *Aspergillus oryzae*," The Journal of Biological Chemistry, vol. 282, No. 21, May 25, 2007, pp. 15700-15708.

Ryden, Ingvar et al., "Diagnostic Accuracy of α1-Acid Glycoprotein Fucosylation for Liver Cirrhosis in Paitents Undergoing Hepatic Biopsy," Clinical Chemistry, 48:12, 2002, pp. 2195-2201.

International Search Report for International Application No. PCT/JP2010/061891, dated Sep. 21, 2010, 4 pages.

Matsuda, Atsushi et al., "Development of an all-in-one technology for glycan profiling targeting formalin-embedded tissue sections," Biochemical and Biophysical Research Communications, vol. 370, 2008, pp. 259-263.

Extended European Search Report for European Application No. 10799855.1, dated Dec. 18, 2012, 3 pages.

* cited by examiner

METHOD FOR MEASURING GLYCOPROTEIN, METHOD FOR EXAMINING LIVER DISEASE, REAGENT FOR QUANTITATIVE DETERMINATION OF GLYCOPROTEIN, AND GLYCAN-MARKER GLYCOPROTEIN AS AN INDEX FOR CLINICAL CONDITIONS OF LIVER DISEASE

RELATED APPLICATIONS

This application is a continuation of PCT/JP2010/061891 filed on Jul. 14, 2010, which claims priority to Japanese Application Nos. 2009-165795 filed on Jul. 14, 2009 and 2009-287243 filed on Dec. 18, 2009. The entire contents of these applications are incorporated herein by reference.

BACKGROUND OF THE INVENTION

1. Field of the Invention

The present invention relates to a method for measuring at least one glycoprotein selected from alpha-1-acid glycoprotein (AGP) and Mac-2-binding protein (M2BP), a method for examining liver disease using at least one glycoprotein selected from AGP and M2BP, and a glycan-marker glycoprotein with which hepatic cell carcinoma and background liver status such as regarding inflammation-fiber formation can be detected based on glyco-alterations.

2. Description of the Related Art

Liver cancer can be roughly classified into primary liver cancer and metastatic liver cancer developed in the liver. It is said that hepatic cell carcinoma accounts for 90% of primary liver cancer cases.

Hepatic cell carcinoma patients are often infected with hepatitis type C virus or hepatitis type B virus that constitutes the underlying cause of a disease. The disease proceeds from acute viral hepatitis to chronic viral hepatitis, and then to cirrhosis. Long after the development of viral hepatitis, the disease can become cancerous for the first time. In the case of cirrhosis, normal hepatocytes decrease through repetition of inflammation and regeneration, and then the affected liver becomes an organ composed of fibrous tissue. For example, there are said to be 3 million type C hepatitis patients in Japan alone and 10 million or more in China and Africa. Also, in the case of type B and/or type C hepatitis patients, the carcinogenic rate from chronic hepatitis is an annual rate of 0.8% for mild chronic hepatitis (F1), an annual rate of 0.9% for moderate chronic hepatitis (F2), and an annual rate of 3.5% for severe chronic hepatitis (F3). Furthermore, the probability of cirrhosis (F4) becoming cancerous increases to an annual rate of as high as 7% (FIG. 1 and FIG. 2). Also, in the course of liver disease, firstly, functions start to disappear because of chronic hepatitis as the clinical conditions proceed, pathological structure(s) appear because of cirrhosis, and fiber formation of the liver proceeds. In this manner, the tissue image is altered (FIG. 3).

Early detection of cancer is important for cancer treatment. Also, in the case of hepatic cell carcinoma, early detection of cancer significantly influences treatment and postoperative prognosis. The 5-year survival rate after hepatic resection is 80% for stage I cancer and only 38% for stage IV cancer.

As liver cancer markers, α-fetoprotein (AFP) and a protein induced by Vitamin K absence or antagonist-II (PIVKA-II) are currently known (patent documents 1 and 2), but both the specificity and the sensitivity thereof are insufficient. Hence, physical examination for early detection of liver cancer is currently conducted with the use of liver cancer markers and imaging studies such as ultrasonography, computed tomography (CT), and magnetic resonance imaging (MRI).

Also, non-patent document 1 describes an attempt to measure fucosylated AGP in serum using AAL lectin so as to detect cirrhosis. However, the technique described in non-patent document 1 is unsatisfactory in view of liver disease detection performance, since the specificity is about 87% and the accuracy is about 77%, although the sensitivity is about 66%, as understood from the results described in Table 2.

Also, non-patent document 2 describes an experiment conducted by measuring asialo AGP in sera of healthy subjects, acute hepatitis patients, chronic hepatitis patients, cirrhosis patients, and hepatic cell carcinoma patients by immunochromatography using RCA lectin, so as to reveal whether each liver disease could be determined to be positive or not. However, the technique described in non-patent document 2 is unsatisfactory in view of liver disease detection performance, since the sensitivity of cirrhosis detection, for example, is about 88%, but the false positive rate for chronic hepatitis patients is 63%, as understood from the results described in Table 2.

PRIOR ART DOCUMENTS

Patent documents

Patent document 1: JP Patent Publication (Kokai) No. 10-26622 A (1998)

Patent document 2: JP Patent Publication (Kokai) No. 8-184594 A (1996)

Non-patent Documents

Non-patent document 1: Ingvar Ryden et al., Diagnostic Accuracy of α1-Acid Glycoprotein Fucosylation for Liver Cirrhosis in Patients Undergoing Hepatic Biopsy, Clinical Chemistry 48: 12, 2195-2201 (2002)

Non-patent document 2: Eun Young Lee et al., Development of a rapid, immunochromatographic strip test for serum asialo al-acid glycoprotein in patients with hepatic disease, Journal of Immunological Methods 308 (2006) 116-123

SUMMARY OF THE INVENTION

An object of the present invention is to provide a method for measuring a glycan-marker glycoprotein, by which liver disease can be detected with higher accuracy than conventional methods. Also, an object of the present invention is to provide a method for examining liver disease, by which liver disease can be detected with higher accuracy than conventional methods. Also, an object of the present invention is to provide a reagent(s) for quantitative determination of a glycoprotein(s) to be used for the above measurement methods. Moreover, an object of the present invention is to provide a glycan-marker glycoprotein as an index for clinical conditions of liver disease, with which clinical conditions of liver disease can be distinguished from one another according to the progress of liver disease.

The method for measuring at least one glycoprotein selected from alpha-1-acid glycoprotein (AGP) and Mac-2-binding protein (M2BP) contained in a sample collected from a subject is characterized in that: when the glycoprotein is AGP, AGP that binds to first lectin selected from AOL and MAL is measured; and when the glycoprotein is M2BP, M2BP that binds to second lectin selected from WFA, BPL, AAL, RCA120, and TJAII is measured.

According to the measurement method of the present invention, a glycan-marker glycoprotein, with which liver disease such as cirrhosis can be examined with high reliability, can be conveniently measured.

Furthermore, according to the glycan-marker glycoprotein as an index for clinical conditions of liver disease of the present invention, examination becomes possible with higher accuracy than is possible with existing markers and with minute amounts of serum. Thus, monitoring of the progress of liver fiber formation becomes possible, so that not only the understanding of the development of clinical conditions but also the evaluation of improvement in fiber formation in the liver or liver inflammation after antiviral therapy using interferon, for example, become possible.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Figure 1:
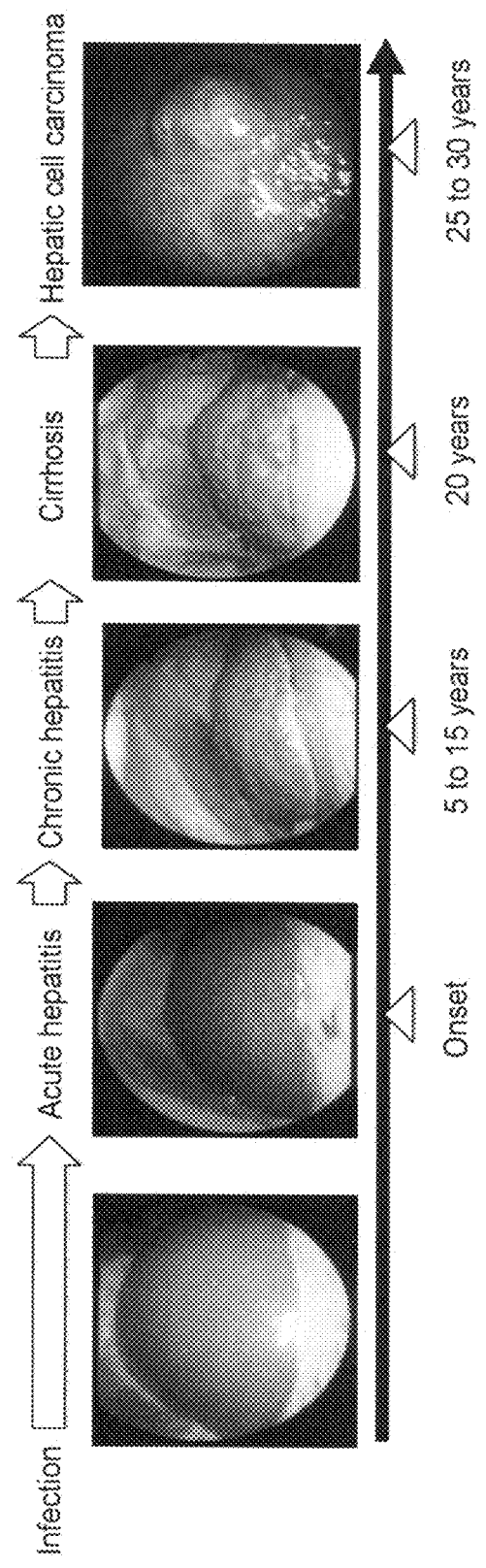
FIG. 1 shows the time course from infection with type C hepatitis to hepatic cell carcinoma and changes in liver status.
Figure 2:
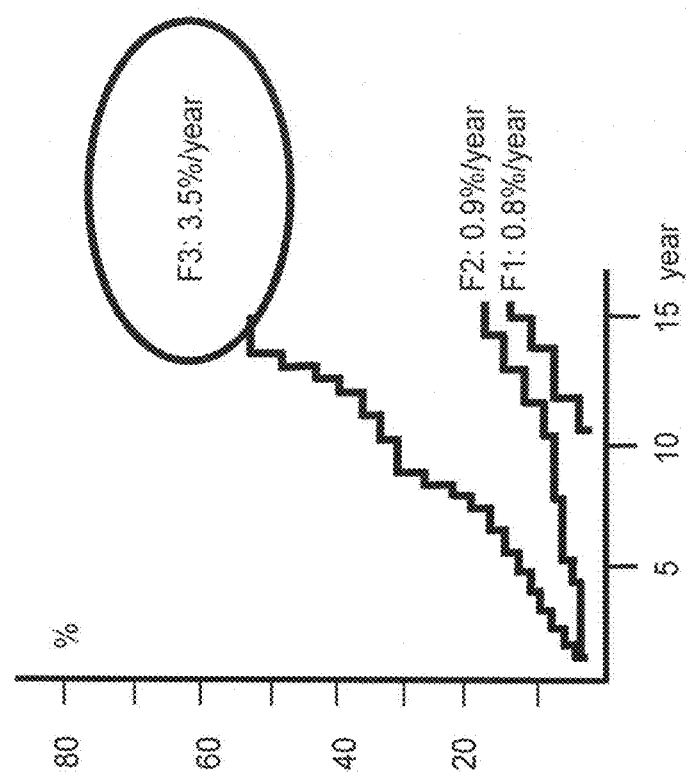
FIG. 2 shows carcinogenic rates (from chronic hepatitis to hepatic cell carcinoma).
Figure 3:
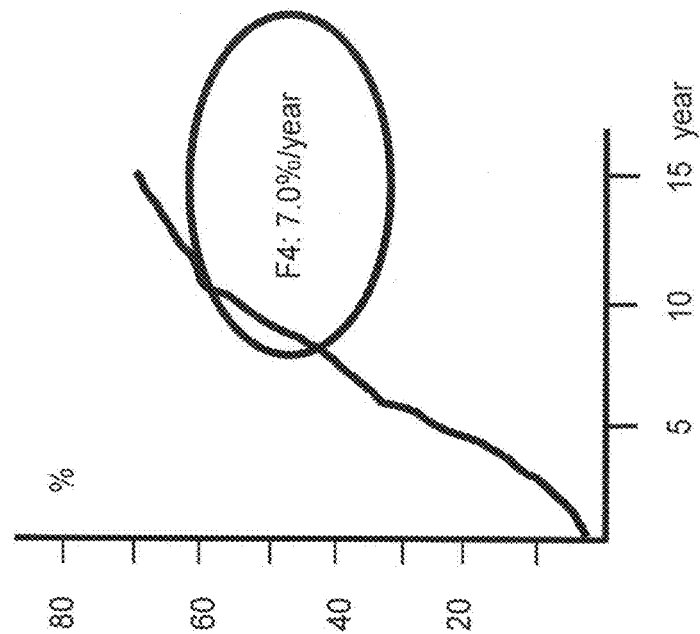
FIG. 3 shows carcinogenic rates (from cirrhosis to hepatic cell carcinoma).

1. Current Status of Chronic Liver Disease 1-1. Pathological Conditions of Liver Disease After infection with hepatitis type B virus or hepatitis type C virus, transition from acute-stage inflammation to chronic-stage inflammation takes place for 5-15 years. In particular, type C hepatitis that has transitioned to the chronic stage is merely cured naturally, and the liver functions decrease to result in cirrhosis. The time course from infection with type C hepatitis to hepatic cell carcinoma and changes in liver status are shown in FIG. 1. For definition of clinical conditions from chronic hepatitis to cirrhosis, fibrous alterations that appear in the hepatic region of Glisson's capsule and hepatic lobules are captured pathomorphologically so that the disease is classified into the mild (F1), moderate (F2), severe (F3), or cirrhosis stage (F4). The progress of fiber formation correlates with increased risk of hepatic cell carcinoma. As shown in FIG. 2, whereas the annual rate is 1% or less in the case of F1 or F2, the annual rate increases to 3-4% in the case of F3. In the case of cirrhosis (F4) diagnosed through confirmation of a tissue image showing the further progress of fiber formation, hepatic cell carcinoma appears at an annual rate of about 7% as shown in FIG. 3. Therefore, it is particularly important for efficient detection and treatment of hepatic cell carcinoma to conveniently select patients at the F3 stage and the F4 stage and conduct follow-ups for such subjects to be subjected to detailed examination.

The medical benefits project in Japan for type B and type C hepatitis patients are exclusively intended for fiber formation at the stages ranging from F1 to F3 as determined by histopathological diagnosis on liver biopsy specimens. On the other hand, when diseases are diagnosed at the F4 stage, they are classified as cirrhosis. Hence, only some type B and type C hepatitis patients are aided by interferon treatment in the medical benefits project. In such cases, satisfactory treatment results cannot be obtained.

1-2. Evaluation of Suppression of Fiber Formation by Antiviral Therapy

In the case of type C chronic hepatitis, PEG-IFN+RBV therapy is applied. In the case of a type C cirrhosis compensatory period, sole administration of interferon is applied. Meanwhile, in the case of type B hepatitis (chronic hepatitis or cirrhosis), treatment is mainly performed with a nucleic acid analog and inflammation and fiber formation evaluation markers are thought to be essential. In particular, clinical application of serum biomarkers is broadly expected for diagnostic and evaluation purposes.

1-3. Hepatic Cell Carcinoma

It is considered that microbiological factors (through infection with hepatitis type B virus or hepatitis type C virus) and environmental factors alternately have significant impact on hepatic cell carcinoma. In Japan, it is known that about 90% of hepatic cell carcinoma patients have a history of infection with hepatitis type B or hepatitis type C virus and that chronic hepatitis patients and cirrhosis patients develop hepatic cell carcinoma. In addition to the presence of viruses, being male, being elderly, alcoholism, tobacco, the presence of aflatoxin (a fungal toxin), and the like are suggested as hepatic cell carcinoma risk factors (Clinical guidelines for liver cancer, International Medical Information Center (Foundation)).

1-4. Early Diagnosis of Hepatic Cell Carcinoma

Hepatic cell carcinoma is currently detected by mainly the measurement of liver cancer markers such as AFP and PIVKA-II in a serum sample from a subject and diagnostic imaging performed mainly by ultrasonography (echo test). Diagnostic imaging is generally performed by a first test using ultrasonography or CT and then by MRI or angiography when some abnormalities are found.

1-5. Discrimination of Groups at High Risk of Cancer in View of Prevention of Hepatic Cell Carcinoma About 90% of hepatic cell carcinoma patients have experienced transition from hepatitis due to infection with hepatitis type B virus or hepatitis type C virus in Japan. Hence, patients to be subjected to detailed examination can be discriminated using viral infection and decreased liver functions as indices.

However, even in the case of cirrhosis (F4) patients for which hepatic cell carcinoma appears at an annual rate of about 7%, it must be said that repetition of expensive detailed examinations that are highly invasive every 3 months for early detection and treatment of cancer is a significant economic and physical burden for the patients. This can especially be said for the case of F3, which has an annual carcinogenic rate of 3-4%. Furthermore, in view of the about 50% success rate of the treatment of hepatitis type C virus with interferon, it is necessary to clarify the stage (between cirrhosis and the onset of hepatic cell carcinoma) of each chronic hepatitis patient and thus to perform clinical follow-up for a considerable number of the patients for which interferon treatment has failed. Specifically, current treatment for the disease that proceeds from hepatitis to hepatic cell carcinoma is in a status in which the risk of cancer should be ranked for hepatitis to cirrhosis patients by a convenient test such as a blood test and then diagnostic treatment of hepatic cell carcinoma appropriate for each result should be performed.

Figure 4:
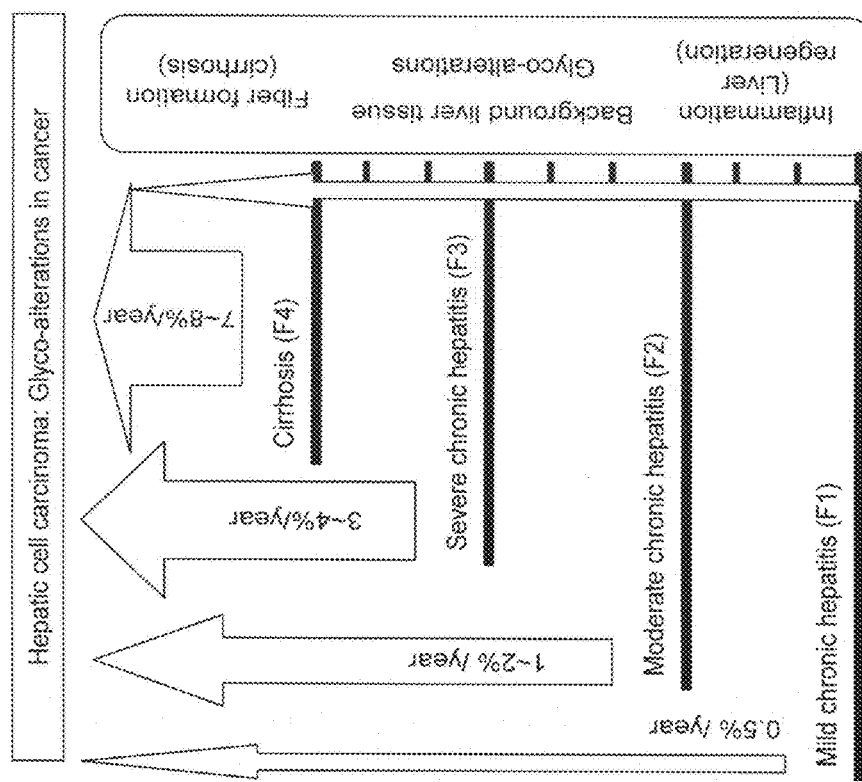
FIG. 4 shows the relationship between changes in background liver tissue and carcinogenesis.
Figure 5:
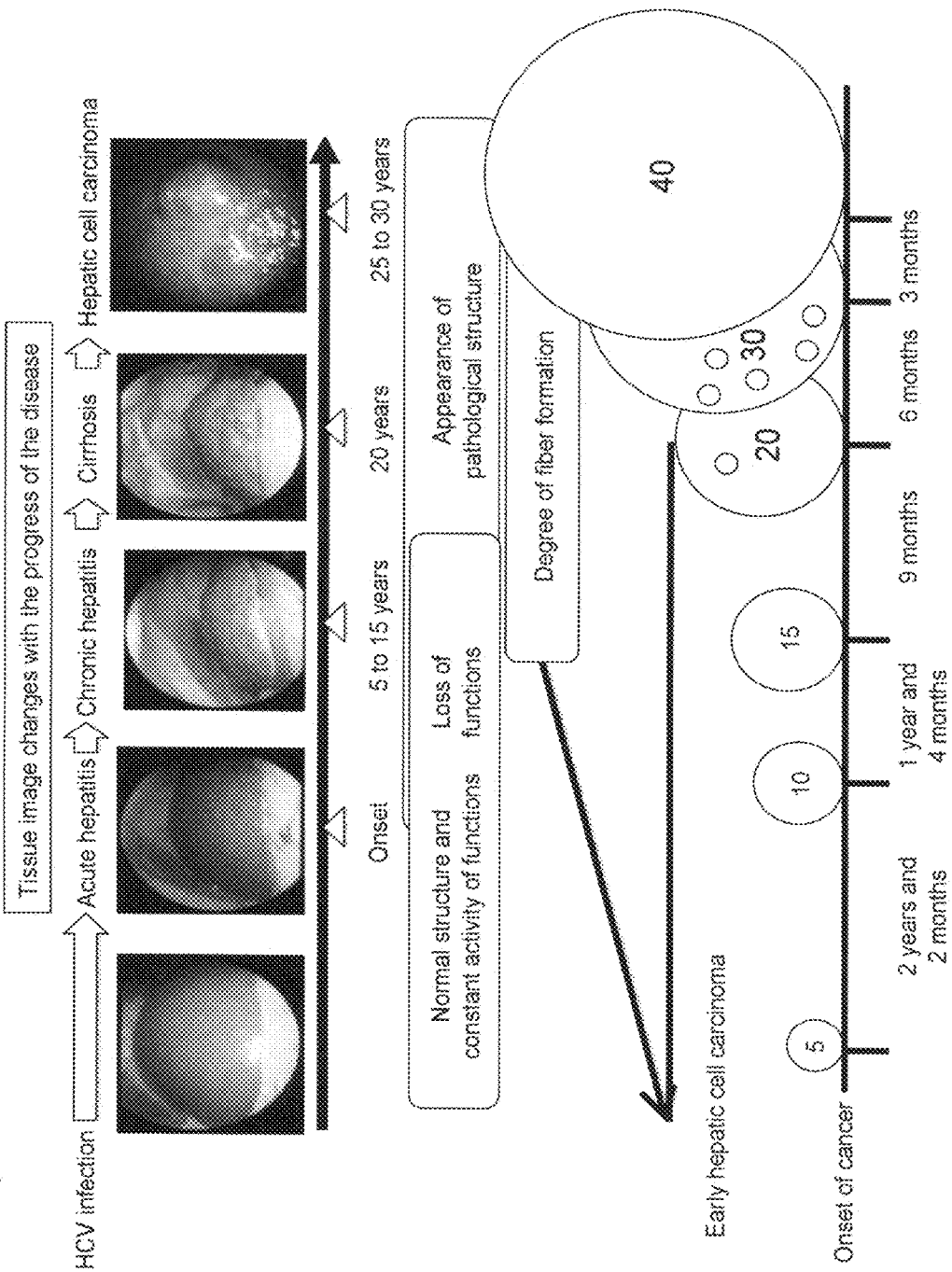
FIG. 5 shows structural changes in the liver from infection to carcinogenesis.
Figure 6:
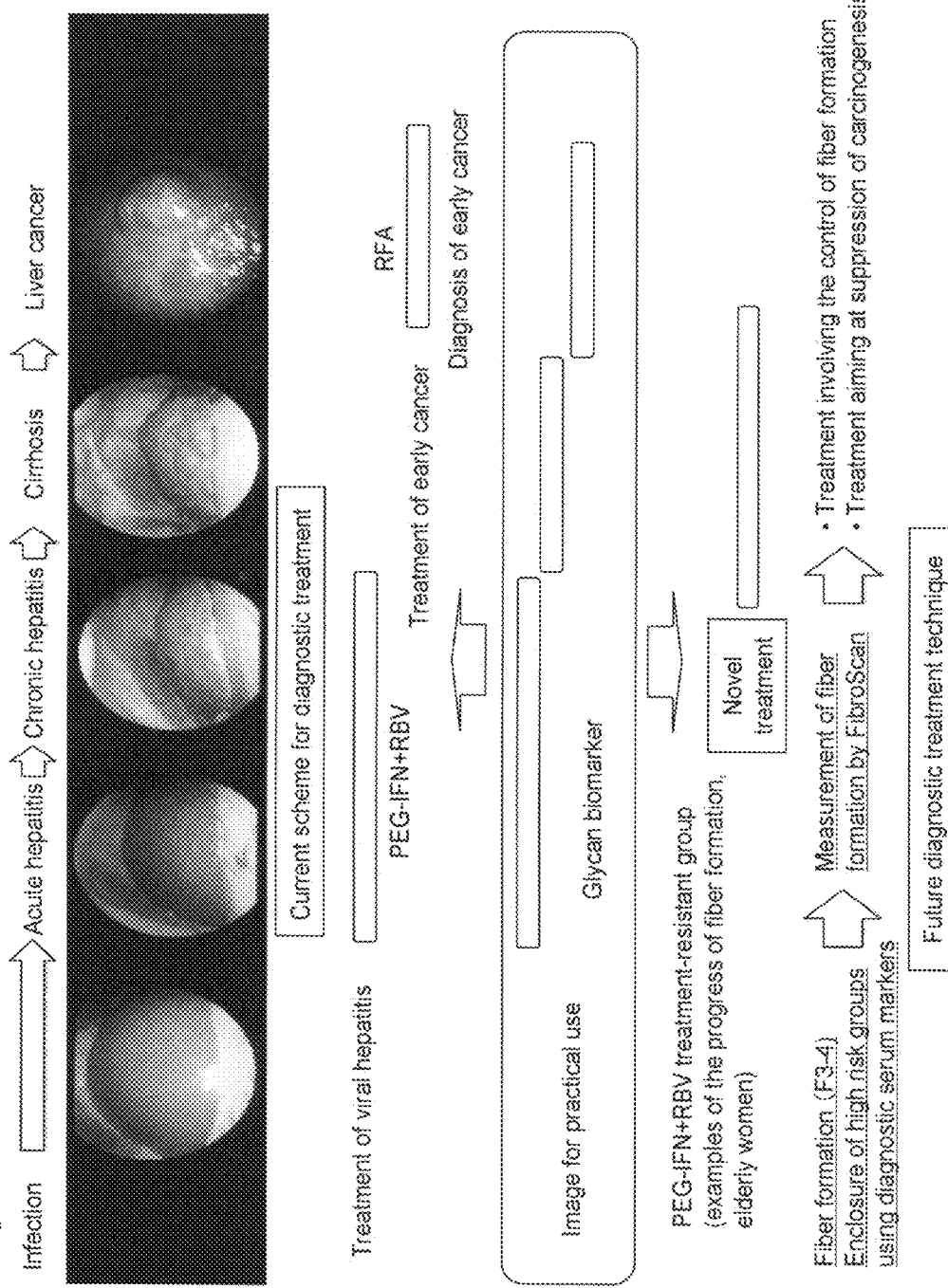
FIG. 6 shows the relationship between changes in liver status and diagnostic treatment schemes.

From the perspective of clinical pathology, the degree of fiber formation correlates with the risk of cirrhosis or the risk of hepatic cell carcinoma. Therefore, we have found that the development of an inspection technique by which the progress of fiber formation can be determined serologically and quantitatively can solve the problem. As shown in FIG. 4, infection with hepatitis type C virus that occurs in the liver induces fiber formation in order to regenerate damaged hepatocytes and repair cicatrices. The risk of cancer increases as fiber formation in the liver proceeds. Hence, "the degree of fiber formation" can be used as an index for the onset of cancer. In background liver tissue in which cancer develops, component cells are changed. Accordingly, it is inferred that glyco-alterations take place as fiber formation proceeds. As shown in FIG. 5, infection leads to the onset of cancer with time. At this time, the loss of constant activity such as the loss of normal structures and the loss of normal functions is observed in the liver simultaneously with the advent of pathological structures characterized by fiber formation. Hepatic cell carcinoma is known to undergo transition from early hepatic cell carcinoma to classical hepatic cell carcinoma, such that the properties of the cells are altered. In cases of early hepatic cell carcinoma of a size of larger than 2 cm, classical hepatic cell carcinoma appears. FIG. 6 shows the relationship between changes in liver status and diagnostic treatment schemes. Whereas peginterferon/ribavirin combination therapy (PEG-IFN+RBV therapy) is performed for chronic hepatitis, radiowave cauterization therapy (RFA) is performed for early hepatic cell carcinoma. There are neither diagnostic testing methods nor effective therapeutic methods for cirrhosis. The glycan-marker glycoproteins of the present invention can distinguish among chronic hepatitis, cirrhosis, and hepatic cell carcinoma, and thus can be used as an index in the development of new treatment for cirrhosis. Also, the glycan-marker glycoproteins are expected to enable quantitative evaluation of fiber formation through use in combination with the Fibroscan. The glycan-marker glycoproteins also make it possible to discriminate cases with fiber formation (F3-4). The glycan-marker glycoproteins are expected to be used as serum evaluation markers for evaluation of therapeutic effects, in addition to the quantitative diagnosis of fiber formation, upon clinical introduction of the treatment of the progress of fiber formation in the liver or suppression of the onset of cancer.

2. Liver-disease-Specific Glyco-alterations in New Glycan-marker Glycoproteins as Indices for Clinical Conditions of Liver Disease AGP and M2BP are the new glycan-marker glycoproteins used as indices for clinical conditions of liver disease of the present invention. They are found to experience glyco-alterations that are characteristic of chronic hepatitis, cirrhosis, and hepatic cell carcinoma caused by the development and progress of diseases due to viral infection. Such marker glycoproteins capable of specifying clinical conditions of liver disease using glyco-alterations accompanying the progress of clinical conditions of viral liver disease as indices are referred to as glycan markers as indices for clinical conditions of liver disease.

Detection of glyco-alterations in AGP and M2BP that are new glycan markers as indices for clinical conditions of liver disease of the present invention is effective for distinguishing among clinical conditions of viral liver diseases such as hepatic cell carcinoma, cirrhosis, fiber formation in the liver (F3 and F4 markers), and chronic hepatitis so as to distinguish among the diseases. However, such glyco-alterations in these markers differ in type and rate depending on disease type and the degree of progress. Therefore, lectin probes reflecting disease-specific glyco-alterations should be statistically selected in order to construct detection kits specialized in each subject using the markers.

3. Verification of Liver Disease-specific Glyco-alterations in Glycan-marker Glycoproteins Disease-specific glyco-alterations existing on AGP and M2BP are verified using lectin arrays described later. More specifically, an antibody-overlay lectin array method is employed. Based on the results obtained by measurement of the above marker glycoproteins using lectin arrays, 1) the degree of changes in measured values and lectin signals at which the changes are observed depending on the progress of the disease, 2) the stage (initial or late stage) at which changes in measured value are most significant, and 3) whether or not information concerning changes in measured value contributes to disease control are examined and the usefulness thereof is evaluated, so that the appropriateness of each marker for clinical conditions of liver disease is verified.

More specific methods for selecting lectin probes appropriate for using glycan-marker glycoproteins for monitoring of the progress of fiber formation in the liver or detection of cirrhosis are as described below.

Figure 7:
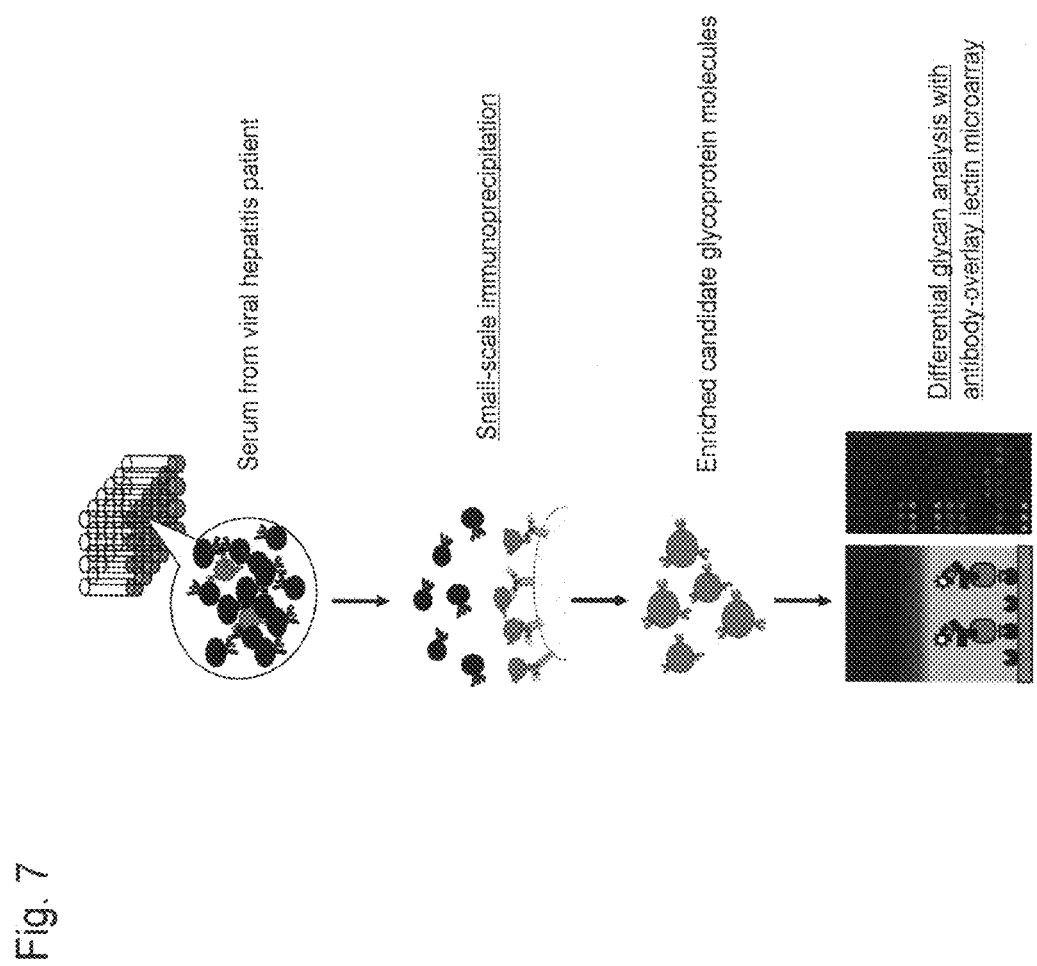
FIG. 7 shows experimental procedures for verification of candidate biomarker molecules based on a lectin microarray.

Differential glycan profiling is performed using antibody-overlay lectin microarrays or the like for glycoproteins (AGP and M2BP) collected from the sera of (viral) hepatitis patients, cirrhosis patients, and hepatic cell carcinoma patients. First, blood samples are collected from (viral) hepatitis patients, chronic hepatitis patients, cirrhosis patients, and hepatic cell carcinoma patients. Each blood sample collected is subjected to immunoprecipitation using antibodies against AGP and M2BP, thereby performing concentration and purification. Then, it is confirmed whether the use as glycan-marker glycoproteins for clinical conditions of liver disease is possible using antibody-overlay lectin arrays. More specifically, as shown in FIG. 7, sera from patients with hepatitis viruses are subjected to differential glycan analysis for AGP and M2BP. AGP and M2BP are each simply enriched by an immunoprecipitation method using an anti-AGP antibody and an anti-M2BP antibody. A lectin microarray is a highly sensitive apparatus for differential glycan analysis. With such a lectin microarray, analysis can be sufficiently conducted with about 100 nanograms of a protein (prepared). Hence, the above pre-treatment can be performed on a small scale. Enriched AGP and M2BP are immediately added to a lectiri microarray. After a given reaction time, the sugar chain profiles of AGP and M2BP are obtained by an antibody-overlay lectin microarray method. At this time, the amount of a protein to be added to a lectin array differs depending on protein and ranges from about several nanogram to several tens of nanograms. Array analysis is conducted for a sufficient number of specimens to allow statistical analysis, and then 2-group comparison analysis (e.g., Student-T test) is conducted using the resulting data set. Therefore, objective selection of lectins (which can cause significant differences in signals resulting from changes in clinical conditions) becomes possible. As a lectin microarray, for example, a lectin microarray upon which a plurality of lectins including some or all of the lectins listed in Table 2 shown below have been immobilized can be used. More specifically, lectin microarrays described in the document of Kuno A., et al., Nat. Methods 2,851-856 (2005) or LecChip (GP Bioscience) can be used. As antibodies, antibodies listed in Table 1 can be used.

TABLE 1

| Glycoprotein name | Antibody (Bender, catalog No.) |
|---|---|
| alpha-1-acid glycoprotein (AGP) | mouse monoclonal, clone AGP-47 (Sigma, A5566) rabbit polyclonal (Rockland, 200-406-046) |
| Galectin 3 binding protein (Mac-2-binding protein, Mac2BP) | goat polyclonal (R&D Systems, AF2226) |

3-1. Lectin Microarray (also Simply Referred to as Lectin Array)

A lectin array is prepared by immobilizing (array formation) a plurality of types of discriminant (probe) lectin, which differ in specificity, on one substrate in parallel. With a lectin array, the types of lectin that interact with complex carbohydrates to be analyzed and the degrees of the interactions can be simultaneously analyzed. Moreover, with a lectin array, information required for glycan structure estimation can be obtained by a single analysis, and, steps from sample preparation to scanning can be rapidly and conveniently performed. Glycoproteins cannot be directly analyzed by a glycan profiling system such as mass spectroscopy. When such a system is employed, glycoproteins should be converted in advance to glycopeptides or free sugar chains. Meanwhile, a lectin microarray is advantageous in that direct analysis is possible with only the direct introduction of a fluorescence substance into a core protein portion, for example. Lectin microarray technology has been developed by the present inventors and the principle and the basic concept thereof are described in Kuno A., et al. Nat. Methods 2,851-856 (2005), for example.

Examples of lectins to be used for lectin arrays are as listed in Table 2 below.

TABLE 2

| | Lectins | Origin | Binding specificity (Sugar binding specificity) |
|---|---|---|---|
| 1 | LTL | *Lotus tetragonolobus* | Fuc$\alpha$1-3GlcNAc, Sia-Le$^x$ and Le$^x$ |
| 2 | PSA | *Pisum sativum* | Fuc$\alpha$1-6GlcNAc and $\alpha$-Man |
| 3 | LCA | *Lens culinaris* | Fuc$\alpha$1-6GlcNAc and $\alpha$-Man, $\alpha$-Glc |
| 4 | UEA-I | *Ulex europaeus* | Fuc$\alpha$1-2LacNAc |
| 5 | AOL | *Aspergillus oryzae* | Terminal $\alpha$Fuc and ±Sia-Le$^x$ |
| 6 | AAL | *Aleuria aurantia* | Terminal $\alpha$Fuc and ±Sia-Le$^x$ |
| 7 | MAL | *Maackia amurensis* | Sia$\alpha$ 2-3Gal |
| 8 | SNA | *Sambucus nigra* | Sia$\alpha$ 2-6Gal/GalNAc |

TABLE 2-continued

| | Lectins | Origin | Binding specificity (Sugar binding specificity) |
|---|---|---|---|
| 9 | SSA | Sambucus sieboldiana | Siaα 2-6Gal/GalNAc |
| 10 | TJA-I | Trichosanthes japonica | Siaα 2-6Galβ1-4GlcNAcβ-R |
| 11 | PHA(L) | Phaseolus vulgaris | Tri- and tetra-antennary complex oligosaccharides |
| 12 | ECA | Erythrina cristagalli | Lac/LacNAc |
| 13 | RCA120 | Ricinus communis | Lac/LacNAc |
| 14 | PHA(E) | Phaseolus vulgaris | NA2 and bisecting GlcNAc |
| 15 | DSA | Datura stramonium | $(GlcNAc)_n$, polyLacNAc and LacNAc (NA3, NA4) |
| 16 | GSL-II | Griffonia simplicifolia | Agalactosylated N-glycan |
| 17 | NPA | Narcissus pseudonarcissus | non-substituted α1-6Man |
| 18 | ConA | Canavalia ensiformis | α-Man (inhibited by presence of bisecting GlcNAc) |
| 19 | GNA | Galanthus nivalis | non-substituted α1-6Man |
| 20 | HHL | Hippeastrum hybrid | non-substituted α1-6Man |
| 21 | BPL | Bauhinia purpurea alba | Galβ1-3GalNAc and NA3, NA4 |
| 22 | TJA-II | Trichosanthes japonica | Fucα1-2Gal, β-GalNAc > NA3, NA4 |
| 23 | EEL | Euonymus europaeus | Galα1-3[Fucα1-2Gal] > Galα1-3Gal |
| 24 | ABA | Agaricus bisporus | Galβ1-3GalNAcα-Thr/Ser (T) and sialyl-T |
| 25 | LEL | Lycopersicon esculentum | $(GlcNAc)_n$ and polyLacNAc |
| 26 | STL | Solanum tuberosum | $(GlcNAc)_n$ and polyLacNAc |
| 27 | UDA | Urtica dioica | $(GlcNAc)_n$ and polyLacNAc |
| 28 | PWM | Phytolacca americana | $(GlcNAc)_n$ and polyLacNAc |
| 29 | Jacalin | Artocarpus integrifolia | Galβ1-3GalNAcα-Thr/Ser (T) and GalNAcα-Thr/Ser (Tn) |
| 30 | PNA | Arachis hypogaea | Galβ1-3GalNAcα-Thr/Ser (T) |
| 31 | WFA | Wisteria floribunda | Terminal GalNAc (e.g., GalNAcβ1-4GlcNAc) |
| 32 | ACA | Amaranthus caudatus | Galβ1-3GalNAcα-Thr/Ser (T) |
| 33 | MPA | Maclura pomifera | Galβ1-3GalNAcα-Thr/Ser (T) and GalNAcα-Thr/Ser (Tn) |
| 34 | HPA | Helix pomatia | Terminal GalNAc |
| 35 | VVA | Vicia villosa | α-, β-linked terminal GalNAc and GalNAcα-Thr/Ser (Tn) |
| 36 | DBA | Dolichos biflorus | GalNAcα-Thr/Ser (Tn) and GalNAcα1-3GalNAc |
| 37 | SBA | Glycine max | Terminal GalNAc (especially GalNAcα1-3Gal) |
| 38 | GSL-I mixture | Griffonia simplicifolia | α-GalNAc, GalNAcα-Thr/Ser (Tn), α-Gal |
| 39 | PTL-I | Psophocarpus tetragonolobus | α-GalNAc and Gal |
| 40 | MAH | Maackia amurensis | Siaα 2-3Galβ1-3[Siaα2-6GalNAc]α-R |
| 41 | WGA | Triticum unlgaris | (GlcNAc)n and multivalent Sia |
| 42 | GSL-IA$_4$ | Griffonia simplicifolia | α-GalNAc, GalNAcα-Thr/Ser (Tn) |
| 43 | GSL-IB$_4$ | Griffonia simplicifolia | α-Gal |

For example, a lectin array (LecChip (GP Bioscience)) on which 45 types of lectin have been immobilized on the base is already currently commercially available.

3-2. Statistical Analysis of Glycan Profiles Using Lectin Arrays

Lectin array technology has been currently developed to practical technology by which quantitative differential glycan profiling can be performed not only for purified samples, but also for mixed samples such as sera and cell lysates. In particular, differential glycan profiling of sugar chains on cell surface layers has been significantly developed (Ebe, Y. et al., J. Biochem. 139, 323-327 (2006), Pilobello, K. T. et al., Proc Natl Acad Sci U.S.A. 104, 11534-11539 (2007), Tateno, H. et al., Glycobiology 17, 1138-1146 (2007)).

Also, data mining of glycan profiles by statistical analysis can be performed by methods described in "Kuno A, et al. J Proteomics Bioinform. 1, 68-72 (2008)," "The Japanese Society of Carbohydrate Research, 2008/8/18 Development of Applied Technology of Lectin Microarray-Differential Glycan Profiling and Statistical Analysis of Biological Samples-Atsushi Kuno, Atsushi Matsuda, Yoko Itakura, Hideki Matsuzaki, Hisashi Narumatsu, and Jun Hirabayashi", and "Matsuda A, et al. Biochem Biophys Res Commun. 370, 259-263 (2008)," for example.

3-3. Antibody-overlay Lectin Microarray Method

A lectin microarray platform is basically as described above. The antibody-overlay lectin microarray method is an applied method that enables convenient, simultaneous, and high-speed analysis of multiple analytes upon detection not by directly labeling analytes with fluorescence or the like, but by indirectly introducing a fluorescent group or the like via an antibody into analytes ("Kuno A, Kato Y, Matsuda A, Kaneko M K, Ito H, Amano K, Chiba Y, Narimatsu H, Hirabayashi J. Mol Cell Proteomics. 8, 99-108 (2009))," "Jun Hirabayashi, Atsushi Kuno, and Noboru Uchiyama, "Development of Applied Technology of Glycan Profiling using Lectin Microarray," "Approach from Molecular Level, Cancer Diagnosis and Research -Challenge to Clinical Application- (Extra Number, Experimental Medicine), YODOSHA, Vol. 25 (17) 164-171 (2007)," "Application of Glycan Profiling System using Lectin Microarray to Search for Glycan marker (Atsushi Kuno and Jun Hirabayashi)," and "Development of Clinical Glycan marker and Elucidation of Sugar Chain Functions (see Gene and Medicien, Mook No. 11, pp. 34-39, Medical Do (2008)).

When glycoproteins (AGP and M2BP) are analytes, sugar chain (glycan) portions are recognized by lectins on a lectin microarray. Antibodies (anti-AGP antibody and anti-M2BP antibody) against core protein portions are overlaid thereon, so that the glycoproteins to be tested can be specifically detected with high sensitivity without labeling or high-level precise purification thereof.

3-4. Lectin-overlay Antibody Microarray Method

The lectin-overlay antibody microarray method involves the use of an antibody microarray instead of a lectin microarray, which is prepared by immobilizing in parallel (array formation) an antibody against a core protein on a substrate such as a glass substrate. The number of antibodies corresponding to the number of markers to be examined is required for the method. It is also required to confirm in advance lectins for detection of glyco-alterations.

4. Method for Detecting Liver Disease Using Disease-Specific Glyco-alterations in Glycan Marker as an Index for Clinical Conditions of Liver Disease AGP and M2BP are novel glycan markers as indices for clinical conditions of liver disease, which is characterized in that the glycan structures are altered in association with clinical changes in liver disease such as the progress of fiber formation. Accordingly, a lectin (hereinafter, abbreviated as lectin "A"), the reactivity of which is altered in response to changes in the glycan structures of AGP and M2BP is reacted with markers contained in a sample collected from a subject, and then markers that have reacted with the lectin are measured. Thus, the clinical conditions of liver disease can be identified and the degree of fiber formation in the liver can be determined, for example.

For example, novel glycan markers as indices for clinical conditions of liver disease can be detected using:

(1) (i) the above lectin "A"; and (ii) an antibody for detection of a core protein portion other than the sugar chain of the above marker. Novel glycan markers as indices for clinical conditions of liver disease can also be detected using: (2) antibodies that are specific to glycan markers as indices for clinical conditions of liver disease, the epitope of which is a part containing a sugar-chain-binding portion.

For example, markers are detected using antibodies against the core proteins of markers and lectin "A", so that liver disease patients can be distinguished from healthy subjects and detected. Preferably, an antibody overlay method using lectin array ("Kuno A, Kato Y, Matsuda A, Kaneko M K, Ito H, Amano K, Chiba Y, Narimatsu H, Hirabayashi J. Mol Cell Proteomics. 8, 99-108 (2009)) can be used. When one, two, or more optimum lectins "A" are selected for the test for verification of disease-specific glyco-alterations in 3, it is more preferable to use a $1^{st}$ or $2^{nd}$ rapid measurement method (described later).

A specific example of the method for examining liver disease using novel glycan markers as indices for clinical conditions of liver disease is a method for detecting liver disease comprising the steps of:

1) measuring glycan markers as indices for clinical conditions of liver disease, which have sugar chains specifically reacting with lectin "A" in a sample collected from a subject;

2) measuring glycan markers as indices for clinical conditions of liver disease, which have sugar chains specifically reacting with lectin "A" in a sample collected from a healthy subject;

3) measuring glycan markers as indices for clinical conditions of liver disease, which have sugar chains specifically reacting with lectin "A" in a sample collected from a liver disease patient; and 4) comparing the measurement results for glycan markers as indices for clinical conditions of liver disease obtained from the subject with the measurement results for glycan markers as indices for clinical conditions of liver disease obtained from the healthy subject or the liver disease patient, and then determining that the subject has liver disease when the measurement results for the subject are closer to the measurement results for the liver disease patient.

A threshold is also determined in advance for distinguishing liver disease from the other diseases based on the measurement results for many liver disease patients and healthy subjects, and then the measurement results for the subject are compared with the threshold, so as to determine whether or not the subject is affected by liver disease.

4-1. Method for Measuring the Progress of Fiber Formation

It is known that regarding the progress of hepatitis due to hepatitis viral infection, the degree of fiber formation correlates with liver dysfunction and a risk of hepatic cell carcinoma. Therefore, the measurement of fiber formation refers to evaluation of liver dysfunction and a risk of cancer. Also, about 40% of all the hepatitis patients does not react to interferon treatment, so that viral infection persists. It is considered that whether or not these clinical conditions progress to an active mode should be determined based on the progress of fiber formation. Based on these viewpoints, measurement of the progress of fiber formation is significant for diagnostic treatment for hepatitis.

Fiber formation is currently evaluated based on pathological diagnosis on biopsy samples. In recent years, the widespread use of the method is expected as a result of introduction of Fibroscan. Also, as methods for serological evaluation of fiber formation, Fibro Test, Forn's index, Hepatoscore, and the like are clinically used, but these methods are inferior to biopsy diagnosis in terms of both sensitivity and specificity.

AGP and M2BP are subjected to the antibody-overlay lectin microarray method using a group of patients' sera differing in the degree of the progress of fiber formation, so that lectins that exhibit increased or decreased signal intensity in correlation with the degree of the progress of fiber formation are selected. Based on the information, a sandwich detection method using an antibody against a candidate marker molecule and lectin "A" exhibiting changes in signals due to the progress of fiber formation can be established, such as lectin-antibody sandwich ELISA or an antibody-overlay lectin microarray method. About 100 patients' sera (100 serum samples) subjected in advance to the staging of fiber formation by pathological diagnosis are collected and then subjected to analysis. A cut off value at each stage is then determined, so that the progress of fiber formation in the liver can be monitored using the serum sample from each patient.

An example of lectin "A" is, in the case of AGP, a first lectin selected from AOL and MAL and an example of lectin "A" in the case of M2BP is a second lectin selected from WFA, BPL, AAL, RCA120, and TJAII. Hereinafter, such a lectin selected from AOL and MAL may be referred to as a "first lectin," and such a lectin selected from WFA, BPL, AAL, RCA120, and TJAII may be referred to as a "second lectin."

For example, AGP binding to a first lectin can be measured using a first lectin array to which at least the first lectin has been immobilized and an anti-AGP antibody; and M2BP binding to a second lectin can be measured using a second lectin array to which at least the second lectin has been immobilized and an anti-M2BP antibody.

4-2. Detection of Cirrhosis

Cirrhosis is defined as clinical conditions in which regenerating nodules losing hepatic lobule structures and fine fibrous diffuse connective tissues appear throughout the liver, surrounding such regenerating nodules. This is also a terminal status of progressive chronic liver disease with persistent damage to hepatocytes and fiber formation. Liver biopsy to be performed in cirrhosis is intended to perform component diagnosis. In the cases of early cirrhosis or cirrhosis with a macronodular pattern, many cases are diagnosed with difficulties (Surgical Pathology, Fourth ed., Bunkodo Co., Ltd.). Therefore, test techniques with which cirrhosis can be qualitatively and quantitatively diagnosed are required. For the purpose, candidate antibody molecules capable of monitoring the progress of fiber formation and a lectin set, found in the section, "1) Method for measuring the progress of fiber formation" can be used for detection of cirrhosis if the fiber formation stages, F3 and F4, can be distinguished from each other.

4-3. Detection of Disease-specific Glyco-alterations on Novel Glycan Markers as Indices for Clinical Conditions of Liver Disease in a Sample Examples of a sample include, biopsy tissue samples, body fluid samples, and a preferable example of the same is blood (e.g., serum and blood plasma).

The term "measurement" refers to both qualitative measurement, and quantitative measurement.

Measurement of glycan markers as indices for clinical conditions of liver disease can be performed using (1) a column or an array to which lectin "A" has been immobilized and (2) an antibody against AGP or M2BP, for example. Preferably, an antibody-overlay lectin array method, and more preferably a $1^{st}$ or $2^{nd}$ rapid measurement method can be used.

The concentration of AGP or M2BP can also be measured. Examples of a method to be used therefor include an antibody-overlay lectin array method using a lectin array, immunoassay, an enzyme activity determination method, and a capillary electrophoresis method. Preferably, the following qualitative or quantitative techniques can be used, such as enzyme immunoassay, double-antibody sandwich ELISA, a gold colloid method, radioimmunoassay, enzyme chemiluminescence immunoassay, electric chemiluminescence immunoassay, latex agglutination immunoassay, fluorescence immunoassay, a Western blotting method, an immunohistochemical method, and a surface plasmon resonance method (hereinafter, referred to as an SPR method) using lectin "A" most reflecting disease-specific glyco-alterations, which is statistically selected with an antibody-overlay lectin array, and a monoclonal antibody or a polyclonal antibody specific to AGP or M2BP.

Further specifically, sub determination can also be performed by a Western blotting method using lectin "A" and antibodies against glycan markers as indices for clinical conditions of a disease. The above expression "when the measurement results for a subject are higher than . . . " in qualitative determination refers to a case in which novel glycan markers as indices for clinical conditions of a disease are qualitatively demonstrated to be present in a sample from a subject with higher concentrations than those in a sample from a healthy subject. Furthermore, a lectin method as a direct sugar chain measurement method without mediation of an antibody is also included herein.

Examples of lectin "A" the reactivity of which is altered in response to changes (accompanying the progress of fiber formation in the liver) in the AGP glycan structure include AOL and MAL or a combined use of AOL and MAL, which are strictly selected by statistical analysis after an antibody-overlay lectin array method. AOL is a lectin that exhibits the highest significant difference among a group of lectins, the reactivity of which to AGP sugar chain increases with the progress of fiber formation in the liver. MAL is a lectin exhibits the most significant differences among a group of lectins, the reactivity of which to AGP sugar chain decreases with the progress of fiber formation in the liver. Accordingly, the use of both measured value of AGP binding to AOL and measured value of AGP binding to MAL makes it possible to more precisely distinguish the clinical conditions of the liver disease of a subject. As a method that involves the use of both the measured value of AGP binding to AOL (measured value of AOL) and the measured value of AGP (measured value of MAL) binding to MAL, a known statistical technique can be employed. For convenience, a difference between and the ratio of AOL measurement value and/to MAL measurement value can be used. In addition, when a difference between or the ratio of AOL measurement value and/to MAL measurement value is used, the same scale is preferably employed for both measured values for convenience, a difference between the cut off line values of both measured values is found and then the scales can be corrected. For example, the ratio of MAL cut-off line value to AOL cut-off line value is used and then either AOL measurement value or MAL measurement value may be corrected. AGP contained in a sample collected from a subject using AOL and/or MAL is measured, so that AGP can be used as a marker for identifying fiber formation in the liver, a cirrhosis detection marker, or a hepatic cell carcinoma detection marker. Also, AGP in a sample collected from a patient under treatment using interferon or the like is measured using the lectin "A," so that the therapeutic effect can be monitored.

In addition, the measured values of AGP binding to AOL or MAL are preferably normalized using the measured value of AGP binding to lectins the reactivity of which substantially remains unchanged regardless of changes in AGP glycan structure. As such a lectin, DSA is preferable. Also, measured values of AGP binding to AOL or MAL can be normalized using the measured value of AGP core protein contained in a sample collected from a subject. Also, in a method that involves the use of both AOL measurement value and MAL measurement value, a normalized AOL measurement value and a normalized MAL measurement value are preferably used. For example, with the use of the above first lectin array and the above second lectin array, which are prepared by further immobilizing DSA, AGP binding to DSA is measured, measured values of AGP binding to a first lectin are normalized using measured values of AGP binding to DSA, M2BP binding to DSA is measured, the measured values of M2BP binding to a second lectin are normalized using the measured value of M2BP binding to DSA, and thus AGP and/or M2BP can be measured. Examples of lectin "A," the reactivity of which is altered in response to changes in M2BP glycan structure accompanying changes in the clinical conditions of the liver, include WFA, BPL, AAL, RCA120, and/or TJAII strictly selected by statistical analysis after the antibody-overlay lectin array method. WFA, BPL, AAL, RCA120, and TJAII are all lectins, the reactivity of which to M2BP sugar chain increases as the clinical conditions of liver disease progress. WFA, BPL, and TJAII that are strongly reactive to M2BP of hepatic cell carcinoma patients, and particularly of cases of post-operative cancer recurrence. M2BP contained in a sample collected from a subject is measured using WFA, BPL and/or TJAII, so that M2BP can be used as a marker for discriminating a group of patients with a high risk of hepatic cell carcinoma. Also, M2BP contained in a sample collected from a subject is measured using AAL and/or RCA120, so that M2BP can be used as a marker for identifying fiber formation in the liver, a cirrhosis detection marker, or a hepatic cell carcinoma detection marker. Also, WFA is periodically used for a patient after extraction of hepatic cell carcinoma and then M2BP in a sample collected from the patient is measured, so that a risk of recurrence can be predicted. In addition, there are very few molecules capable of binding to WFA in glycoproteins contained in serum, thereby enabling the direct use of serum as a measurement sample. WFA is preferable since the degree of freedom resulting from the use of WFA is high upon construction of a measurement system.

In addition, the measured values of M2BP binding to WFA, BPL, AAL, RCA120, or TAJII are preferably normalized using the measured value of M2BP binding to a lectin the reactivity of which substantially remains unchanged regardless of changes in M2BP glycan structure. As such a lectin, DSA is preferable. Also, the measured values of M2BP binding to WFA, BPL, AAL, RCA120, or TAJII may be normalized using the measured value of M2BP core protein contained in a sample collected from a subject.

Measurement of AGP binding to AOL, MAL, or DSA and measurement of M2BP binding to WFA, BPL, AAL, RCA120, or TAJII are preferably performed by the antibody-overlay lectin microarray method. In particular, the antibody-overlay lectin microarray method is capable of simultaneously measuring AGP or M2BP binding to a plurality of types of lectin. Also, when markers such as AGP and M2BP are rapidly measured using lectin "A," measurement is preferably performed by the following $1^{st}$ or $2^{nd}$ rapid measurement method.

An example of the 1st rapid measurement method is a method for quantitatively determining AGP reacting with the above lectin "A" by mixing biotinylated lectin "A" prepared by binding biotin to lectin "A" with a sample, adding magnetic particles to which streptavidin has been immobilized to the mixture, so as to form a magnetic particle-lectin "A"-AGP complex, reacting the complex with a labeled anti-AGP antibody, so as to form a $2^{nd}$ complex of magnetic particle-lectin "A"-AGP-labeled anti-AGP antibody, and then measuring the amount of the label of the 2nd complex. In addition, M2BP can be measured in a manner similar to that in the above method for measuring AGP except for the use of a labeled anti-M2BP antibody. With the 1st rapid measurement method, AGP or M2BP in a sample can be quantitatively determined within about 60 minutes. With the use of biotinylated lectin "A" and streptavidin-immobilized magnetic particles, the reactivity of lectin "A" to AGP or M2BP in a sample can be improved and the reaction time of lectin "A" with AGP or M2BP can be shortened to about 30 minutes.

Furthermore, an example of the $2^{nd}$ rapid measurement method is a method for quantitatively determining AGP reacting with lectin "A" by mixing magnetic particles to which lectin "A" has been immobilized with a sample, capturing AGP sugar chains in the sample using lectin "A," reacting AGP captured by the magnetic particles with a labeled anti-AGP antibody, so as to form a magnetic particle-lectin "A"-AGP-labeled anti-AGP antibody complex, and then measuring the amount of the label of the complex. Also with the $2^{nd}$ rapid measurement method, M2BP can be measured in a manner similar to the above method for measuring AGP except for the use of a labeled anti-M2BP antibody. With the $2^{nd}$ rapid measurement method, AGP or M2BP in a sample can be quantitatively determined within about 20 minutes. Specifically with the use of lectin "A"-immobilized magnetic particles, the reactivity of lectin "A" to AGP or M2BP in a sample is significantly improved and thus the reaction time of lectin "A" with AGP or M2BP can be shortened to about 5 minutes.

The $1^{st}$ and the $2^{nd}$ rapid measurement methods are suitable for automation. In particular, the $2^{nd}$ rapid measurement method can be appropriately performed with full automatic measuring equipment. Automation of the 2nd rapid measurement method makes it possible to easily perform consecutive measurement of multiple specimens. Also, automation makes it possible to perform measurement of a single specimen for multi test items (measurements using different lectins) within a short period of time.

As labels for labeled anti-AGP antibodies or labeled anti-M2BP antibodies, fluorescent substances or enzymes can be used. Examples of a fluorescent substance include fluorescein isothiocyanate (FITC), a green fluorescent protein (GFP), and luciferin. Examples of an enzyme include alkaline phosphatase (ALP), peroxidase, glucose oxidase, tyrosinase, and acid phosphatase. When alkaline phosphatase is used as an enzyme, a known luminescent substrate, a known chromogenic substrate, and the like can be used. Examples thereof include chemiluminescent substrates such as CDP-star (registered trademark)(4-chloro-3-(methoxyspiro{1,2-dioxetane-3,2'-(5'-chloro)tricyclo[3.3.1.13,7]decane}-4-yl)phenylphosphate disodium), and CSPD (registered trademark) (3-(4-methoxyspiro{1,2-dioxetane-3,2-(5'-chloro)tricyclo [3.3.1.13,7]decane}-4-yl)phenylphosphate disodium), and chromogenic substrates such as p-nitrophenyl phosphate, 5-bromo-4-chloro-3-indolyl-phosphoric acid (BCIP), 4-nitroblue tetrazolium chloride (NBT), and iodonitrotetrazolium (INT). Furthermore, an antibody is labeled with biotin, and then the above fluorescent substance to which streptavidin has been bound or the above enzyme may be bound to the antibody via biotin-avidin binding.

A blood sample contains a trace amount of AGP or M2BP having glycan structural changes due to fiber formation in the liver. Hence, it is preferable to use an enzyme as a label and a luminescent substrate in view of high sensitivity and more rapid detection of the label.

In addition, an enzyme such as ALP has sugar chains. Hence, a deglycosylated enzyme is preferably used to prevent a nonspecific reaction between the sugar chains and a lectin. As such a deglycosylated enzyme, deglycosylated ALP can be used, such as Recombinant AP, EIA Drade, and CR 03535452 (Roche Diagnostics).

Also, an anti-AGP antibody or an anti-M2BP antibody also has sugar chains. Hence, a deglycosylated antibody is preferably used to prevent a nonspecific reaction between sugar chains and lectins. For example, an anti-AGP antibody or an anti-M2BP antibody converted to Fab' as a result of pepsin digestion and reduction is preferably used.

A labeled antibody reagent is prepared as follows. According to a known method, an anti-AGP antibody or an anti-M2BP antibody is mixed with a maleimidized label using a cross-linking agent such as EMCS [N-(6-Maleimidocaproyloxy)succinimido] (DOJINDO LABORATORIES) for reaction, so that a labeled antibody can be prepared. For example, deglycosylated ALP is maleimidized using a cross-linking agent, followed by reaction with an anti-AGP antibody or an anti-M2BP antibody converted to Fab'. The use of the thus prepared antibody is preferable in view of prevention of nonspecific reaction.

5. Novel Specific Polyclonal Antibodies and/or Monoclonal Antibodies Using Novel Glycan Markers as Indices for Clinical Conditions of Liver Disease In the method for detecting hepatic cell carcinoma using novel glycan markers as indices for clinical conditions of liver disease, when a polyclonal antibody and/or a monoclonal antibody specific to glycan markers as indices for clinical conditions of liver disease can be easily obtained, these antibodies can be used. However, when the antibodies cannot be easily obtained, they can be prepared as follows, for example.

5-1. Preparation of Antibodies

The novel glycan markers as indices for clinical conditions of liver disease of the present invention can be used for preparing a polyclonal antibody or a monoclonal antibody for detection of liver disease.

For example, antibodies against novel glycan markers as indices for clinical conditions of liver disease can be prepared by a known method. Freund's complete adjuvant is administered at the same time, so that the generation of an antibody can be boosted. Also, a peptide including a binding position to which sugar chain X has bound is synthesized, the peptide is covalently bound to commercially available keyhole limpet hemocyanin (KLH), and then the conjugate is administered to an animal. In addition, a granulocyte-macrophage colony stimulating factor (GM-CSF) is administered at the same time, so that antibody production can be boosted.

Also, for example, monoclonal antibodies against novel glycan markers as indices for clinical conditions of liver disease can be prepared by the methods of Keller and Milstein (Nature Vol. 256, pp. 495-497 (1975)). For example, a hybridoma is prepared by cell fusion of antibody-producing cells obtained from an animal immunized with an antigen with myeloma cells, and then clones producing an anti-X antibody are selected from the thus obtained hybridoma.

Specifically, an adjuvant is added to the thus obtained glycan markers as indices for clinical conditions of liver disease for antigens. Examples of an adjuvant include Freund's complete adjuvant and Freund's incomplete adjuvant. Any of these adjuvants may be mixed.

An antigen obtained as described above is administered to a mammal such as a mouse, a rat, a horse, a monkey, a rabbit, a goat, or sheep. Any immunization method can be employed herein, as long as it is an existing method. Immunization is mainly performed by intravenous injection, subcutaneous injection, intraperitoneal injection, or the like. Also, the immunization interval is not particularly limited and immunization is performed at intervals of several days to several weeks and preferably at intervals of 4 to 21 days.

On days 2 to 3 after the final immunization date, antibody-producing cells are collected. Examples of antibody-producing cells include spleen cells, lymph node cells, and peripheral blood cells.

As myeloma cells to be fused to antibody-producing cells, cells of established cell lines from various animals (e.g., mice, rats, and humans), which are generally available for persons skilled in the art, are used. Cell lines to be used herein have properties such that they have drug resistance and are unable to survive in an unfused state, but are able to survive only in a fused state in a selective medium (e.g., HAT medium). In general, an 8-azaguanine-resistant strain is used. This cell line is deficient in hypoxanthine-guanine-phosphoribosyl-transferase and is unablb to grow in a hypoxanthine.aminopterin.thymidine (HAT) medium.

Myeloma cells of various known cell lines are appropriately used, such as P3 (P3x63Ag8.653) (J. Immunol. 123, 1548-1550 (1979)), P3x63Ag8U.1 (Current Topics in Microbiology and Immunology 81, 1-7 (1978)), NS-1 (Kohler, G. and Milstein, C., Eur. J. Immunol. 6, 511-519 (1976)), MPC-11 (Margulies, D. H. et al., Cell 8, 405-415 (1976)), SP2/0 (Shulman, M. et al., Nature 276,269-270 (1978)), FO (de St. Groth, S. F. et al., J. Immunol. Methods 35, 1-21 (1980)), S194 (Trowbridge, I. S., J. Exp. Med. 148, 313-323 (1978)), and 8210 (Galfre, G. et al., Nature 277, 131-133 (1979)).

Next, the above myeloma cells are fused to antibody-producing cells. Cell fusion is performed by bringing myeloma cells into contact with antibody-producing cells at a mixture ratio ranging from 1:1 to 1:10 in the presence of a fusion accelerator at 30° C. to 37° C. for 1 to 15 minutes in a medium for culturing animal cells, such as MEM, DMEM, or RPME-1640 medium. A fusion accelerator with an average molecular weight between 1,000 and 6,000 such as polyethylene glycol or polyvinyl alcohol, or a fusion virus such as Sendai virus can be used for acceleration of cell fusion. Also, antibody-producing cells can also be fused to myeloma cells using a commercially available cell fusion apparatus using electrical stimulation (e.g., electroporation).

A hybridoma of interest is selected from cells after cell fusion. An example of a method for selection is a method using selective growth of cells in a selective medium. Specifically, cell suspension is diluted with an appropriate medium and then spread over a microtiter plate. A selective medium (e.g., HAT medium) is added to each well, and then cells are cultured while appropriately exchanging selective media. As a result, cells that have grown can be obtained as hybridoma cells.

Screening for a hybridoma is performed by limiting dilution, a fluorescence excitation cell sorter method, or the like, and then finally a monoclonal-antibody-producing hybridoma is obtained. Examples of a method for collecting a monoclonal antibody from the thus obtained hybridoma include a general cell culture method and a method for forming ascites.

Also, an antibody to be used in the present invention may be a monoclonal antibody or a polyclonal antibody. Examples of such an antibody include single-chain Fvs (scFv), a single-chain antibody, a Fab fragment, a F(ab') fragment, and disulfide linkage Fvs (sdFv). Furthermore, as an antibody to be used in not only the or the $2^{nd}$ rapid measurement method, but also the present invention, a deglycosylated antibody is preferably used to prevent a nonspecific reaction between a sugar chain and a lectin. For example, an anti-AGP antibody or an anti-M2BP antibody converted to Fab' as a result of pepsin digestion and reduction can be used.

EXAMPLES

Example 1

Use of Glycan-marker Glycoproteins as Indices for Clinical Conditions of Liver Disease for Detection of Liver Disease Liver disease was detected by antibody-overlay lectin array performed for glycan-marker glycoproteins as indices for clinical conditions of liver disease, AGP and Mac2BP (M2BP), as follows. In addition, FIG. 7 shows the procedures of this technique for differential analysis of sugar chains on the marker glycoproteins derived from the sera of (viral) hepatitis patients (CH), cirrhosis patients (LC), hepatic cell carcinoma patients (HCC), and healthy subjects (HV).

1. Enrichment of Marker Proteins from Serum

Enrichment of the marker glycoproteins derived from the sera of (viral) hepatitis patients (CH), cirrhosis patients (LC), hepatic cell carcinoma patients (HCC), and healthy subjects (HV) was performed according to "Kuno A, Kato Y, Matsuda A, Kaneko M K, Ito H, Amano K, Chiba Y, Narimatsu H, Hirabayashi J. Mol Cell Proteomics. 8, 99-108 (2009)." In addition, five cases each were used for analysis of each clinical condition in order to clarify the dependence of the obtained results on clinical conditions. Each patient's serum was diluted 10-fold with a 0.2% SDS-containing PBS buffer and then heated for 10 minutes at 95° C. Five (5) μL of the resultant was dispensed in the case of AGP and 20 μL of the same was dispensed in the case of Mac2BP to reaction tubes, and then 500 ng of an antibody (biotinylated antibody) against each antigen was added to the reaction tubes. Each reaction solution was adjusted with a reaction buffer (1% Triton X-100-containing Tris-buffered saline (TBSTx)) to 45 μL, followed by 2 hours of shaking reaction at 4° C. Immediately after antigen-antibody reaction, 5 μL (corresponding to 10 μL of the original beads solution) of a solution of magnetic beads with streptavidin immobilized thereto (Dynabeads MyOne Streptavidin T1, DYNAL Biotech ASA), which had been washed 3 times in advance with a reaction buffer and then concentrated 2-fold for adjustment, was added to the above reaction solution, followed by further 1 hour of reaction. As a result of the reaction, the glycoproteins formed complexes with magnetic beads via the biotinylated antibody. The complexes were adsorbed to magnet for recovery of magnetic beads and then the solution was discarded. The thus recovered complexes were washed 3 times with 500 μL of a reaction buffer and then suspended in 10 μL of an elution buffer (0.2% SDS-containing TBS). The suspension solution was heated at 95° C. for 5 minutes, so as to dissociate and elute the glycoproteins from magnetic beads. The thus obtained solution was designated an eluate. At this time, heat-denatured biotin antibodies are also mixed thereinto. Hence, 10 μL (corresponding to 20 μl of the original beads solution) of a magnetic beads solution that had been concentrated 2-fold for adjustment by the above-mentioned technique was added to the eluate, followed by 1 hour of reaction. Thus, adsorption removal of biotinylated antibodies was performed. The thus obtained solution was designated as a serum-derived glycoprotein solution and used for the following experiments.

2. Antibody-overlay Lectin Array

An appropriate amount of the above-obtained glycoprotein solution was adjusted with a lectin array reaction buffer (1% Triton X-100-containing phosphate-buffered saline (PBSTx)) to 60 μL. The solution was added to each reaction vessel (8 reaction vessels were formed per glass slide) for a lectin microarray, followed by 10 or more hours of reaction at 20° C. The lectin microarray base comprising 8 reaction vessels was prepared according to the techniques of Uchiyama et al., (Proteomics 8, 3042-3050 (2008)). Thus, a binding reaction between sugar chains on the glycoproteins and 43 types of lectin immobilized on the array substrate reached an equilibrium state. Subsequently, to prevent sugar chains on antibodies for detection from binding to unreacted lectins on the base, so as to generate noise, 2 μL of a human serum-derived IgG solution (Sigma) was added and then reaction was performed for 30 minutes. Each reaction vessel was washed 3 times with 60 μL of PBSTx and then 2 μL of a human serum-derived IgG solution was added again. After slight stirring, a 100 ng equivalent of an antibody (biotinylated antibody for detection) against each glycoprotein to be detected, was added to the solution, followed by 1 hour of reaction at 20° C. After antigen-antibody reaction, each reaction vessel was washed 3 times with 60 μL of PBSTx, and then a PBSTx solution containing a 200 ng equivalent of Cy3-labeled streptavidin was added, followed by further 30 minutes of reaction at 20° C. After reaction, each reaction vessel was washed 3 times with 60 μL of PBSTx, and then array scanning was performed using an array scanner GlycoStation (MORITEX Corporation).

Figure 8:
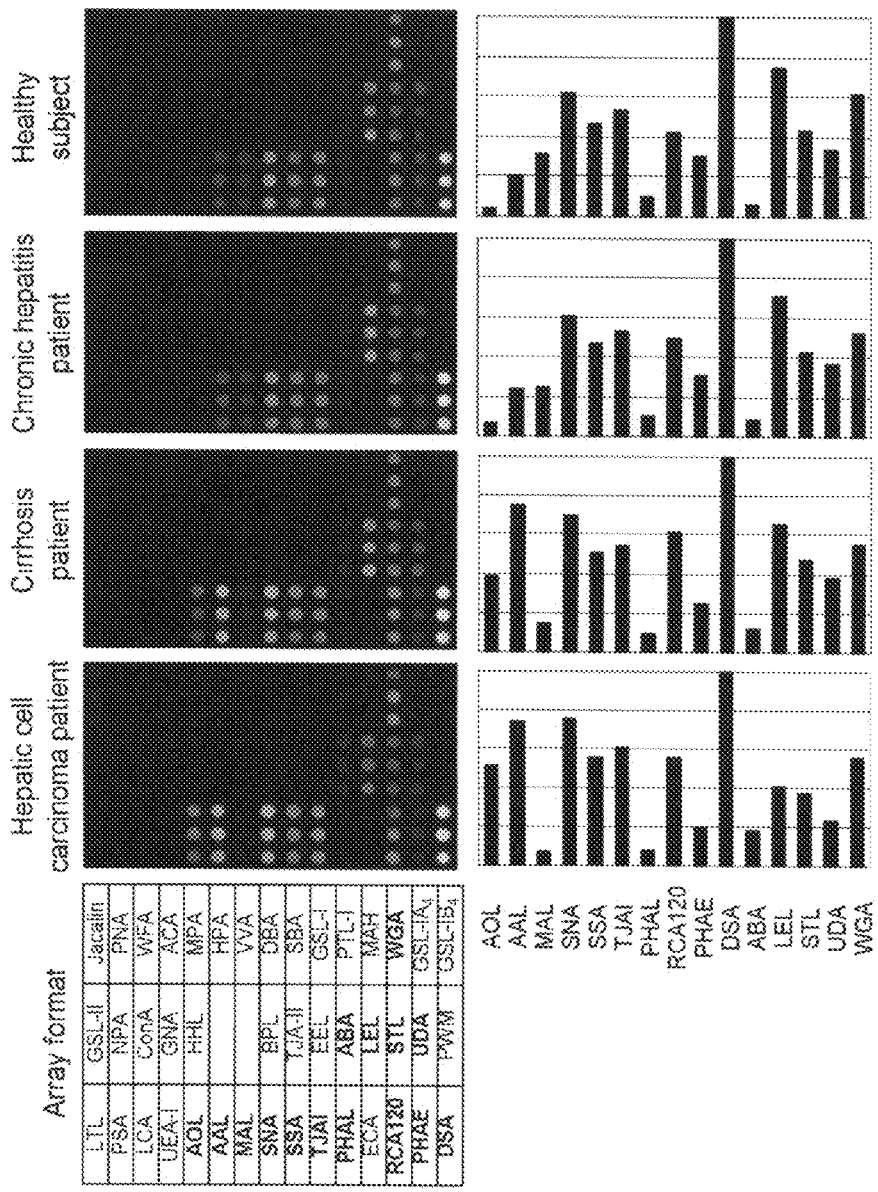
FIG. 8 shows the results of conducting differential glycan analysis for a1 acid glycoprotein (AGP) that is one of marker glycoproteins as indices for clinical conditions of liver disease using antibody-overlay lectin microarray.
Figure 9:
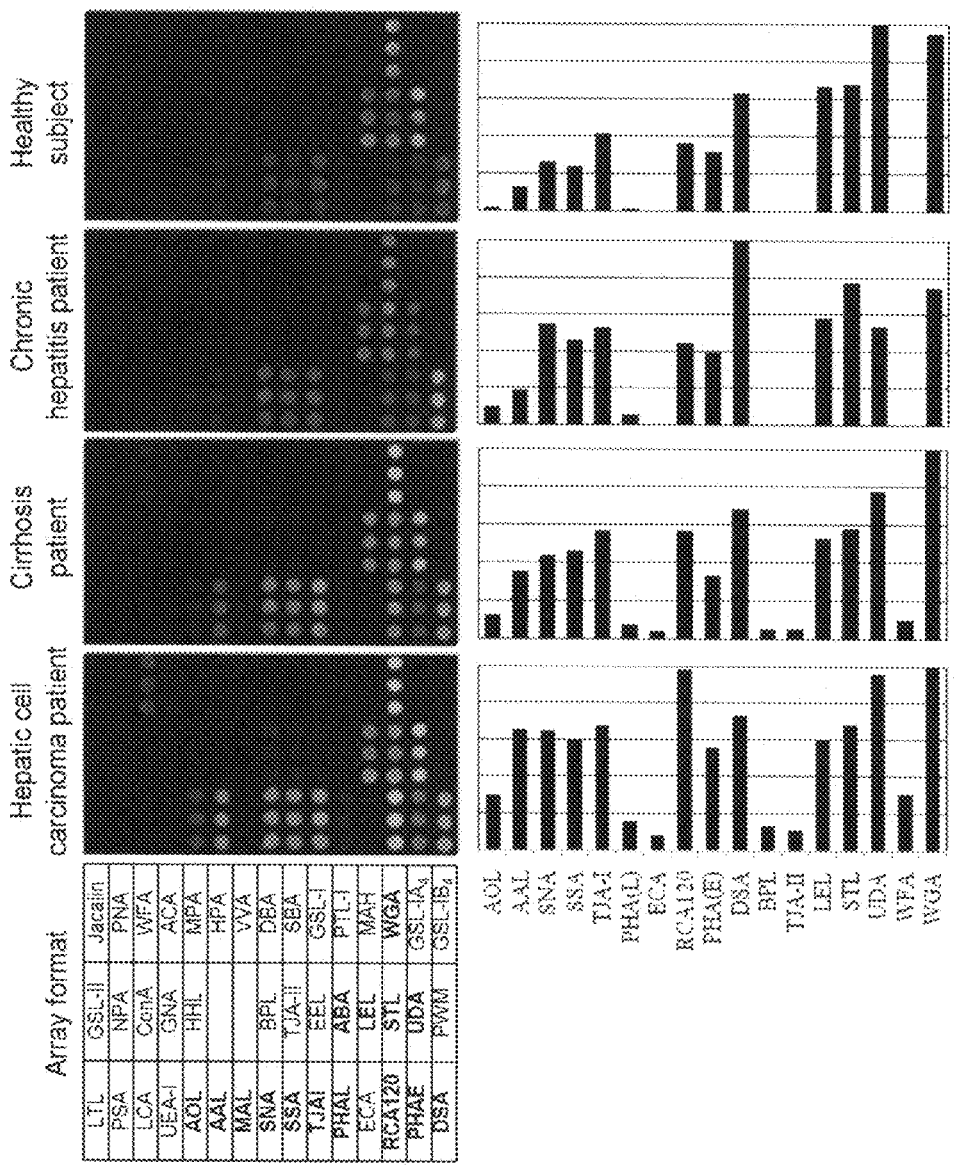
FIG. 9 shows the results of conducting differential glycan analysis for 90K/Mac-2 Binding Protein (M2BP) that is one of marker glycoproteins as indices for clinical conditions of liver disease using an antibody-overlay lectin microarray.

Of the thus obtained results, a typical example of each clinical condition resulting from the use of AGP is shown in FIG. 8 and the same resulting from the use of Mac2BP is shown in FIG. 9. FIG. 8 shows the results of conducting differential glycan analysis for α1 acid glycoprotein (AGP) that is one of marker glycoproteins as indices for clinical conditions of liver disease by antibody-overlay lectin microarray. Arrangement of lectins (array format) on the lectin microarray is shown on the left in the upper portion of FIG. 8. Lectins for which significant signals were obtained by this experiment are indicated by boldface. Signals were obtained for 15 types of lectin. Typical scan images of AGP derived from sera of hepatic cell carcinoma, cirrhosis, and chronic hepatitis patients, and healthy subjects are shown on the right in the upper portion of FIG. 8. Numerical conversion of each signal was performed using array analysis software from scan data. The results for 15 types of lectin represented by graphs are shown in the lower portion of FIG. 8. It is clearly understood that differences in signal pattern arose between hepatic cell carcinoma and cirrhosis groups and hepatitis and healthy subject groups. FIG. 9 shows the results of conducting differential glycan analysis for 90K/Mac-2 Binding Protein (M2BP) that is one of marker glycoproteins as indices for clinical conditions of liver disease by antibody-overlay lectin microarray. Lectin arrangement on the lectin microarray is shown on the left in the upper portion of FIG. 9. Lectins for which significant signals were obtained by this experiment are indicated by boldface. Signals were obtained for 17 types of lectin. Typical scan images of M2BP derived from sera of hepatic cell carcinoma, cirrhosis, and chronic hepatitis patients, and healthy subjects are shown on the right in the upper portion of FIG. 9. Numerical conversion of each signal was performed using array analysis software from scan data. The results for 17 types of lectin represented by graphs are shown in lower portion of FIG. 9. It is understood that changes (increases or decreases) in signal intensity occurred depending on severity of clinical conditions.

Example 2

Identification of the Progress of Fiber Formation in the Liver by Antibody-overlay Lectin Array Analysis of AGP Glycan-marker Glycoprotein as an Index for Clinical Conditions of Liver Disease As shown in Example 1, glycoproteins were chosen by statistical analysis from the lectin signal information obtained by the antibody-overlay lectin array analysis of glycoproteins. The use of the thus selected optimum glycoprotein leads to the possibility of detecting liver disease with each type of clinical condition.

Accordingly, an experiment was conducted with the following procedures using AGP as a target molecule.

1. Narrowing Down the Number of Lectins for Distinguishing Between Cirrhosis and Hepatitis To narrow down the number of lectin groups exhibiting signal fluctuations with the progress of fiber formation, firstly antibody-overlay lectin array analysis was conducted for AGP using sera of clinically diagnosed HCC, LC, and CH patients (10 cases each). To perform more objective narrowing down, Student T test was performed for HCC-LC and LC-CH. Lectins with a risk of 0.1% or less were designated as useful lectins. The results are shown in Table 3. As understood from the previous experimental results (FIG. 8), as a result of the AGP array analysis, signals were obtained for 15 types of lectin, and 6 types of lectin (LEL, AOL, AAL, MAL, STL, and PHAE) out of the 15 types exhibited significant differences (risk of 0.1% or less as a Student T test result). In this experiment, lectin DSA exhibited the fewest signal fluctuations, but it also exhibited high reproducibility. Regarding the lectin DSA, we found effectiveness in the normalization of the thus obtained data and determined that after scanning, all data subjected to numerical conversion had been normalized with DSA signals.

TABLE 3

| CV(average) | Net intensity (0.53) T-test (P) | | After DSA nomalization (0.49) T-test (P) | |
|---|---|---|---|---|
| Lectin | HCC-CH | LC-CH | HCC-CH | LC-CH |
| LEL | 2.60E−10 | 7.30E−06 | 3.20E−16 | 1.70E−08 |
| AOL | 4.70E−08 | 7.40E−09 | 1.50E−07 | 1.10E−07 |
| AAL | 6.50E−08 | 1.20E−07 | 1.00E−07 | 1.20E−07 |
| MAL | 1.10E−07 | 1.60E−04 | 1.30E−07 | 1.70E−04 |
| STL | 4.30E−07 | 2.00E−04 | 5.30E−11 | 3.10E−07 |
| PHAE | 1.20E−04 | 8.80E−05 | 2.90E−05 | 2.40E−05 |
| ABA | 5.60E−01 | 2.00E−02 | 5.60E−01 | 2.40E−03 |
| PHAL | 1.90E−03 | 4.40E−02 | 1.40E−03 | 2.30E−02 |
| SSA | 2.80E−02 | 2.00E−02 | 3.50E−04 | 1.50E−06 |
| RCA120 | 1.70E−01 | 3.20E−02 | 7.60E−02 | 3.70E−04 |
| WGA | 5.20E−02 | 2.50E−02 | 5.20E−03 | 3.50E−02 |
| SNA | 1.60E−01 | 1.30E−01 | 4.60E−02 | 3.30E−03 |
| UDA | 4.40E−01 | 8.70E−01 | 5.00E−01 | 6.80E−01 |
| DSA | 9.70E−01 | 7.10E−01 | — | — |
| TJAI | 9.10E−01 | 8.50E−01 | 9.30E−01 | 6.70E−01 |

2. Narrowing Down of the Number of Lectins for Identifying the Progress of Fiber Formation Next, antibody-overlay lectin microarray was performed for 125 cases of a group of patients infected by hepatitis virus and pathologically diagnosed by liver biopsy for staging of fiber formation according to the procedures of Example 1. In addition, the results of staging for fiber formation in the liver in 125 cases are as follows: F0 and F1 (33 cases), F2 (32 cases), F3 (31 cases), and F4 (29 cases). According to the above procedures, lectins statistically useful for identification were narrowed down. As a result, the results for top 6 types of lectin are shown in Table 4. The thus obtained 6 lectins ranked high and particularly LEL, AOL, and MAL were selected as the most effective lectins for identification. Hence, detailed data analysis was conducted for the 3 types of lectin.

TABLE 4

| N = 125 | T-test (P) | |
|---|---|---|
| Lectin | F0-3 vs F4 | F3 vs F4 |
| LEL | 1.74E−16 | 2.53E−08 |
| AOL | 8.37E−16 | 5.30E−05 |
| AAL | 1.98E−13 | 3.46E−04 |
| MAL | 2.83E−14 | 8.05E−06 |
| STL | 1.41E−06 | 5.79E−04 |
| PHAE | 1.18E−12 | 2.36E−04 |

Figure 10:
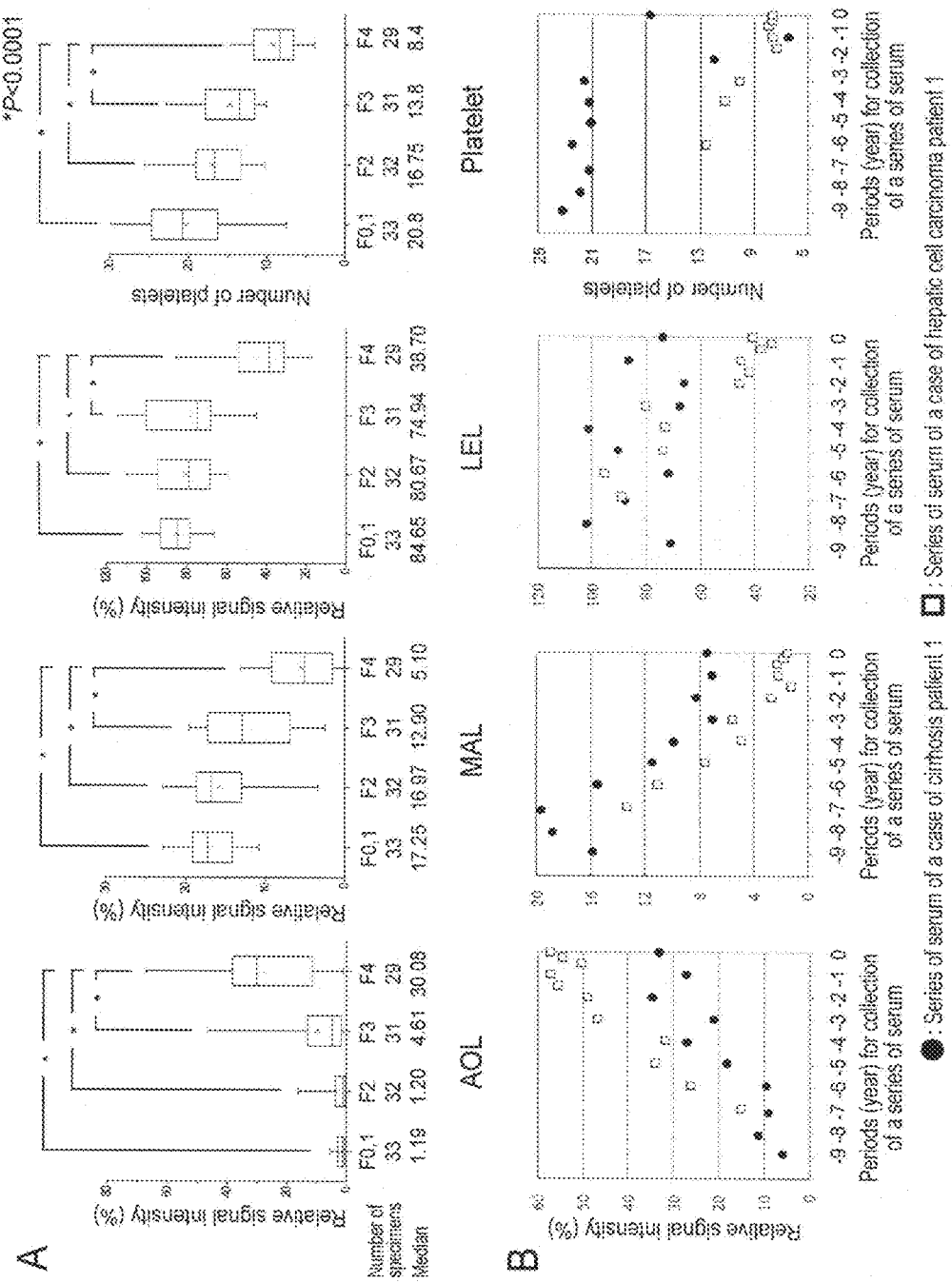
FIGS. 10A and 10B show the correlations between the progress of fiber formation in the liver and changes in lectin signal intensity obtained by antibody-overlay lectin array analysis of AGP.

FIG. 10 shows the correlations between the progress of fiber formation in the liver and changes in lectin signal intensity obtained by antibody-overlay lectin array analysis of AGP. Each signal was normalized with the signal of DSA lectin and a numerical value is expressed as relative signal intensity when the DSA signals are designated as 100%. The results shown in A in the upper portion of FIG. 10 were obtained by performing lectin array analysis for 125 cases for which staging (F) of fiber formation had been performed by pathological analysis after liver biopsy. The distribution of the lectin signal at each stage is shown with a box-whisker plot. The upper end and the lower end of each box indicate a point of 75% and a point of 25%, respectively. The upper end and the lower end of each whisker indicate a point of 95% and a point of 5%, respectively. A transverse line in each box indicates the median value and "x" indicates the average value. Student-T test was performed to test significant differences between cirrhosis (F4) and chronic hepatitis (at stage F0, 1, 2or 3). Each result with a risk of P<0.0001 is indicated with *. Also as a control, the distribution of numerical values for blood platelets, which is used as an index for fiber formation in the liver upon general biochemical examination. As a result, the intensity of AOL signal increased with the progress of fiber formation. It was demonstrated that chronic hepatitis (F0-3) and cirrhosis (F4) can be sufficiently distinguished from each other based on differences in intensity. On the other hand, it was revealed that the intensities of MAL and LEL signals decreased with the progress of fiber formation.

The results of measuring with time AOL, MAL, and LEL signal fluctuations in the same patient are shown in B in the lower portion of FIG. 10. Antibody-overlay lectin microarray analysis was conducted for AGP in a series of specimens (serum samples collected at different times) from a single case of a cirrhosis patient or a hepatic cell carcinoma patient, and then the relative signal values of AOL, MAL, and LEL after normalization with DSA signals were plotted in B in the lower portion of FIG. 10. The time axis was set so that the date of the definitive diagnosis of cirrhosis and hepatic cell carcinoma was designated as "day 0." The intensity of AOL signal increased with time and that of MAL signal decreased with time, leading to the reflection of the progress of fiber formation in the liver. On the other hand, the intensity of LEL signals or the number of blood platelets, which is used as a simple fiber formation marker, exhibited rapid fluctuations at certain times, and did not clearly express the progress of fiber formation.

It was demonstrated by the above results that the independent use of or a combined use of AOL and MAL signal fluctuations makes it possible to identify the progress of fiber formation in the liver.

Example 3

Detection of Cirrhosis by Antibody-overlay Lectin Array Analysis for AGP Glycan-marker Glycoprotein as an Index for Clinical Conditions of Liver Disease It was considered based on the results of Example 2 that determination of a cut-off value of each lectin (signals) or a combination of lectin signals on the basis of the progress of fiber formation in the liver enables detection of cirrhosis. Hence, an experiment was conducted with the following procedures.

1. Determination of Lectin Signal—Cut-off Values for Detection of Cirrhosis

Figure 11:
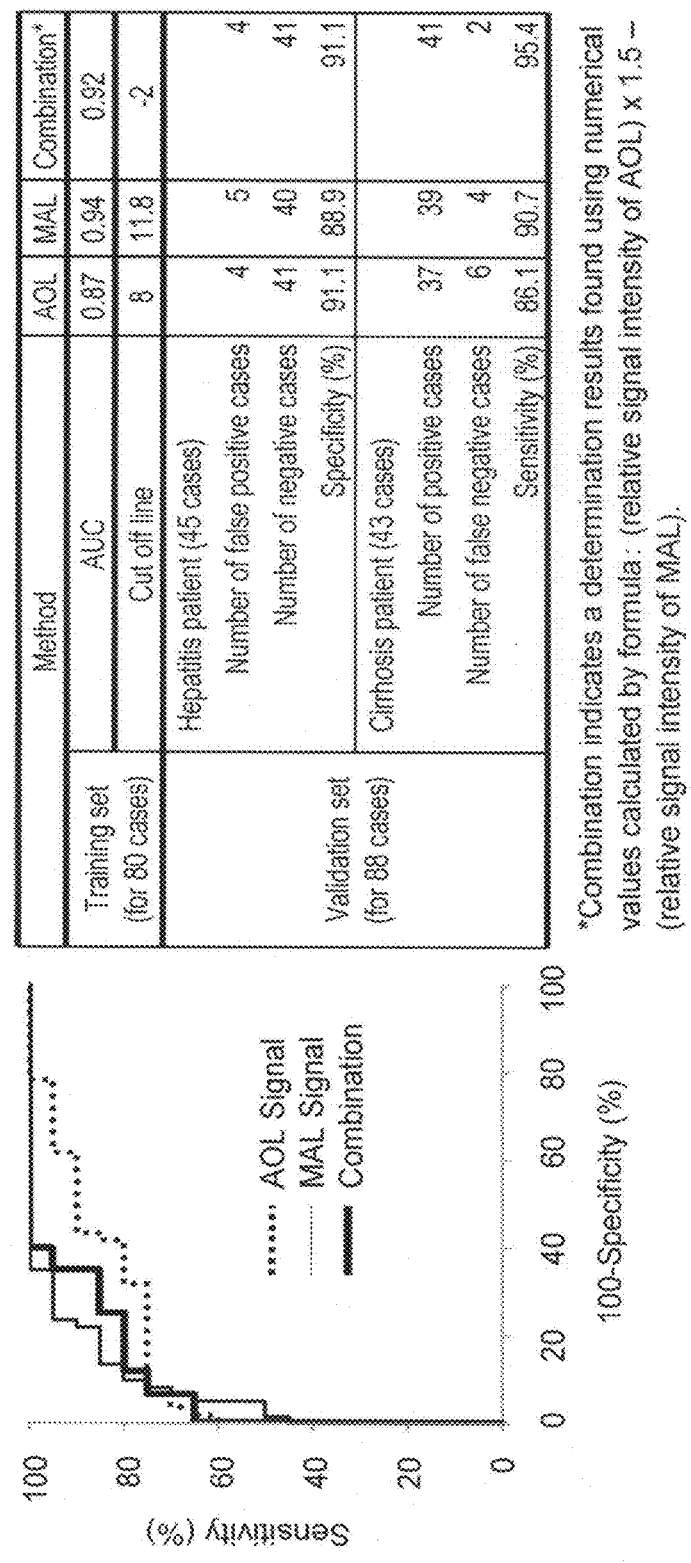
FIG. 11 shows detection schemes for cirrhosis by antibody-overlay lectin microarray analysis of AGP that is a glycan marker as an index for clinical conditions of liver disease.

First, a cut-off value was determined for each lectin in order to detect a patient with cirrhosis from among patients infected by hepatitis virus. For this purpose, a receiver operating characteristic curve (ROC curve) for distinguishing F4 (cirrhosis) from the other stages (F1-F3) was created for 80 cases of pathologically diagnosed patients (F1, F2, F3, and F4 (20 cases each)) with the use of data obtained by normalization of 2 types of lectin signal narrowed down in Example 2 with DSA lectin signals. The results are shown on the left in FIG. 11. FIG. 11 shows, in addition to a curve of a case in which AOL signal or MAL signal was independently used, a curve representing numerical values obtained by an equation (relative signal intensity of AOL)×1.5−(relative signal intensity of MAL), in which 2 signals were used. AUC (area under curve) values representing the area of the lower part under curve were found, so as to assess the diagnostic ability of each technique. Also, a point on a curve, which is located closest to the point of 100% sensitivity and the point of 100% specificity, in other words, a contact point between a line parallel to the line of Y=X and the ROC curve, was designated as "optimum specificity and sensitivity" and in the periphery cut-off values were determined. These numerical values are shown in the right table in FIG. 11. With the use of the thus obtained cut-off values, a blind test was performed for 45 cases and 43 cases of patients definitively diagnosed as having hepatitis and cirrhosis by pathological diagnosis or diagnostic imaging—clinical diagnosis. The results are shown in the column of "Validation set" in the right table in FIG. 11. Cirrhosis was determined to be positive and hepatitis was determined to be negative, and the detected number thereof is listed in the table. On the basis of the ROC curve, each cut-off value was determined at a point where the best sensitivity and the best specificity were exhibited. The cut-off values were 8% in the case of AOL and 11.8% in the case of MAL. Also, in the combination system, the fewest number of false-negative patients and the fewest number of false-positive patients were confirmed and the accuracy (%) ((total number of patients−(the number of false-positive and false-negative patients))/(total number of patients)×100) was high.

2. Detection of Cirrhosis

Antibody-overlay lectin array was performed for 45 cases of clinically diagnosed chronic hepatitis patients and 43 cases of clinically diagnosed cirrhosis patients according to the procedures in Example 2 using AGP as a target molecule. All signals were normalized with the signal of DSA lectin, which had been designated as 100%. The numerical values were determined to be positive or negative using the above-mentioned cut-off values, so that cirrhosis detection was tested. As a result, when AOL signals were used, the detection ability was represented by the sensitivity of 86.1%, the specificity of 91.1%, and the accuracy of 88.6%. When MAL signals were used, the detection ability was represented by the sensitivity of 90.7%, the specificity of 88.9%, and the accuracy of 89.8%. Significantly high-level detection was possible in both cases, such that the accuracy exceeded 85%. Moreover, the detection ability was examined using an equation with a combined use of two signals ((relative signal intensity of AOL)×1.5−(relative signal intensity of MAL)). Thus, the most reliable cirrhosis detection result was obtained, such that the sensitivity was 95.4%, the specificity was 91.1%, and the accuracy was 93.2%. It is particularly worth noting that the detection ability was overwhelmingly higher than those of known techniques for detection of disease-specific glycoalterations in AGP using AAL lectin or RCA lectin. These results agree with the result of the narrowing-down step using antibody-overlay lectin array in which AAL and RCA120 were inferior to AOL and MAL (see Table 3 and Table 4).

Example 4

Figure 12:
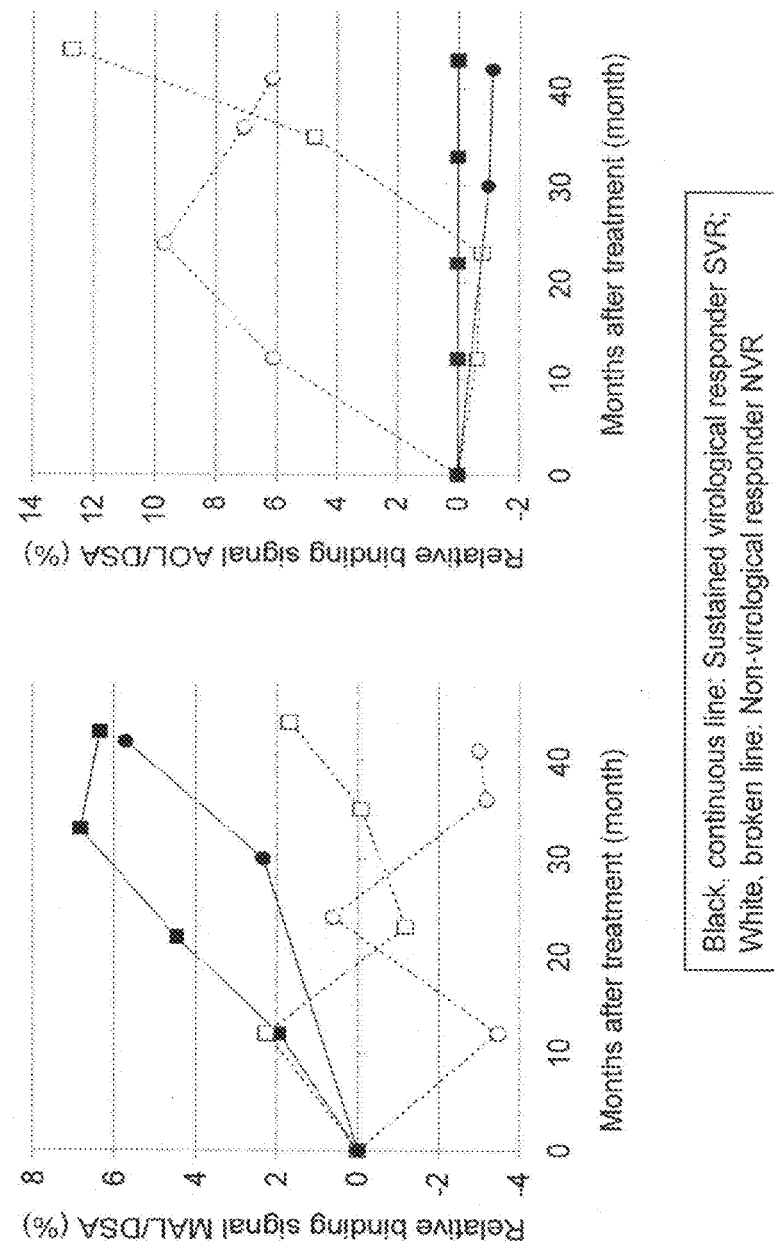
FIG. 12 shows the determination of therapeutic effects of interferon using AGP as a marker capable of monitoring the progress of fiber formation in the liver.

Determination of Therapeutic Effects of an Interferon Using a Marker Capable of Monitoring the Progress of Fiber Formation in the Liver It was demonstrated based on the results of Example 2 that the progress of fiber formation can be monitored through observation of AOL and MAL signal fluctuations. Hence, the therapeutic effects of an interferon that is an antiviral agent were experimentally determined using AOL/DSA or MAL/DSA as a parameter indicating the progress of fiber formation. The following experiment was conducted for type C hepatitis patients of a sustained virological responder (SVR) group for which the therapeutic effects of the interferon had been confirmed and a non-virological responder (NVR) group for which no therapeutic effect thereof had been confirmed. After interferon treatment, patients' sera from blood collected with time were subjected to enrichment of AGP in serum and antibody-overlay lectin microarray analysis by techniques similar to those in Example 1. After normalization with DSA signals, relative signal values of AOL and MAL were calculated. The time course changes in each signal (typical results of the SVR group and the NVR group (2 cases each)) are shown in FIG. 12. The time axis was set so that the date of blood collection immediately after treatment was designated as "day 0." Regarding relative binding signals, the relative value immediately after treatment was designated as "0." In the SVR cases, MAL signals increased with time, but AOL signals decreased or no AOL signal was detected. Specifically, in these cases, fiber formation tended to be alleviated. On the other hand, in NVR cases, AOL signals increased with time and MAL signals remained almost unchanged. Specifically, in these cases, a tendency was observed such that fiber formation was not alleviated but rather worsened (e.g., fiber formation progressed). As described above, it was revealed that the effects after interferon treatment can be determined by a blood test.

Example 5

1. 1st Rapid Measurement Method (Manual Method)

1-1. Preparation of Reagent

Preparation of R1 reagent: R1 reagent 1 was prepared by adding 5 µg/mL biotinylated DSA (J-OIL MILLS, INC.) to buffer A (PBS-1% TritonX, pH7.4). R1 reagent 2 was prepared by adding 5 µg/mL biotinylated MAL (Vector) to buffer A. R1 reagent 3 was prepared by adding 2.5 µg/mL biotinylated AOL to buffer A. In addition, biotinylated AOL used herein was prepared by biotinylation of AOL (Tokyo Kasei Kogyo Co., Ltd.) using a biotin labeling kit (DOJIDO).

Preparation of R2 reagent: An R2 reagent was prepared by adding magnetic particles (number average particle size: 2 µm) to which streptavidin had been immobilized to buffer A to 0.5 w/v %.

Preparation of R3 reagent: A solution containing a 0.025 U/mL ALP-labeled mouse anti-AGP monoclonal antibody, 0.1 M MES (2-(N-Morpholino)ethanesulfonic acid, pH6.5), 0.15 M sodium chloride, 1 mM magnesium chloride, 0.1 mM zinc chloride, 0.1 w/v % $NaN_3$, and 0.5 w/v % casein Na was prepared and then designated as R3 reagent 1. R3 reagent 2 was prepared in a manner similar to that for R3 reagent 1 except for the use of a 0.5 U/mL ALP-labeled mouse anti-AGP monoclonal antibody instead of a 0.025 U/mL ALP-labeled mouse anti-AGP monoclonal antibody.

Preparation of R4 reagent: A solution containing 0.1 M 2-amino-2-methyl-1-propanol (AMP, pH 9.6), 1 mM magnesium chloride, and 0.1 w/v % $NaN_3$ was prepared and then designated as an R4 reagent.

Preparation of R5 reagent: CDP-Star with Sapphirine-II (luminescent substrate for ALP, Applied Biosystems) was designated as an R5 reagent.

Preparation of washing reagent: A solution containing 20 mM tris (pH7.4), 0.1 w/v % Tween20, 0.1 w/v % $NaN_3$, and 0.8 w/v % sodium chloride was prepared, and then designated as a washing reagent.

1-2. Confirmation of Dilution Linearity of DSA

AGP in Consera (normal human serum, Nissui Pharmaceutical Co., Ltd.) was recovered in buffer B (TBS-0.5% TritonX-0.1% SDS) using an anti-AGP antibody in a manner similar to that for enrichment in Example 1 and then used as a sample. The thus recovered sample was diluted 1-fold, ½-fold, ¼-fold, ⅛-fold, and 1/16-fold, respectively, with buffer B so that diluted samples were prepared.

Figure 13:
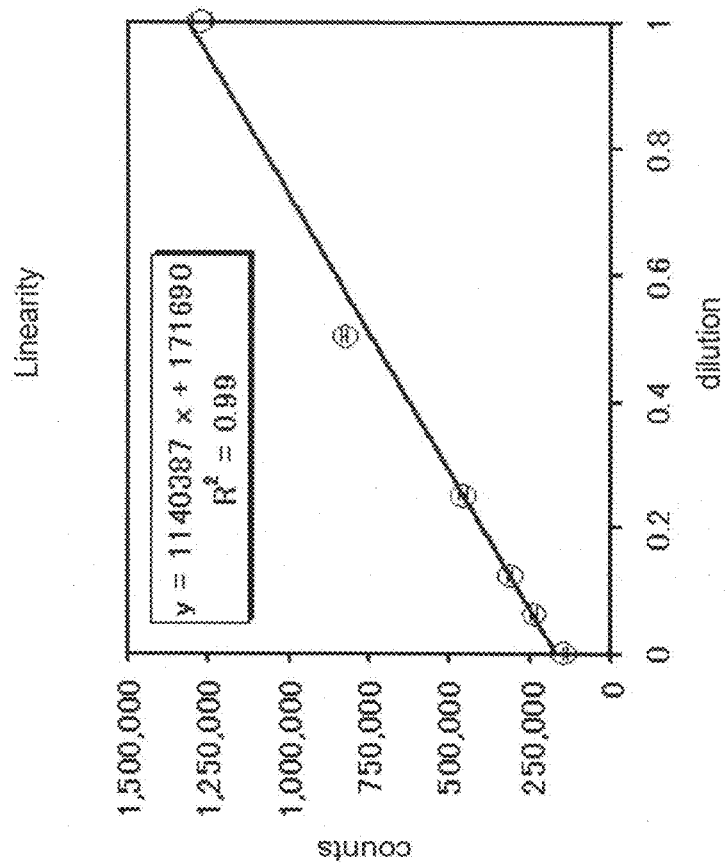
FIG. 13 shows dilution linearity when DSA was used in a $1^{st}$ rapid measurement method.

R1 reagent 1 (110 μL) was added to 30 μL of each diluted sample. After 2 minutes of reaction at room temperature, 30 μL of the R2 reagent was added and then reaction was performed for 30 minutes at room temperature. Magnetic particles bearing the complex of DSA and AGP were collected for B/F separation, the separated magnetic particles were washed using a washing reagent, and then the solution was discarded. This treatment was performed 4 times. R3 reagent 1 (100 μL) was added to the washed magnetic particles, followed by 20 minutes of reaction at room temperature, so that AGP in the complex on magnetic particles was reacted with the ALP-labeled mouse anti-AGP monoclonal antibody. Collected magnetic particles bearing the complex of the ALP-labeled mouse anti-AGP monoclonal antibody, AGP, and DSA were subjected to the removal of liquid components (B/F separation), the thus separated magnetic particles were washed with a washing reagent, and then the solution was discarded. This treatment was performed 4 times. Complex-bearing magnetic particles were dispersed in 50 μL of the R4 reagent, 100 μL of the R5 reagent was added, and then chemiluminescence intensity due to ALP was measured as a photo count value using a luminescence measurement apparatus. The results are shown in FIG. 13. As shown in FIG. 13, good linearity, $R^2=0.99$, was exhibited in the DSA measurement system.

1-3. Confirmation of Dilution Linearity of MAL

Figure 14:
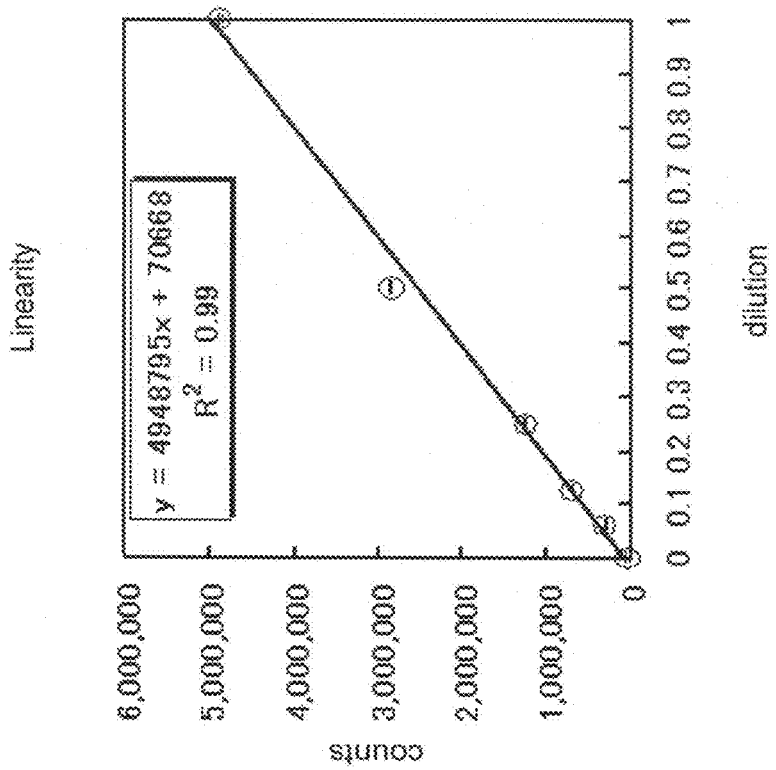
FIG. 14 shows dilution linearity when MAL was used in the $1^{st}$ rapid measurement method.

An experiment was conducted for confirmation of dilution linearity in a MAL measurement system in a manner similar to that in "confirmation of dilution linearity of DSA" except for the use of R1 reagent 2 instead of R1 reagent 1 and the use of R3 reagent 2 instead of R3 reagent 1. The results are shown in FIG. 14. As shown in FIG. 14, good linearity, $R^2=0.99$, was exhibited in the MAL measurement system.

1-4. Confirmation of Dilution Linearity of AOL

Figure 15:
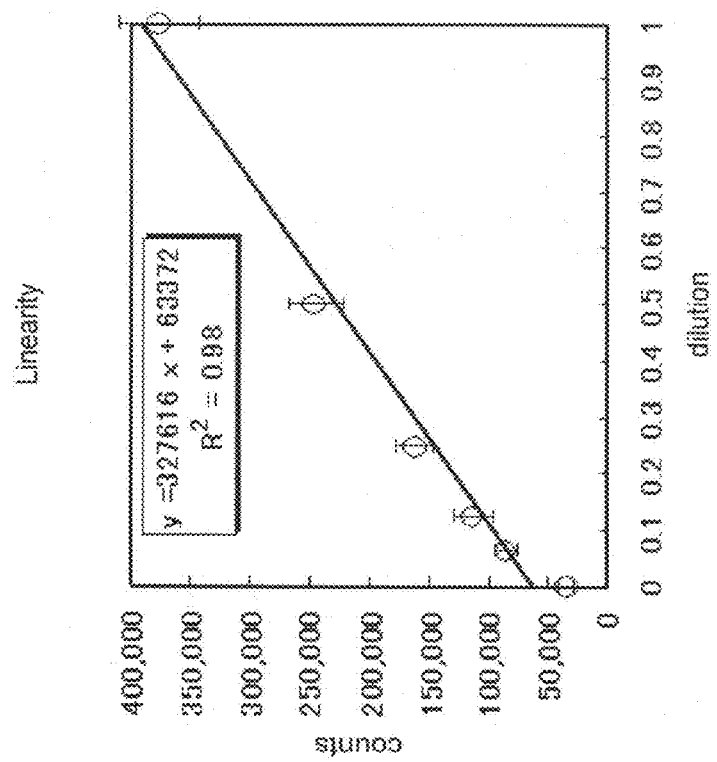
FIG. 15 shows dilution linearity when AOL was used in the $1^{st}$ rapid measurement method.

An experiment was conducted for confirmation of dilution linearity in an AOL measurement system in a manner similar to that in "confirmation of dilution linearity of DSA" except for the use of HCV-positive blood plasma 2 (Millenium Biotech) instead of Consera and the use of R1 reagent 3 instead of R1 reagent 1. The results are shown in FIG. 3. As shown in FIG. 15, good linearity, $R^2=0.98$, was exhibited in the AOL measurement system.

1-5. Measurement of DSA, MAL, and AOL for Various Commercially Available Specimens Consera (normal human serum, Nissui Pharmaceutical Co., Ltd.), normal human serum (TRINA), and HCV-positive blood plasma 1 and 2 (Millenium Biotech) were each subjected to AGP separation using an anti-AGP antibody in a manner similar to that for enrichment in Example 1. The resultants were then each recovered in a buffer (TBS-0.5% TritonX-0.1% SDS) and then used as samples for measurement. Also, a buffer alone was used as a sample (NC) for blank measurement.

R1 reagent 1 (110 μL) was added to 30 μL of each measurement sample. After 2 minutes of reaction at room temperature, 30 μL of the R2 reagent was added and then reaction was performed at room temperature for 30 minutes. Magnetic particles bearing the complex of DSA and AGP were collected for B/F separation, the separated magnetic particles were washed with a washing reagent, and then the solution was discarded. This treatment was performed 4 times. R3 reagent 1 (100 μL) was added to the washed magnetic particles, reaction was performed at room temperature for 20 minutes, and then AGP in the complex on magnetic particles was reacted with the ALP-labeled mouse anti-AGP monoclonal antibody. Magnetic particles bearing the complex of the ALP-labeled mouse anti-AGP monoclonal antibody, AGP, and DSA were collected for B/F separation, the separated magnetic particles were washed with a washing reagent, and then the solution was discarded. This treatment was performed 4 times. Complex-bearing magnetic particles were dispersed in 50 μL of the R4 reagent and then 100 μL of the R5 reagent was added. Chemiluminescence intensity in the DSA measurement system was measured as a photo count value using a luminescence measurement apparatus. The time required for measurement was 65 minutes. Measurement results are shown in Table 5.

Figure 16:
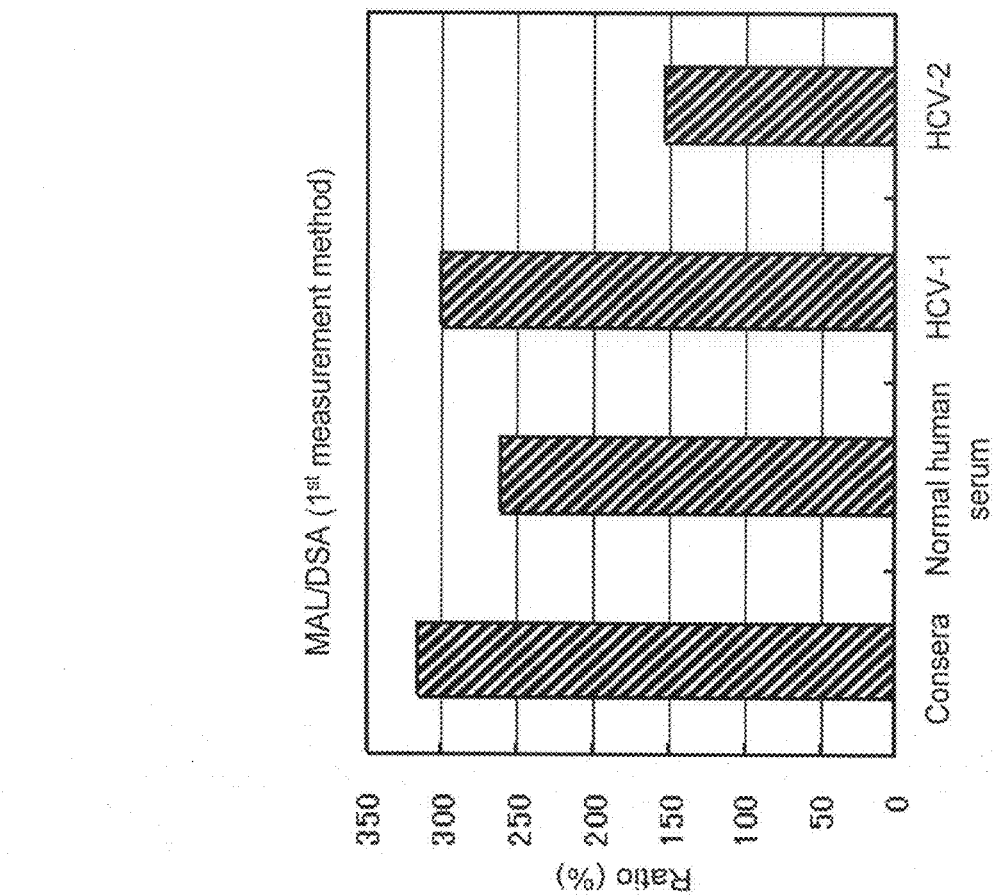
FIG. 16 shows measurement results when MAL was used for commercial specimens in the 1st rapid measurement method.
Figure 17:
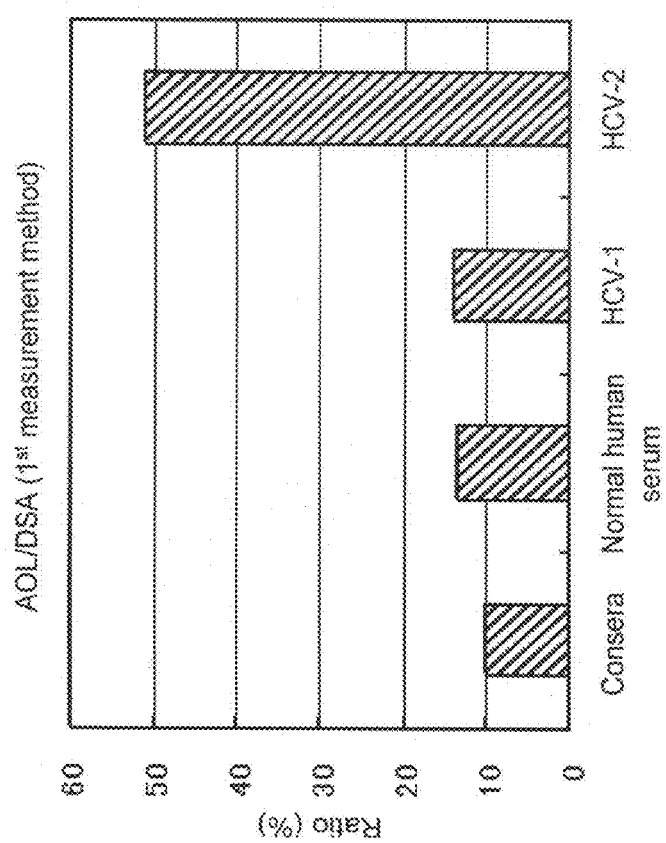
FIG. 17 shows measurement results when AOL was used for commercial specimens in the 1st rapid measurement method.

Also, chemiluminescence in the MAL measurement system was measured in a manner similar to that in the DSA measurement system except for the use of R1 reagent 2 instead of R1 reagent 1 and the use of R3 reagent 3 instead of R3 reagent 1. The results are shown in Table 5. Also, chemiluminescence in the AOL measurement system was measured in a manner similar to that in the DSA measurement system except for the use of R1 reagent 3 instead of R1 reagent 1. The results are shown in Table 5. Also, measurement results obtained using MAL and AOL are normalized with the measurement result obtained using DSA and then the thus obtained values are shown in Table 5, in addition to FIG. 16 and FIG. 17.

TABLE 5

|  | DSA | MAL | AOL | MAL/DSA | AOL/DSA |
|---|---|---|---|---|---|
| NC | 134464 | 4591 | 39520 | | |
| Consera | 947041 | 2566153 | 122283 | 315.24 | 10.19 |
| Normal human serum | 920232 | 2057193 | 145020 | 261.22 | 13.43 |
| HCV-1 | 1154871 | 3063570 | 181898 | 299.78 | 13.95 |
| HCV-2 | 848290 | 1093355 | 404969 | 152.53 | 51.20 |

1-6. Measurement by a Lectin Array Method for Various Commercially Available Specimens Each measurement sample in the above 1-5 was subjected to measurement by an antibody overlay method using lectin arrays used in Example 1. The time for measurement required by the lectin arrays method was about 18 hours. The results are shown in Table 6, in addition to FIG. 18 and FIG. 19.

TABLE 6

| Measurement results by lectin array | | |
|---|---|---|
|  | MAL/DSA | AOL/DSA |
| Consera | 15.4 | 2.8 |
| Normal human serum | 11 | 4.7 |
| HCV-1 | 15.2 | 4 |
| HCV-2 | 5.4 | 15.4 |

Figure 18:
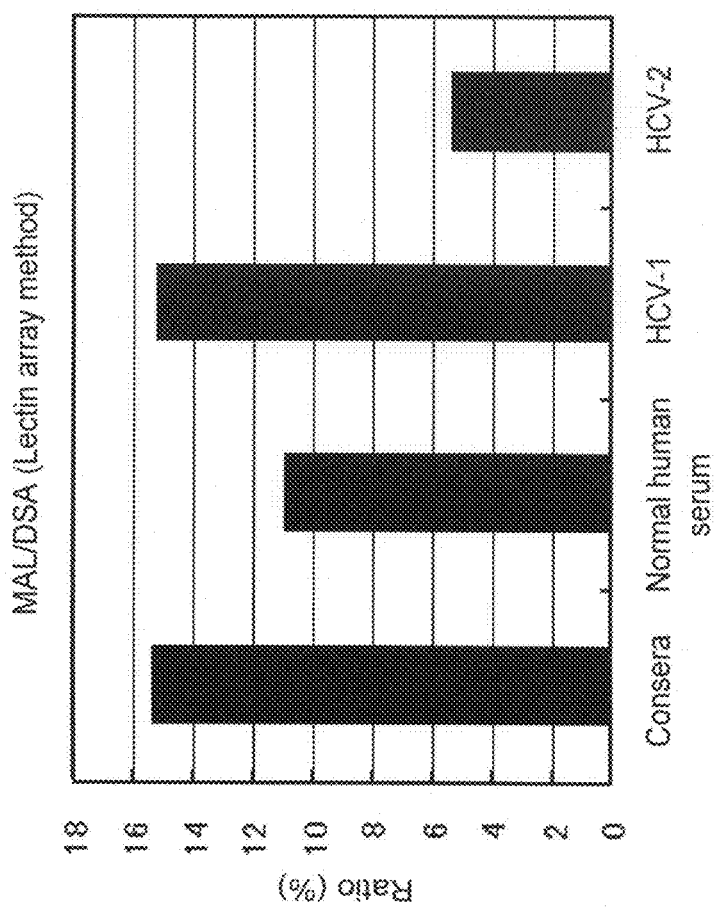
FIG. 18 shows measurement results when MAL was used for commercial specimens in a lectin array method.
Figure 19:
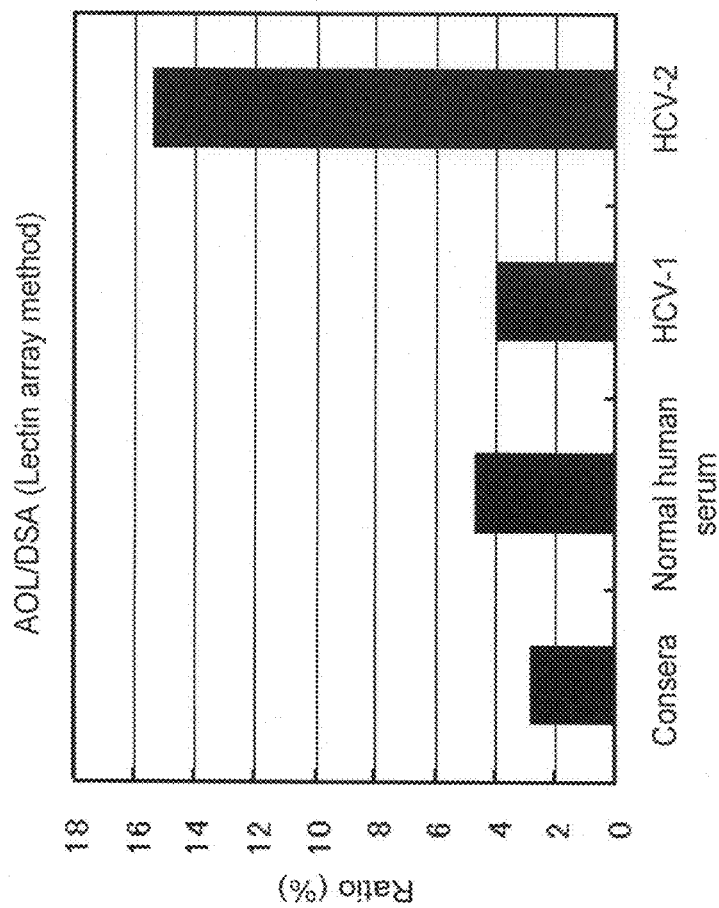
FIG. 19 shows measurement results when AOL was used for commercial specimens in a lectin array method.

Regarding measurement results for MAL subjected to normalization with DSA, it was demonstrated that the measurement results obtained by the $1^{st}$ measurement method shown in the embodiment (shown in FIG. 16) exhibited a good correlation with the measurement results obtained by the lectin array method shown in FIG. 18. Also, regarding the measurement results for AOL subjected to normalization with DSA, the measurement results obtained by the $1^{st}$ rapid measurement method shown in FIG. 17 exhibited a pattern similar to that of and thus a good correlation with the measurement results obtained by the lectin array method shown in FIG. 19.

2. The 2nd Rapid Measurement Method (Automatic Measurement Method)

2-1. Preparation of Reagent

Preparation of R1 reagent: Buffer A (PBS-1% TritonX, pH7.4) was designated as an R1 reagent.

Preparation of R2 reagent: Magnetic particles (number average particle size: 2 µm) to which streptavidin had been immobilized was added to buffer A to 0.5 w/v % and then 2.5 µg/mL biotinylated DSA (J-OIL MILLS, INC.) was added, followed by 30 minutes of stirring at room temperature. After stirring, the magnetic particles were collected and then precipitated, so that solution components were discarded. Buffer A was added to the resultant and then stirred. Magnetic particles were collected and then precipitated, so that solution components were discarded. This procedure was repeated 3 times. Buffer A was added to the resultant so that the concentration of magnetic particles was 0.5 w/v %. The thus obtained solution containing DSA-bearing magnetic particles was designated as R2 reagent 1. R2 reagent 2 containing MAL-bearing magnetic particles was prepared in a manner similar to that for R2 reagent 1 except for the use of 25 µg/mL biotinylated MAL (Vector) instead of 2.5 µg/mL biotinylated DSA (J-OIL MILLS, INC.). R2 reagent 3 containing AOL-bearing magnetic particles was prepared in a manner similar to that for R2 reagent 1 except for the use of 25 µg/mL biotinylated AOL instead of 2.5 µg/mL biotinylated DSA (J-OIL MILLS, INC). In addition, biotinylated AOL used herein was prepared by biotinylation of AOL (Tokyo Kasei Kogyo Co., Ltd.) using a biotin-labeling kit (DOJIDO).

Preparation of R3 reagent: A solution containing 0.1 U/mL ALP (Recombinant AP, EIA Drade, CR 03535452)-labeled mouse anti-AGP monoclonal antibody-Fab', 0.1 M MES (2-(N-Morpholino)ethanesulfonic acid, pH6.5), 0.15 M sodium chloride, 1 mM magnesium chloride, 0.1 mM zinc chloride, 0.1 w/v % $NaN_3$, and 0.25 w/v % casein Na was prepared and designated as R3 reagent 1. R3 reagent 2 was prepared in a manner similar to that for R3 reagent 1 except for the use of 0.1 w/v % BSA instead of 0.25 w/v % casein Na.

In addition, in the above 1st rapid measurement method (manual method), ALP that had not been deglycosylated was used, but in the 2nd rapid measurement method, deglycosylated ALP was used.

Preparation of R4 reagent: A solution containing 0.1 M 2-amino-2-methyl-1-propanol (AMP, pH9.6), 1 mM magnesium chloride, and 0.1 w/v % $NaN_3$ was prepared and designated as an R4 reagent.

Preparation of R5 reagent: CDP-Star with Sapphirine-II (luminescent substrate for ALP, Applied Biosystems) was designated as an R5 reagent.

Preparation of washing reagent: A solution containing 20 mM tris (pH7.4), 0.1 w/v % Tween20, 0.1 w/v % NaN , and 0.8 w/v % sodium chloride was 2-2. Confirmation of Dilution Linearity of a Measurement System Using DSA AGP in Consera (normal human serum, Nissui Pharmaceutical Co., Ltd.) was recovered in buffer B (TBS-0.5% TritonX-0.1% SDS) using an anti-AGP antibody in a manner similar to that for enrichment in Example 1 and then used as a sample. The thus recovered sample was diluted 1-fold, ½-fold, ¼-fold, ⅛-fold, and ¹/₁₆-fold, respectively, with buffer B so that diluted samples were prepared.

Conditions for the operation of a full-automatic immunoassay system HISCL2000i (Sysmex) were changed to the following conditions. Chemiluminescence (photo count value) was measured for each diluted sample using the system.

Figure 20:
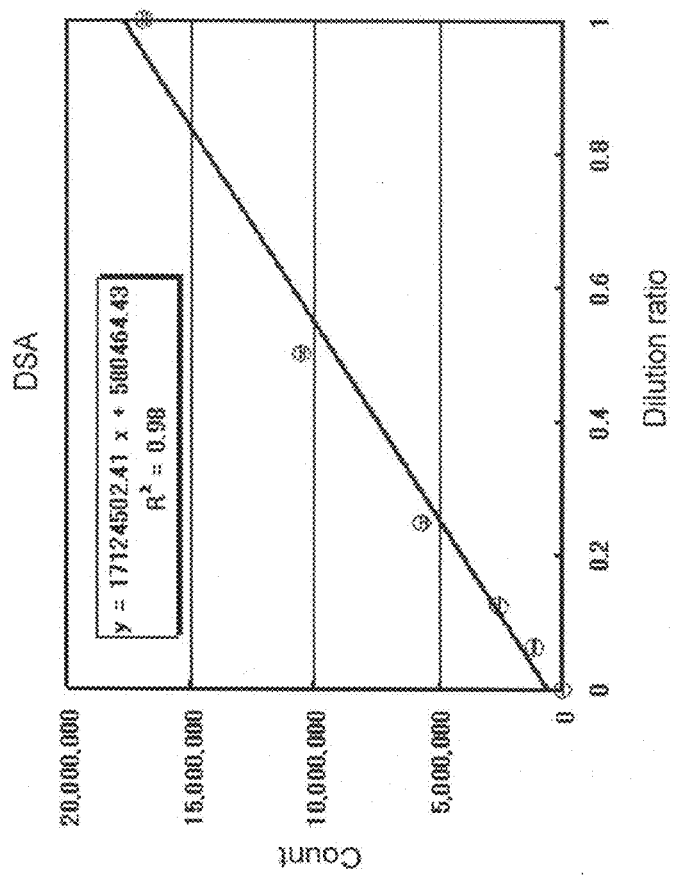
FIG. 20 shows dilution linearity when DSA was used in a $2^{nd}$ rapid measurement method.

Each diluted sample (30 µL) was dispensed into a vessel. After 2.25 minutes of incubation at 42° C., 30 µL of the R2 reagent 1 was dispensed, followed by 2.5 minutes of reaction at 42° C. Furthermore, 100 µL of the R3 reagent 1 was dispensed and then a reaction was performed at 42° C. for 2.75 minutes. Magnetic particles were collected by magnetic separation, so that the solution was vacuumed and discarded. The washing reagent was dispensed, magnetic particles were dispersed in and washed with the washing reagent, magnetic particles were collected by magnetic separation, and thus the solution was vacuumed and discarded. This treatment was repeated 3 times. The R4 reagent (50 µL) was dispensed, 100 µL of the R5 reagent was dispensed, and then chemiluminescence was measured. The above measurement was performed 3 times and then the results are shown in FIG. 20. As shown in FIG. 20, good linearity, $R^2=0.98$, was exhibited in the DSA measurement system.

2-3. Confirmation of Dilution Linearity of a Measurement System Using MAL

Figure 21:
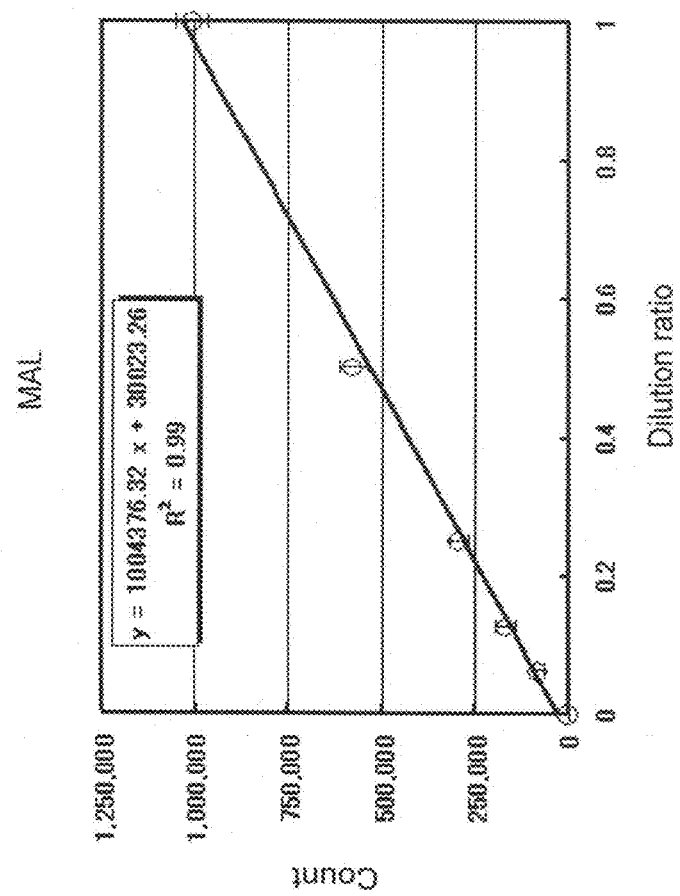
FIG. 21 shows dilution linearity when MAL was used in the $2^{nd}$ rapid measurement method.

An experiment was conducted for confirmation of dilution linearity in the MAL measurement system in a manner similar to that in "Confirmation of dilution linearity of a measurement system using DSA" except for the use of R2 reagent 2 instead of R2 reagent 1 and the use of R3 reagent 2 instead of R3 reagent 1. The results are shown in FIG. 21. As shown in FIG. 21, good linearity, $R^2=0.99$, was exhibited in the MAL measurement system.

2-4. Confirmation of Dilution Linearity of a Measurement System Using AOL

Figure 22:
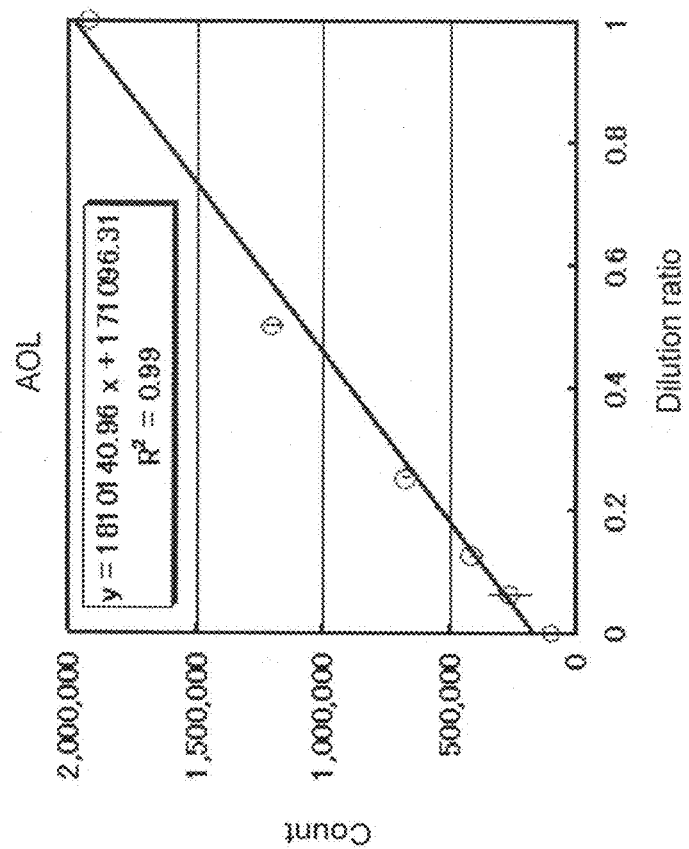
FIG. 22 shows dilution linearity when AOL was used in the $2^{nd}$ rapid measurement method.

An experiment was conducted for confirmation of dilution linearity in the AOL measurement system in a manner similar to that in "Confirmation of dilution linearity of DSA" except for the use of HCV-positive blood plasma 2 (Millenium Biotech) instead of Consera and the use of R2 reagent 3 instead of R2 reagent 1. The results are shown in FIG. 22. As shown in FIG. 22, good linearity, $R^2=0.99$, was exhibited in the AOL measurement system.

2-5. Measurement Using DSA, MAL, and AOL for Various Commercially Available Specimens Consera (normal human serum, Nissui Pharmaceutical Co., Ltd.), normal human serum (TRINA), and HCV-positive blood plasma 1 and 2 (Millenium Biotech) were each subjected to separation of AGP by an immunoprecipitation method using an anti-AGP antibody. Resultants were each recovered in buffer B (TBS-0.5% TritonX-0.1% SDS) and used as samples for measurement. Also, buffer B alone was used as a sample for blank measurement.

Each measurement sample was measured using a full-automatic immunoassay system HISCL2000i under conditions similar to those for "confirmation of dilution linearity of a measurement system using DSA," "confirmation of dilution linearity of a measurement system using MAL," and "confirmation of dilution linearity of a measurement system using AOL." The time required for each measurement was 17 minutes. The results are shown in Table 7, FIG. 23, and FIG. 24.

Table 7

TABLE 7

| | DSA | MAL | AOL | MAL/DSA | AOL/DSA |
|---|---|---|---|---|---|
| Consera | 13757054 | 1377260 | 132648 | 10.0 | 1.0 |
| Normal human serum | 17770250 | 1549266 | 417612.7 | 8.7 | 2.4 |
| HCV-1 | 19885106 | 1877027 | 185538 | 9.4 | 0.9 |
| HCV-2 | 15225585 | 825426.3 | 1776264 | 5.4 | 11.7 |

Figure 23:
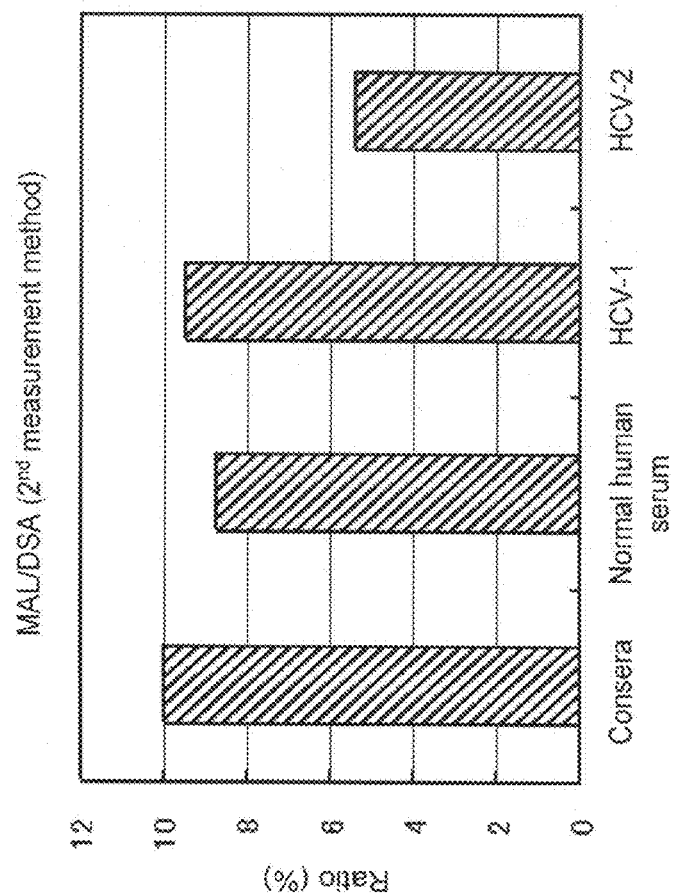
FIG. 23 shows measurement results when MAL was used for commercial specimens in the $2^{nd}$ rapid measurement method.
Figure 24:
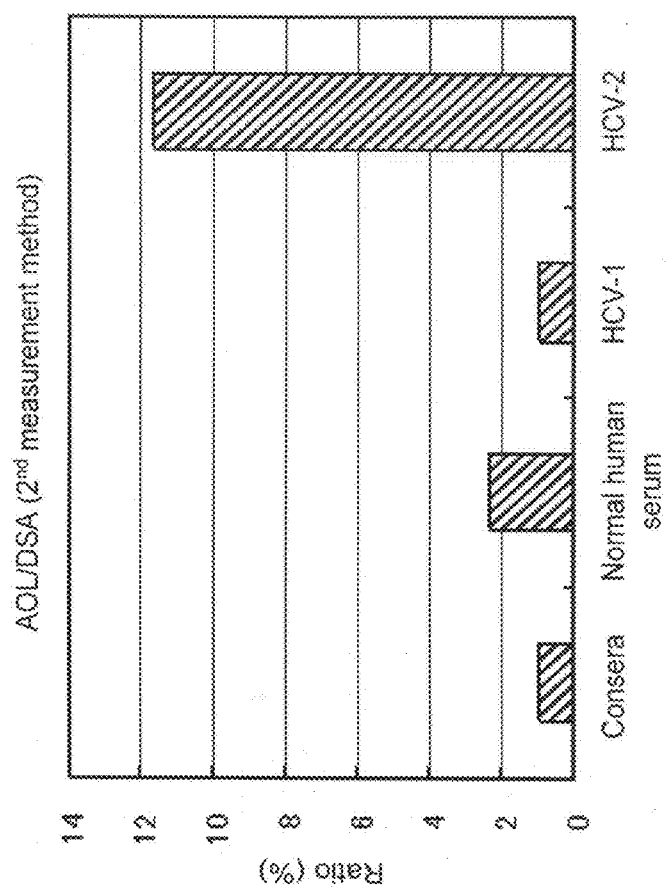
FIG. 24 shows measurement results when AOL was used for commercial specimens in the $2^{nd}$ rapid measurement method.

Regarding the measurement results obtained using MAL subjected to normalization with the measurement result obtained using DSA, it was demonstrated that the measurement results obtained by the $2^{nd}$ rapid measurement method shown in FIG. 23 exhibited a good correlation with the measurement results obtained by the lectin array method shown in FIG. 18. Also, regarding the measurement results obtained using AOL subjected to normalization with measurement results obtained using DSA, the measurement results obtained by the 2nd rapid measurement method shown in FIG. 24 exhibited a pattern similar to that of and thus a good correlation with the measurement results obtained by the lectin array method shown in FIG. 19.

2-6. Measurement of Clinical Specimens Using DSA, MAL, and AOL

Serum 1 and serum 2 from patients at fiber formation stage F1, serum 3 and serum 4 from patients at fiber formation stage F2, serum 5 and serum 6 from patients at fiber formation stage F3, and serum 7 and serum 8 from patients at fiber formation stage F4 were each subjected to separation of AGP using an anti-AGP antibody in a manner similar to that for enrichment in Example 1, and then recovered in buffer B (TBS-0.5% TritonX-0.1% SDS). The resultants were used as samples for measurement. Also, buffer B alone was used as a sample for blank measurement.

Figure 25:
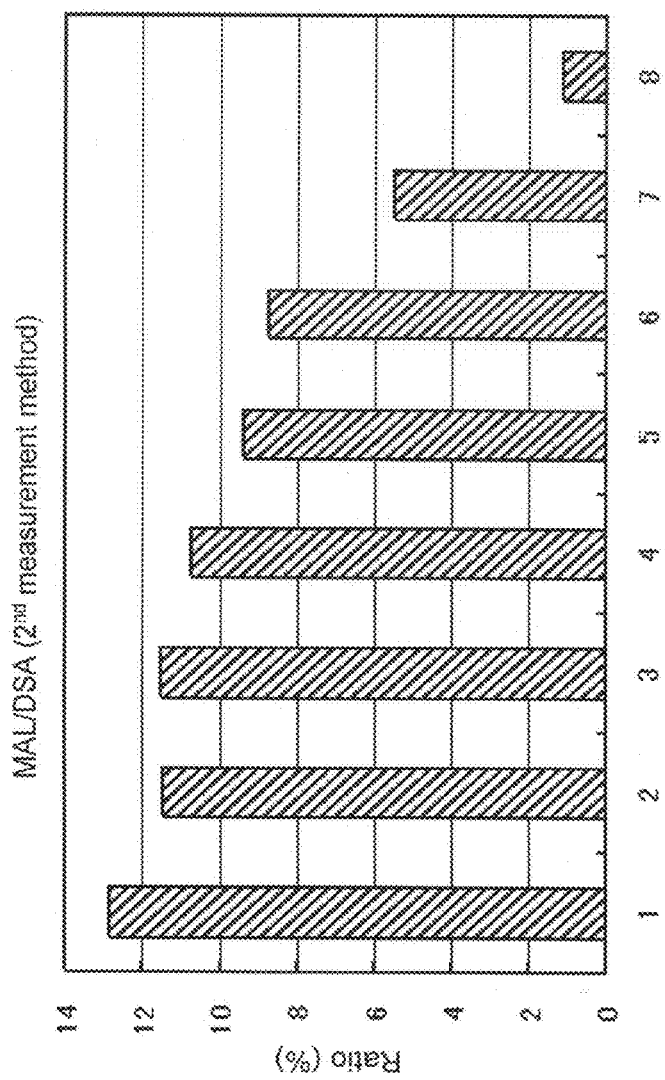
FIG. 25 shows measurement results when MAL was used for clinical specimens in the $2^{nd}$ rapid measurement method.
Figure 26:
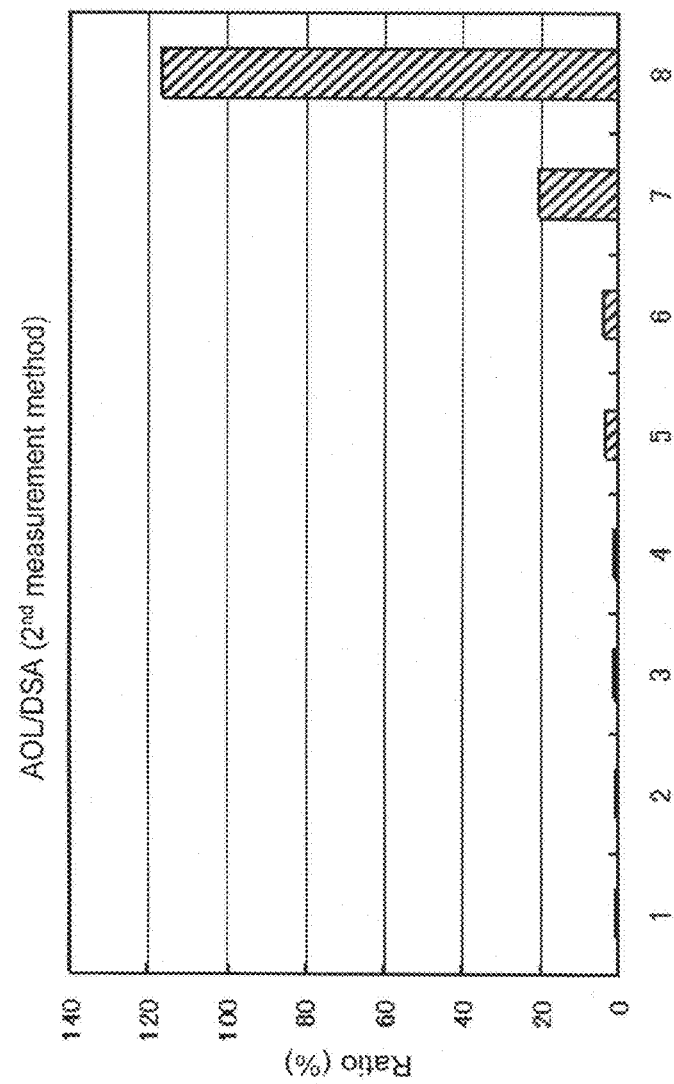
FIG. 26 shows measurement results when AOL was used for clinical specimens in the $2^{nd}$ rapid measurement method.

Each measurement sample was measured using a full-automatic immunoassay system HISCL2000i under conditions similar to those for "confirmation of dilution linearity of a measurement system using DSA," "confirmation of dilution linearity of a measurement system using MAL," and "confirmation of dilution linearity of AOL." The time required for each measurement was 17 minutes. The results are shown in Table 8, FIG. 25, and FIG. 26.

TABLE 8

| Specimen | 1 | 2 | 3 | 4 | 5 | 6 | 7 | 8 |
|---|---|---|---|---|---|---|---|---|
| MAL/DSA | 12.8 | 11.5 | 11.5 | 10.7 | 9.4 | 8.7 | 5.5 | 1.1 |
| AOL/DSA | 0.3 | 0.7 | 0.7 | 1.2 | 3.2 | 3.9 | 20.2 | 117.0 |

2-7. Measurement of Clinical Specimens by a Lectin Array Method

Figure 27:
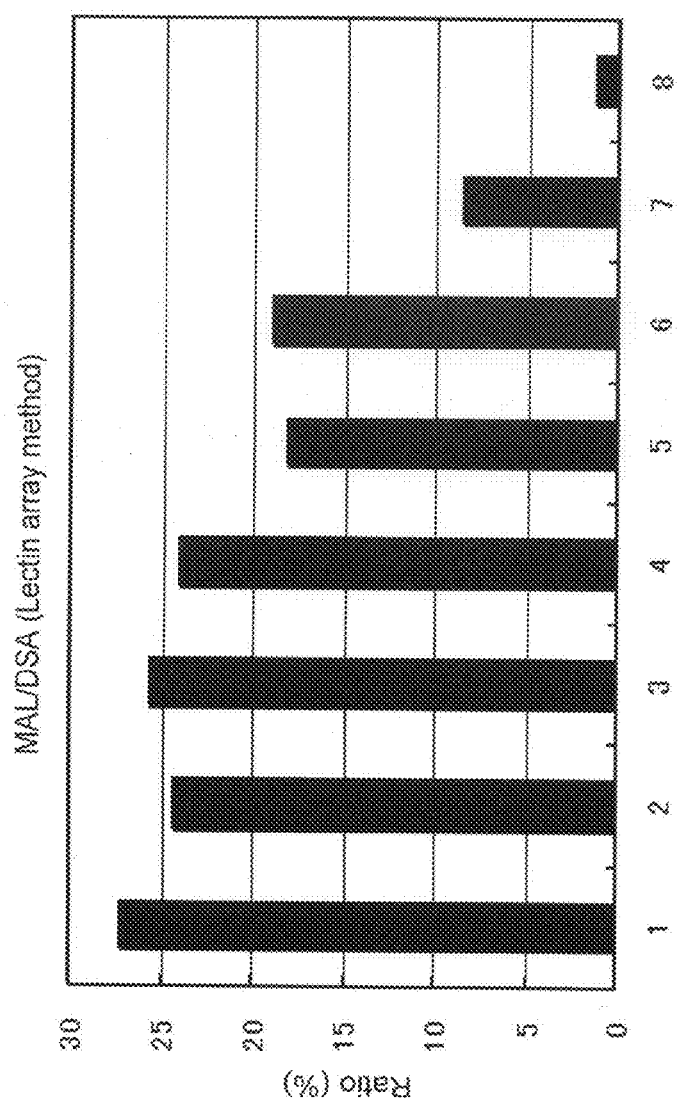
FIG. 27 shows measurement results when MAL was used for clinical specimens in a lectin array method.
Figure 28:
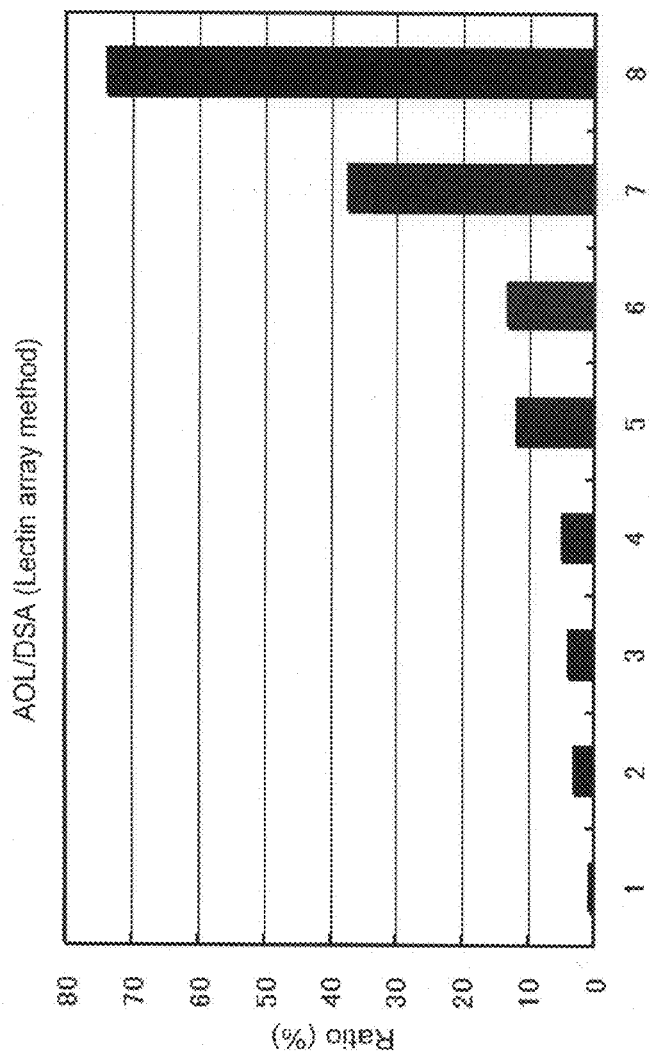
FIG. 28 shows measurement results when AOL was used for clinical specimens in the lectin array method.

Each measurement sample of the above 2-6 was measured by an antibody overlay method using lectin arrays used in Example 1. The time required for measurement by the lectin array method was about 18 hours. The results are shown in Table 9, FIG. 27, and FIG. 28.

TABLE 9

| Specimen | 1 | 2 | 3 | 4 | 5 | 6 | 7 | 8 |
|---|---|---|---|---|---|---|---|---|
| MAL/DSA | 27.3 | 24.3 | 25.6 | 24.0 | 18.1 | 18.9 | 8.5 | 1.3 |
| AOL/DSA | 0.5 | 3.0 | 4.0 | 5.0 | 11.8 | 13.1 | 37.1 | 73.6 |

It was demonstrated based on the results shown in FIG. 25 to FIG. 28 that, also in the case of clinical specimens, the $2^{nd}$ rapid measurement method exhibited a pattern similar to that of and thus a good correlation with the lectin array method.

Example 6

Validation of the $2^{nd}$ Rapid Measurement Method

1. Analysis Using 125 Cases of HCV-Infected Patients

It was revealed by Example 5 that the $2^{nd}$ rapid measurement method exhibited a pattern similar to that of a lectin array. To demonstrate the fact in more cases, the $2^{nd}$ rapid measurement method was performed according to the procedures 2-6 in Example 5 for 125 cases of the patient group (same as that in Example 2) infected with hepatitis virus and pathologically diagnosed by liver biopsy for staging for fiber formation. In addition, the results of staging for fiber formation in the liver performed for 125 cases were: 33 cases at stages F0 and F1, 32 cases at stage F2, and 31 cases at F3, and 29 cases at F4.

Figure 29:
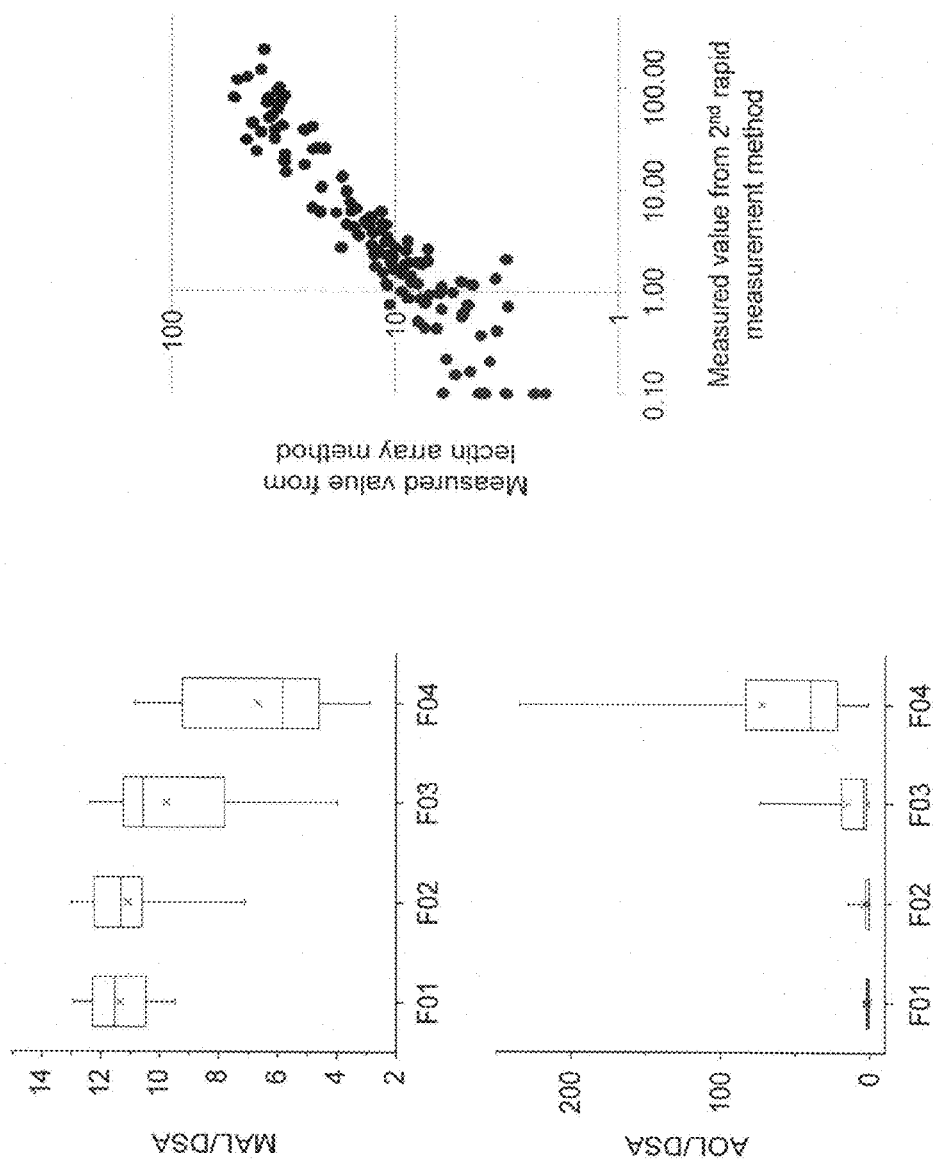
FIG. 29 shows the results of measuring sera of 125 cases of HCV-infected patients by the $2^{nd}$ rapid measurement method.

FIG. 29 shows correlations between the progress of fiber formation in the liver and changes in lectin signal intensity obtained by the 2nd rapid measurement method performed for AGP. Signals on each lectin were normalized with signals on DSA lectin, numerical values were expressed as relative signal intensities when DSA signals (signals on DSA) were designated as 100%. On the left in FIG. 29, the distribution of lectin signals at each stage is shown with box-whisker plots when the $2^{nd}$ rapid measurement method was performed for 125 cases for which staging (F) for fiber formation had been performed by pathologic(al) analysis after liver biopsy. MAL/DSA values were each found from the 3 types of lectin value obtained by the $2^{nd}$ rapid measurement method and then box-whisker plots were created as shown in the upper left portion. AOL/DSA values were also found and then box-whisker plots were created, as shown in the lower left portion. The upper end and the lower end of each box indicate a point of 75% and a point of 25%, respectively. The upper end and the lower end of each whisker indicate a point of 95% and a point of 5%, respectively. A transverse line in each box indicates the median value and "x" indicates the average value. All results strongly resembled to the results of the lectin array. The signal intensity of AOL increased with the progress of fiber formation. It was demonstrated that chronic hepatitis (F0-3) and cirrhosis (F4) can be sufficiently distinguished from each other based on a difference in intensity. On the other hand, the signal intensity of MAL was found to decrease with the progress of fiber formation. To support the fact that a correlation was present between the results of the lectin array and the results of the $2^{nd}$ rapid measurement method, numerical values obtained from the two were plotted two-dimensionally. The graph is shown on the right in FIG. 29. It was revealed from the graph that there is a strong correlation between the results of the lectin array and the results of the $2^{nd}$ rapid measurement method.

2. Detection of Cirrhosis

Detection of cirrhosis by the $2^{nd}$ rapid measurement method was attempted by procedures similar to those for detection of cirrhosis using lectin arrays described in Example 3. An ROC curve for distinguishing F4 (cirrhosis) from the other (F1-F3) was created for 125 cases of the above pathologically diagnosed patients using data obtained by normalization of signals on 2 types of lectin with the signals on DSA lectin. Also, a point on a curve, which is located closest to the point of 100% sensitivity and the point of 100% specificity, in other words, a contact point between a line parallel to the line of Y=X and the ROC curve, was designated as "optimum specificity and sensitivity" and in the periphery cut-off values were determined. A combination equation (AOL/DSA×1.8−MAL/DSA) optimum for detection of cirrhosis was found based on the thus obtained cut-off value for each lectin. Accordingly, a blind test was performed for 45 cases and 43 cases of patients definitively diagnosed as having hepatitis and cirrhosis by pathological diagnosis or diagnostic imaging clinical diagnosis.

As a result, the detection ability examined using the combination equation (AOL/DSA×1.8−MAL/DSA) was represented by the sensitivity of 88.3%, the specificity of 91.1%, and the accuracy of 89.8%.

Figure 30:
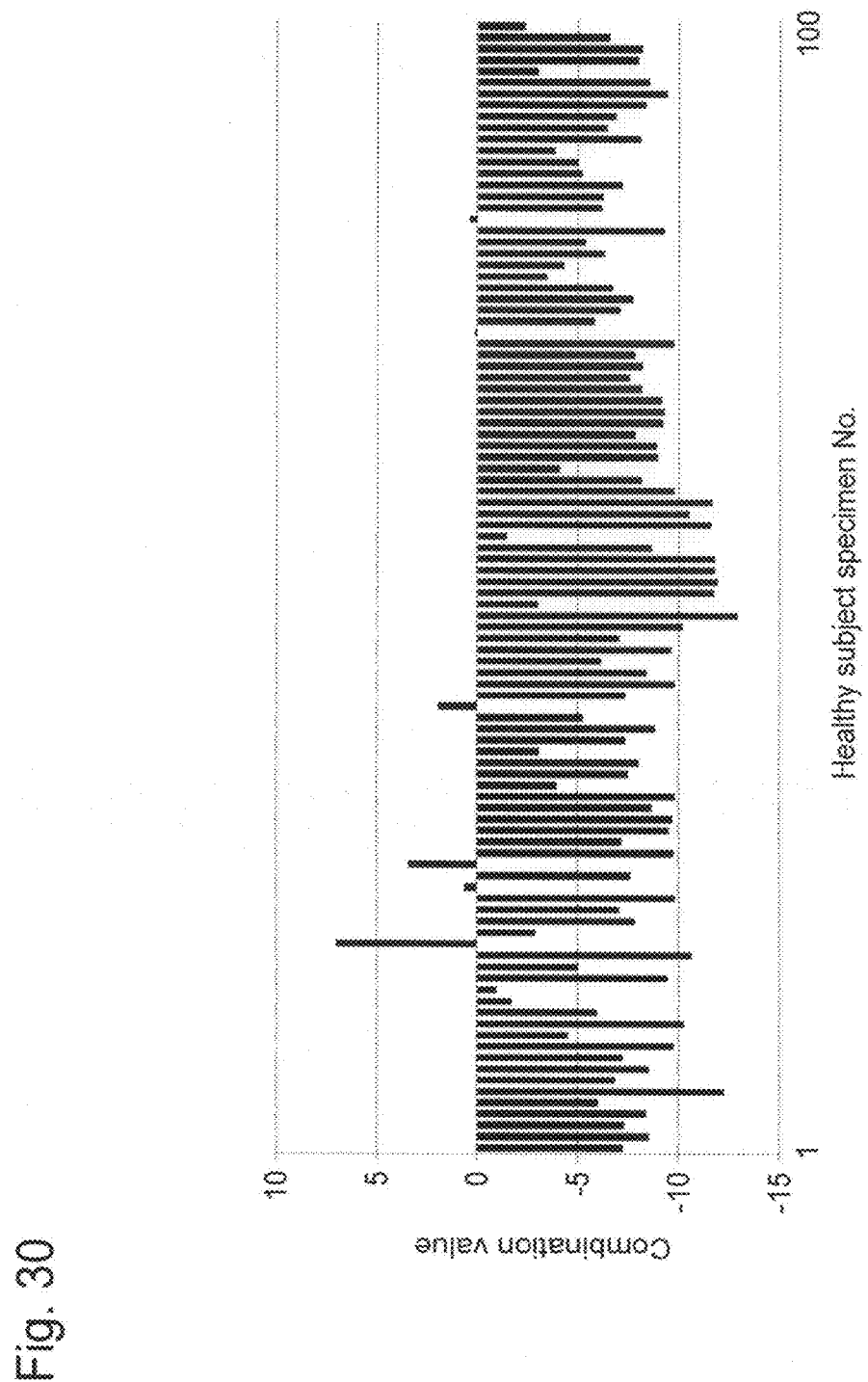
FIG. 30 shows comparison of the results obtained from 100 specimens of healthy subjects by a lectin array method with the results obtained from the same by the $2^{nd}$ rapid measurement method.

Next, to examine the frequency of false-positive results from the equation, sera from 100 healthy subjects were also analyzed by the $2^{nd}$ rapid measurement method. Determination of cirrhosis was performed using the equation. As shown in FIG. 30, false-positive rate was found to be 5%, such that the results of lectin arrays were consistent with those of the false-positive specimens.

Example 7

Figure 31:
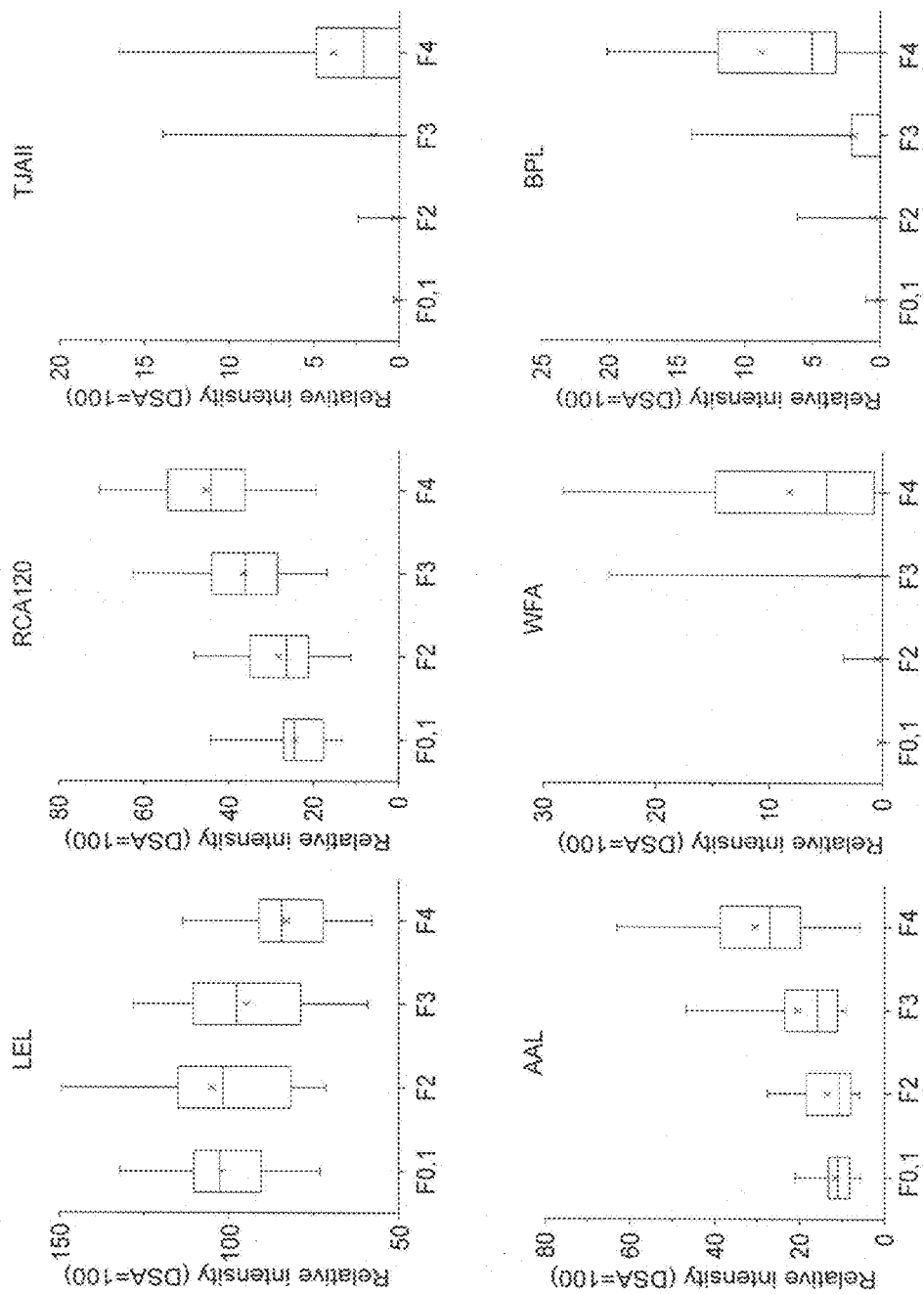
FIG. 31 shows correlation between the progress of fiber formation in the liver and changes in lectin signal intensity obtained by antibody-overlay-lectin array analysis of M2BP.

Identification of the Progress of Fiber Formation in the Liver by Antibody-overlay Lectin Array Analysis of a Candidate Glycan-marker Glycoprotein M2BP as an Index for Clinical Conditions of Liver Disease As described in Example 2, a possibility was found also for M2BP, such that each type of clinical condition of liver disease can be detected based on the lectin signal information obtained by antibody-overlay lectin array analysis. Hence, an experiment for examination of a correlation with fiber formation in the liver was conducted. Antibody-overlay lectin microarray was performed according to the procedures in Example 2 for 125 cases of a group of patients (same as those in the experiment for AGP) infected with hepatitis virus and pathologically diagnosed by liver biopsy for staging for fiber formation. Graphs showing correlations between 6 lectins (out of 17 types of lectin for which binding signals had been generated), for which signal changes had been confirmed by a significance difference test with the progress of fiber formation, and the progress of fiber formation were created, as shown in FIG. 31. The distribution of the lectin signals at each stage is shown with a box-whisker plot. The upper end and the lower end of each box indicate a point of 75% and a point of 25%, respectively. The upper end and the lower end of each whisker indicate a point of 95% and a point of 5%, respectively. A transverse line in each box indicates the median value and "x" indicates the average value. In addition, the vertical axis of each graph represents relative values when DSA signals were designated as 100%. It was revealed that signal intensities of RCA120, AAL, TJAII, WFA, and BPL increased with the progress of fiber formation, while the signal intensity of LEL decreased with the progress of fiber formation. Of these lectins, RCA120 and AAL are thought to be suitable in view of monitoring the progress of fiber formation. Also, signals were generated on TJAII, WFA, and BPL when the cirrhosis stage reached F4. Moreover, TJAII, WFA, and BPL signals were varied significantly in the case of F4, suggesting a possible use of TJAII, WFA, and BPL as effective markers for discriminating a high risk group for cancer.

Example 8

Figure 32:
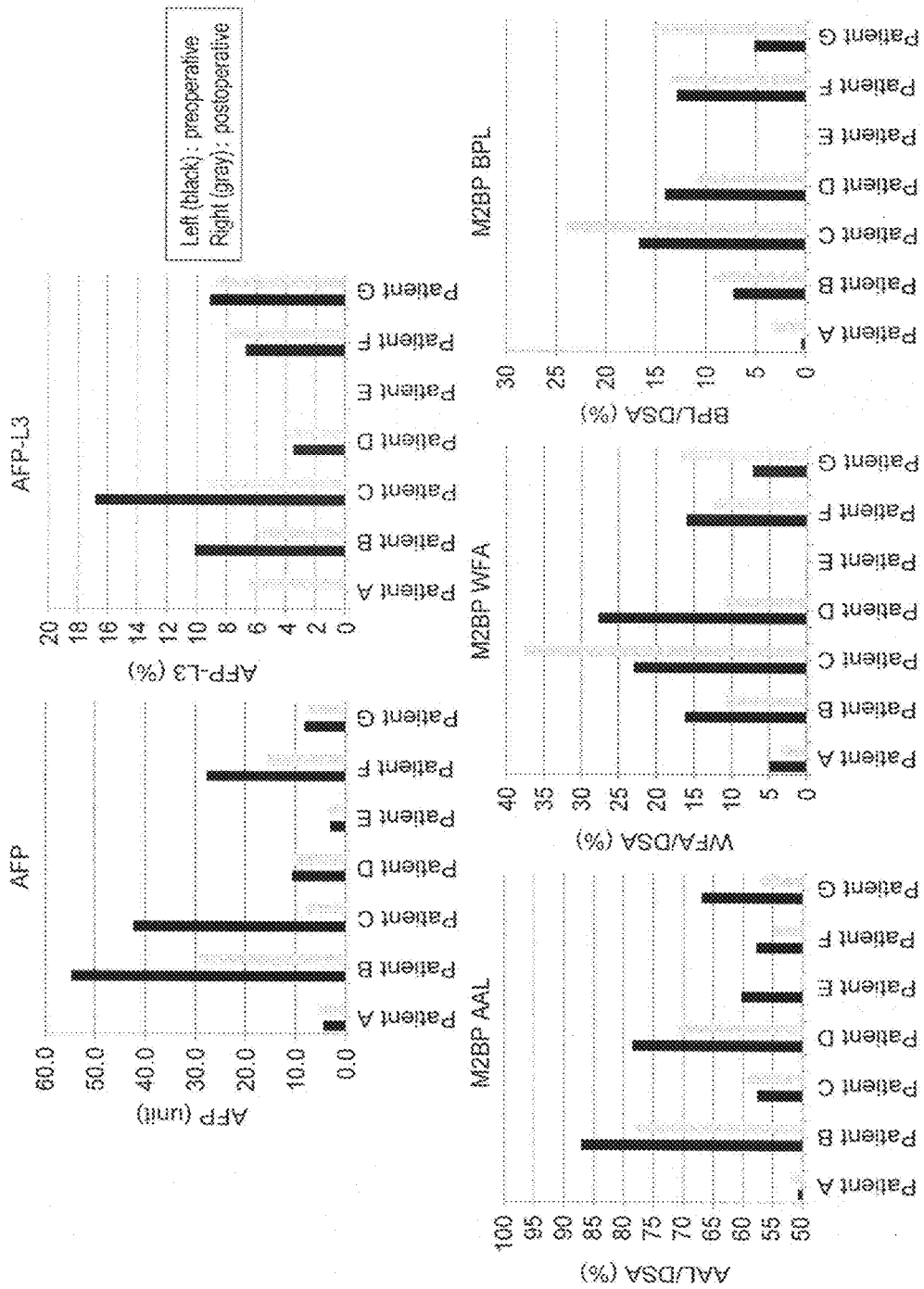
FIG. 32 shows preoperative and postoperative glyco-alterations in M2BP in sera from hepatic cell carcinoma patients.

Discrimination of a High Risk Group for Liver Cancer by Detection of Glyco-alterations in M2BP 1. Selection of Lectins Suitable for Discriminating a High Risk Group for Liver Cancer A group of lectins with signal intensities that increased with the progress of fiber formation in the liver was found in Example 7. To discriminate lectins capable of discriminating a high risk group for cancer from the group of lectins, antibody-overlay lectin microarray analysis of M2BP was conducted for sera from 7 cases of preoperative and postoperative patients with hepatic cell carcinoma. The experimental procedures were employed according to Example 1. Also, with the use of a full-automatic fluorescence immunoassay apparatus (μTAS Wako i30; Wako Pure Chemical Industries, Ltd.) and a special-purpose reagent, an amount of known hepatic cell carcinoma marker AFP in the blood and benign disorder•hepatic cell carcinoma distinguishing marker AFP-L 3% were also measured. The resulting lectin signal patterns are partially shown in FIG. 32. All parameters including AFP-L 3% did not always exhibit post-operative signal decreases in all the 7 cases. This means that all of these markers are not cancer detection markers. An object of the experiment is to select candidate markers for discriminating a high risk group for hepatic cell carcinoma. With regard to this point, a desired candidate marker exhibits a pattern analogous to that exhibited by AFP-L 3%. As predicted in Example 7, WFA and BPL lectins exhibited patterns analogous to that of AFP-L 3%. Moreover, the signal intensity of WFA was stronger and more stable than that of BPL, so that WFA was selected as a powerful candidate lectin.

2. Detection of WFA-binding M2BP by a Lectin-antibody Sandwich ELISA Method

Figure 33:
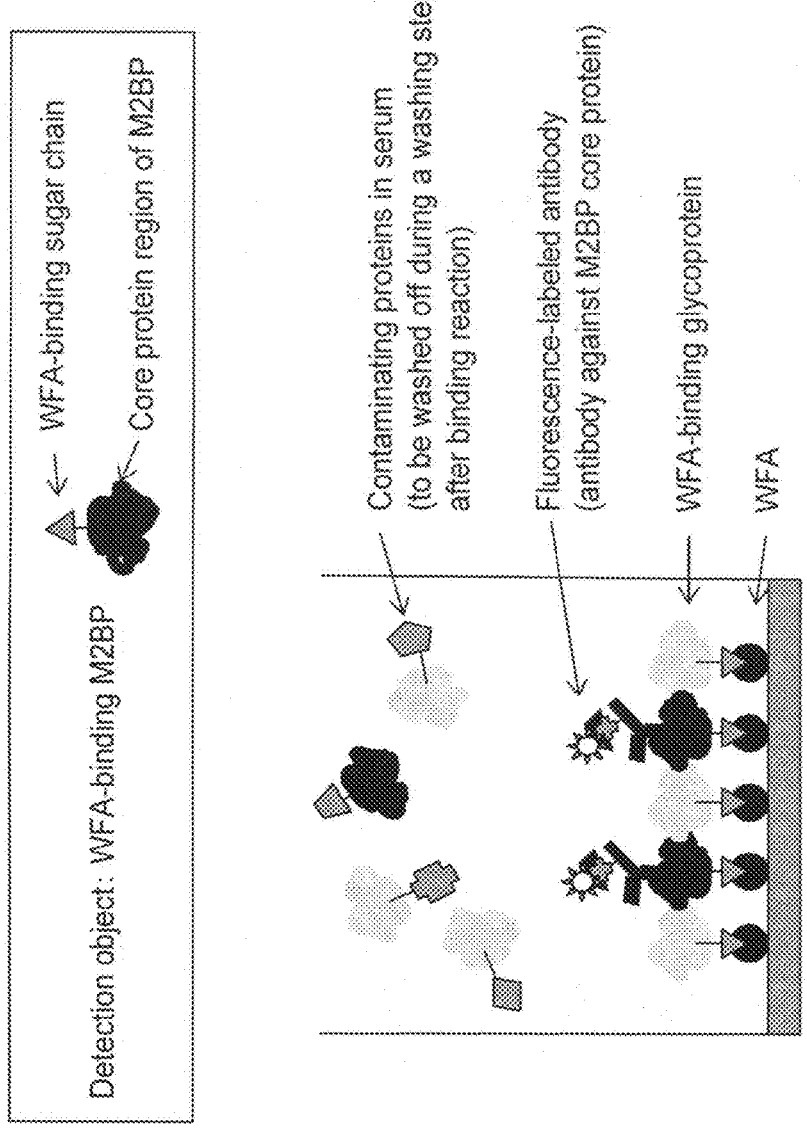
FIG. 33 shows a lectin-antibody sandwich ELISA model that is the best mode for detection of WFA-binding M2BP.

The best mode for detection of WFA-binding M2BP as a biomarker for discriminating a high risk group for liver cancer can be a method for detecting and identifying biomarkers contained in serum by a clinically applicable convenient means with clinically acceptable performance. The results of sandwich detection analysis using an anti-M2BP antibody overlay-WFA well plate (see FIG. 33) are as shown below. In addition, serum can be directly added to a WFA well plate in this technique. The reason of this is that very few glycoprotein molecules contained in serum can bind to WFA and in patients of a high risk group for cancer, M2BP is one of molecules with the highest concentration in the blood.

(Experimental Methods)

Fifty (50) μL each of biotinylated WFA (Vector, 5 μg/mL) dissolved in a PBS buffer was added to each well of a microtiter plate (Greiner Bio-One, 96-well flat-bottomed streptavidin-coated plate) and then maintained at room temperature for 2 hours, so that WFA was immobilized to a support. The plate was washed twice with a wash (0.1% Tween 20-containing PBS (300 μL)) to remove unbound WFA so that the preparation of a WFA-immobilized well plate was completed.

Each sample (1 μL) was diluted with 50 μL of the above wash and then the diluted sample was added to the WFA-immobilized well plate prepared in 1, followed by 2 hours of binding reaction at room temperature. After reaction, each well was washed 5 times with 300 μL of the above wash, so that unbound proteins were removed. A detection agent (goat anti-M2BP polyclonal antibody solution; R&D Systems) adjusted in advance with a wash to 1.0 μg/mL was added with 50 μL per well, followed by 2 hours of antigen-antibody reaction at room temperature.

After washing with 300 μL of a wash to remove unbound antibodies, an anti-goat IgG antibody-HRP solution (Jackson immuno Research) diluted 10,000-fold in advance with a wash was added with 50 μL it per well and then the resultants were maintained at room temperature for 1 hour. Each well was washed 5 times with 300 μL of a wash, and then an ULTRA-TMB solution (Thermo) as a coloring reagent was added with 100 μL per well, followed by 10 minutes of coloring reaction. A 1 M $H_2SO_4$ solution was added with 100 μL per well to stop the reaction, and then absorbance was measured at 450 nm using a plate reader. The serum of a healthy subject was designated as a negative control (N), numerical conversion of the thus obtained signals was performed to find S/N ratios, and then the resulting data were used for the following analysis.

Results

Figure 34:
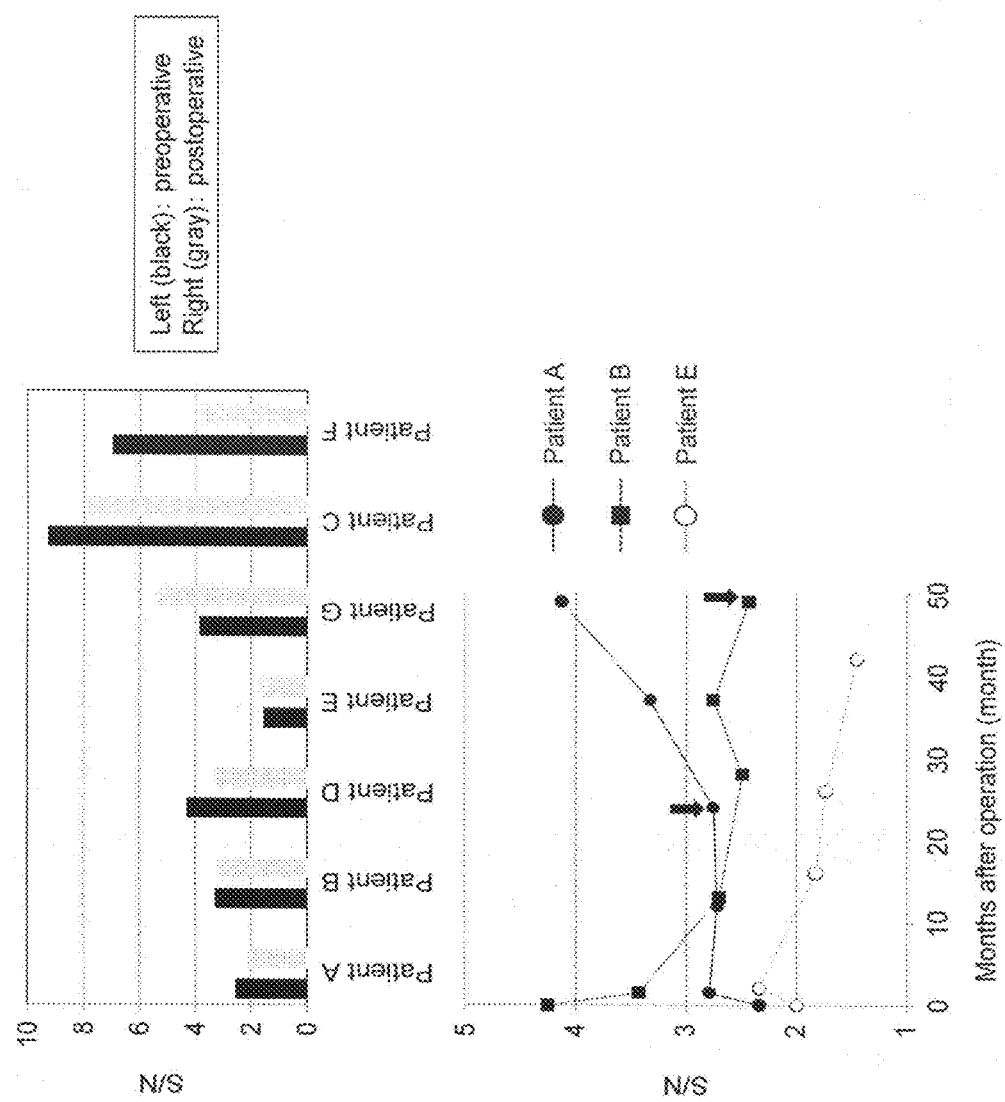
FIG. 34 shows the postoperative time course changes in the amounts of WFA-binding M2BP in sera from liver cancer patients.

First, assay was performed for sera from 7 cases of the above preoperative and postoperative hepatic cell carcinoma patients. As a result, signal patterns that strongly resembled to the results in FIG. 32 were obtained (upper portion of FIG. 34). Of these cases, 3 cases for which postoperative blood collection had been sequentially performed were subjected to measurement of the amount of WFA-binding M2BP. In addition, patients A and B were postoperative recurrence cases, and patient E was a no-recurrence case. A point at which recurrence occurred is indicated with an arrow. The results are shown in the lower portion of FIG. 34. The horizontal axis represents elapsed months with the date of operation designated as "0." Also, the vertical axis represents S/N ratios with the serum from a healthy subject designated as a negative control (N). In the case of patient A, the measured value fluctuated near S/N=2.5 even after operation and increased on and after the recurrence point. In the case of patient B, the preoperative measured value was very high, but the value decreased after operation and remained unchanged near S/N=2.5. On the other hand, in the case of patient E, the lowest measured value, S/N=2.0, was confirmed before and after operation, and the numerical value gradually decreased. It was found based on the above results that while patients with measured values that had remained unchanged near S/N>2.5 after operation have a high recurrence risk, and patients with measured values that had increased after recurrence, but rapidly decreased after operation to levels significantly lower than S/N=2.0 may likely have no recurrence. As described above, WFA-binding M2BP is useful as a marker for discriminating a high risk group for liver cancer and the anti-M2BP antibody overlay-WFA well plate could be developed as a convenient measurement system for detection of the same.

Example 9

Verification of the Effects of Heat Treatment for Specimens Upon Detection of WFA-binding M2BP by an ELISA Method The effects of the presence or the absence of heat treatment for specimens on the sensitivity of detection of WFA-binding M2BP by an ELISA method were confirmed.

A human liver cancer-derived cell line (HepG2 culture supernatant) was diluted 10-fold with a 0.2% SDS-containing PBS buffer, followed by 10 minutes of heat treatment at 95° C.

M2BP binding to WFA was measured by a method similar to that in 2 of Example 8 except that an HepG2 culture supernatant (untreated) and an HepG2 culture supernatant (heat-treated) were used as samples so that the amount of protein per well was as listed in Table 10. Absorbance measured using a plate reader is shown in Table 10 and FIG. 35.

TABLE 10

| ng total protein/well | Untreated | Heat-treated |
|---|---|---|
| 5000 | 2.073 | 0.365 |
| 3000 | 1.861 | 0.275 |
| 1000 | 1.372 | 0.143 |
| 500 | 1.102 | 0.097 |
| 100 | 0.398 | 0.032 |

TABLE 10-continued

| ng total protein/well | Untreated | Heat-treated |
|---|---|---|
| 50 | 0.181 | 0.03 |
| 10 | 0.047 | 0.05 |

Figure 35:
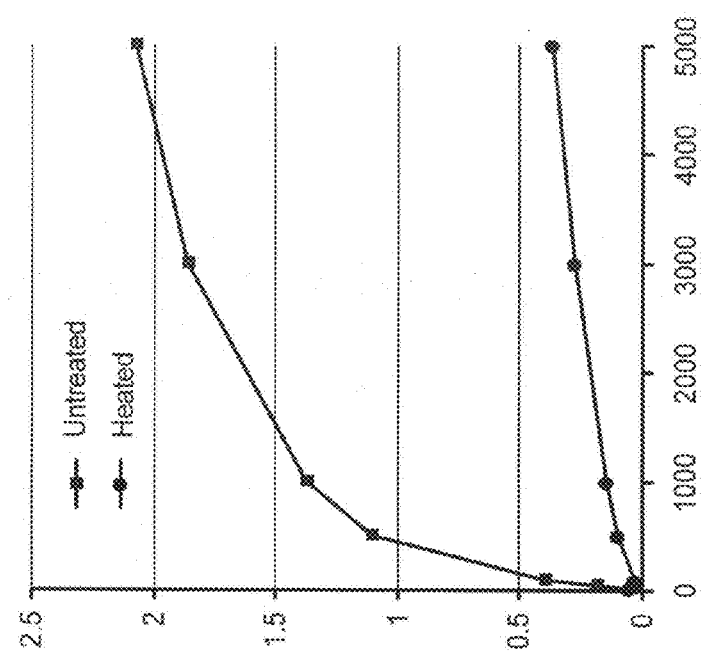
FIG. 35 shows the effects of the presence or the absence of heat treatment for specimens on detection sensitivity during detection of WFA-binding M2BP by ELISA.

It was revealed based on the results in Table 10 and FIG. 35 that the use of serum that had not been heat-treated as a measurement sample in measurement of WFA-binding M2BP by the ELISA method improved measurement sensitivity.

Example 10

Measurement of M2BP by the $2^{nd}$ Rapid Measurement Method

1. Preparation of Reagents

Preparation of R1 reagent: A solution (buffer C) containing 10 mM HEPES (pH 7.5), 150 mM NaCl, 0.01 mM $MnCl_2$, 0.1 mM $CaCl_2$, and 0.08 w/v % $NaN_3$ was prepared and then designated as an R1 reagent.

Preparation of R2 reagent: Magnetic particles (number average particle size: 2 μm) (hereinafter, referred to as streptavidin-sensitized magnetic particles) to which commercially available streptavidin had been immobilized were added to buffer C to a concentration of 0.5 w/v %, and then a biotinylated lectin solution (WFA) was added to the solution. The mixed solution was stirred at room temperature for 30 minutes. After stirring, magnetic particles were collected with magnet for precipitation, and then solution components were discarded. After washing 3 times with buffer C, buffer D (the solution containing 10 mM HEPES (pH7.5), 150 mM NaCl, 0.01 mM $MnCl_2$, 0.1 mM $CaCl_2$, 0.1% WN BSA, and 0.08 w/v % $NaN_3$) was added so that the concentration of magnetic particles was 0.5 w/v %.

Preparation of R3 reagent: A solution containing a 0.1 U/mL recombinant ALP-labeled mouse anti-M2BP monoclonal antibody, 0.1 M MES (2-(N-Morpholino)ethanesulfonic acid, pH6.5), 0.15M NaCl, 1 mM $MgCl_2$, 0.1 mM $ZnCl_2$, and 0.1w/v % $NaN_3$ was prepared and then designated as an R3 reagent.

As an R4 reagent, an R5 reagent, and a washing reagent, the R4 reagent, the R5 reagent, and the washing reagent used in the 2nd rapid measurement method in Example 5 were used.

2. Confirmation of Dilution Linearity of a Measurement System Using WFA

A human liver cancer-derived cell line culture supernatant (HepG2 culture supernatant) (100 μg/ml) was diluted 10-fold, 100-fold, 1000-fold, and 10000-fold with a buffer (PBS), so that diluted samples were prepared. Also, 5 μg/ml recombinant human galectin-3BP/MAC-2BP (R&D SYSTEMS) was diluted 2-fold, 4-fold, 8-fold, 16-fold, 32-fold, and 64-fold with a buffer (PBS), so that diluted samples were prepared.

Conditions for the operation of a full-automatic immunoassay system HISCL2000i (Sysmex) were changed to the following conditions. Chemiluminescence intensity (photo count value) was measured for each diluted sample.

Figure 36:
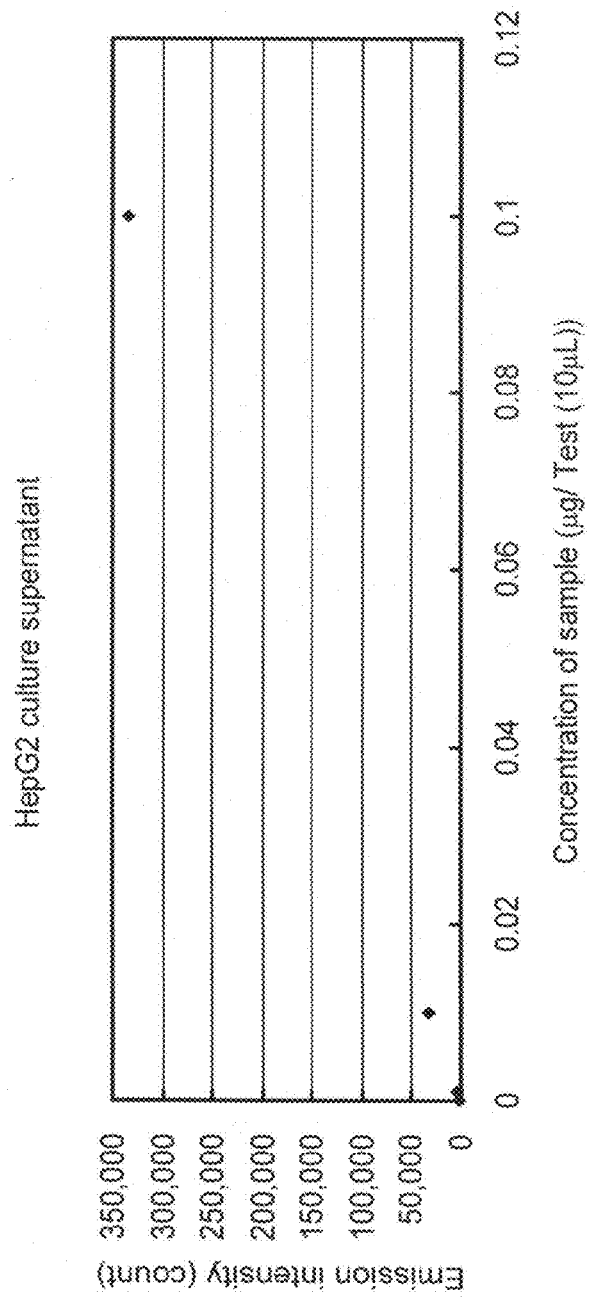
FIG. 36 shows the dilution linearity of a measurement system using WFA when the supernatants of cultured HepG2 cells were used as samples in measurement of M2BP by the $2^{nd}$ rapid measurement method.
Figure 37:
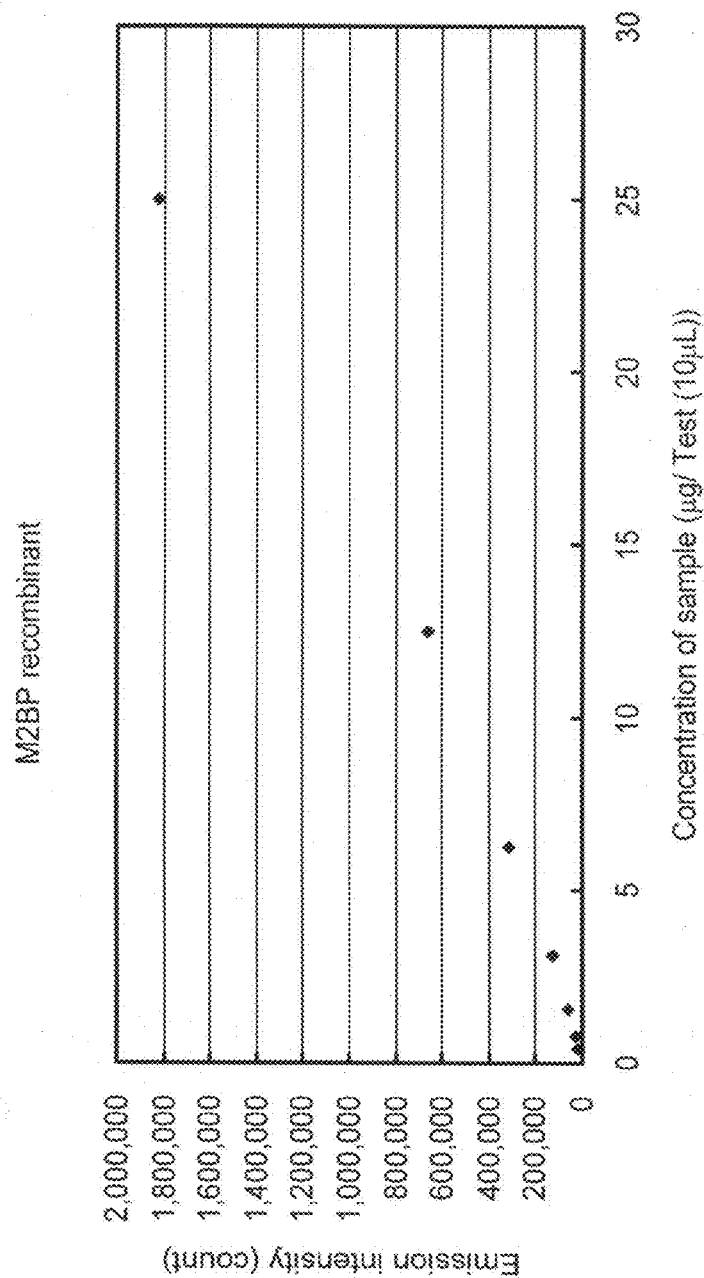
FIG. 37 shows the dilution linearity of a measurement system using WFA when recombinant human galectin-3BP/MAC-2BP was used as a sample in measurement of M2BP by the $2^{nd}$ rapid measurement method.

The R1 reagent (30 μL) and 10 μL of each diluted sample were dispensed to a vessel. After 2.25 minutes of incubation at 42° C., 30 μL of the R2 reagent was dispensed, followed by 1.5 minutes of reaction at 42° C. Magnetic particles were collected by magnetic separation, so that the solution was vacuumed and discarded. The washing reagent was dispensed, magnetic particles were dispersed in and washed with the washing reagent and then collected by magnetic separation, so that the solution was vacuumed and discarded. This treatment was repeated 3 times. The R3 reagent (100 μL) was dispensed, followed by 2.75 minutes of reaction at 42° C. Magnetic particles were collected by magnetic separation and thus the solution was vacuumed and discarded. The washing reagent was dispensed, magnetic particles were dispersed in and washed with the washing reagent and then collected by magnetic separation, and thus the solution was vacuumed and discarded. This treatment was repeated 3 times. The R4 reagent (50 μL) was dispensed, 100 μL of the R5 reagent was dispensed, and then the chemiluminescence intensity was measured. Measurement results for the supernatant of cultured HepG2 cells are shown in Table 11 and FIG. 36 and the measurement results of recombinant human galectin-3BP/MAC-2BP are shown in Table 12 and FIG. 37. As shown in these measurement results, WFA measurement system exhibited good dilution linearity.

TABLE 11

| μg/test (10 μL) | Luminescence intensity (count) | S/N (with respect to diluent) |
|---|---|---|
| Diluent (PBS) | 2,987 | 1.00 |
| 0.0001 | 3,043 | 1.02 |
| 0.001 | 4,850 | 1.62 |
| 0.01 | 31,671 | 10.60 |
| 0.1 | 332,706 | 111.38 |

TABLE 12

| μg/test (10 μL) | Luminescence intensity (count) | S/N (with respect to diluent) |
|---|---|---|
| Diluent (PBS) | 2,987 | 1.00 |
| 0.3906 | 14,456 | 4.84 |
| 0.7813 | 26,640 | 8.92 |
| 1.5625 | 55,721 | 18.65 |
| 3.125 | 123,939 | 41.49 |
| 6.25 | 313,747 | 105.04 |
| 12.5 | 663,628 | 222.17 |
| 25 | 1,822,168 | 610.03 |

3. Measurement for Clinical Specimens

Sera from a healthy subject, an HBV-positive hepatic cell carcinoma patient, and an HCV-positive hepatic cell carcinoma patient were measured using a full-automatic immunoassay system HISCL2000i under conditions similar to those in "2. Confirmation of dilution linearity of a measurement system using WFA." The time required for measurement of each specimen was 17 minutes. The results are shown in Table 13.

TABLE 13

| | Luminescence intensity (count) | S/N (with respect to serum from healthy subject) |
|---|---|---|
| Serum from healthy subject | 654,663 | 1 |
| Serum from HBV-positive liver cancer patient | 11,317,040 | 17.3 |
| Serum from HCV-positive liver cancer patient | 17,124,911 | 26.2 |

It could be confirmed based on the results in Table 13 that M2BP binding to WFA can be rapidly and precisely measured by the $2^{nd}$ rapid measurement method.

The present invention can be used for producing apparatuses, instruments, or kits for determining liver disease or clinical conditions of liver disease, distinguishing among clinical conditions of liver disease, or detecting cirrhosis, for example.

What is claimed is:

1. A method for examining liver disease exhibiting fiber formation, comprising:
   (a) contacting a blood sample collected from a subject with *Wisteria floribunda* lectin (WFA);
   (b) assaying glycosylated Mac-2-binding protein (M2BP) bound to the WFA, and
   (c) determining a stage of fiber formation in the liver based on the assayed value of the glycosylated M2BP.

2. A method for examining liver disease exhibiting fiber formation according to claim 1, further comprising contacting the blood sample with a lectin for normalization of which reactivity is not substantially altered regardless of glycan structural changes in M2BP, measuring M2BP bound to the lectin for normalization and normalizing the assayed value of M2BP bound to the WFA using the measured value of M2BP bound to the lectin for normalization.

3. A method for examining liver disease exhibiting fiber formation according to claim 2, wherein the lectin for normalization is *Datura stramonium* lectin (DSA).

4. A method for examining liver disease exhibiting fiber formation according to claim 1, wherein the contacting is performed by contacting the sample, the WFA and a labeled anti-M2BP antibody, and forming a complex of the WFA, the M2BP, and the labeled anti-M2BP antibody, wherein the assaying is performed by measuring the amount of the label of the complex, and quantitatively determining the M2BP bound to the WFA.

5. A method for examining liver disease exhibiting fiber formation according to claim 4, wherein the complex is formed using magnetic particles to which the WFA is immobilized.

6. A method for examining liver disease exhibiting fiber formation according to claim 4, wherein the complex is formed using the biotinylated WFA and magnetic particles to which streptavidin or avidin are immobilized.

7. A method for examining liver disease exhibiting fiber formation according to claim 4, wherein the label of the labeled anti-M2BP antibody is deglycosylated alkaline phosphatase.

8. A method for examining liver disease exhibiting fiber formation according to claim 4, wherein the anti-M2BP antibody is a deglycosylated anti-M2BP antibody.

9. A method for examining liver disease exhibiting fiber formation according to claim 1, wherein the assaying is performed by measuring M2BP bound to the WFA with the use of a lectin array to which at least the WFA is immobilized and an anti-M2BP antibody.

10. A method for examining liver disease exhibiting fiber formation according to claim 9, wherein: DSA is further immobilized to the lectin array; M2BP bound to DSA is measured and then the measured value of M2BP bound to the WFA is normalized using the assayed value of M2BP bound to DSA.

11. A method for examining liver disease, comprising
   a) contacting a blood sample collected from a subject suffering from liver disease exhibiting fiber formation with *Wisteria floribunda* lectin (WFA);
   b) assaying glycosylated Mac-2-binding protein (M2BP) bound to the WFA; and
   c) determining whether or not the disease is cirrhosis based on the assayed value of the glycosylated M2BP.

12. A method for examining liver disease, comprising:
a) contacting a blood sample collected from a subject suffering from liver disease exhibiting fiber formation with *Wisteria floribunda* lectin (WFA);
b) assaying glycosylated Mac-2-binding protein (M2BP) bound to the WFA; and
c) determining whether or not the disease is hepatic cell carcinoma based on the assayed value of the glycosylated M2BP.

13. A method for determining the therapeutic effect of an anti-viral agent in treatment for liver disease exhibiting fiber formation, comprising:
a) contacting a blood sample collected from a subject suffering from liver disease with *Wisteria floribunda* lectin (WFA);
b) assaying glycosylated Mac-2-binding protein (M2BP) bound to the WFA; and
c) determining the therapeutic effect of an anti-viral agent in treatment for liver disease based on the assayed value of the glycosylated M2BP.

* * * * *

UNITED STATES PATENT AND TRADEMARK OFFICE
CERTIFICATE OF CORRECTION

PATENT NO.       : 8,623,608 B2
APPLICATION NO.  : 13/374807
DATED            : January 7, 2014
INVENTOR(S)      : Hisashi Narimatsu et al.

Page 1 of 1

It is certified that error appears in the above-identified patent and that said Letters Patent is hereby corrected as shown below:

On the Title Page

Left column, item (73), under "Assignee", replace "Nagoya University," with --Nagoya City University,--.

Signed and Sealed this
Thirteenth Day of May, 2014

Michelle K. Lee
*Deputy Director of the United States Patent and Trademark Office*